US011793669B2

(12) United States Patent
Devlin et al.

(10) Patent No.: US 11,793,669 B2
(45) Date of Patent: Oct. 24, 2023

(54) COMBINATION THERAPY INTRAVAGINAL RINGS

(71) Applicant: The Population Council, Inc., New York, NY (US)

(72) Inventors: Brid Devlin, Berwyn, PA (US); Jonathon Daryll Holt, Durham, NC (US); Andrew Nathan Brimer, Bethlehem, PA (US); Jeremy Peter Nuttall, Newtown Square, PA (US); Karl Malcolm, Belfast (GB); Susan Margaret Fetherston, Belfast (GB); Peter John James Boyd, Ballyclare (GB)

(73) Assignee: The Population Council, Inc., New York, NY (US)

( * ) Notice: Subject to any disclaimer, the term of this patent is extended or adjusted under 35 U.S.C. 154(b) by 0 days.

(21) Appl. No.: 17/577,708

(22) Filed: Jan. 18, 2022

(65) Prior Publication Data
US 2022/0378603 A1 Dec. 1, 2022

Related U.S. Application Data

(60) Continuation of application No. 16/155,473, filed on Oct. 9, 2018, now Pat. No. 11,259,956, which is a
(Continued)

(51) Int. Cl.
*A61F 6/06* (2006.01)
*A61K 31/46* (2006.01)
(Continued)

(52) U.S. Cl.
CPC ............... *A61F 6/06* (2013.01); *A61K 31/46* (2013.01); *A61K 31/505* (2013.01); *A61K 31/567* (2013.01); *A61K 45/06* (2013.01)

(58) Field of Classification Search
CPC ...... A61K 45/06; A61K 31/505; A61K 31/57; A61K 9/0036; A61K 2300/00;
(Continued)

(56) References Cited

U.S. PATENT DOCUMENTS 3,545,439 A 12/1970 Kalamazoo et al.
3,710,795 A 1/1973 Higuchi et al.
(Continued)

FOREIGN PATENT DOCUMENTS

EP 81370 A1 6/1983
EP 1732520 B1 6/2009
(Continued)

OTHER PUBLICATIONS

U.S. Appl. No. 14/540,530, filed Nov. 13, 2014, U.S. Pat. No. 10,137,031, Issued.
(Continued)

*Primary Examiner* — Ophelia A Hawthorne
(74) *Attorney, Agent, or Firm* — McCarter & English, LLP; Maria Laccotripe Zacharakis; Marcie B. Clarke

(57) ABSTRACT

The present invention provides improved intravaginal drug delivery devices, i.e., intravaginal rings, useful for the prophylactic administration of dapivirine in combination with either an antimicrobial compound or a contraceptive to a human. The present invention also provides methods of blocking DNA polymerization by an HIV reverse transcriptase enzyme, methods of preventing HIV infection in a female human, methods of treating HIV infection in a female human, methods of preventing unintended pregnancy in a female human, and methods of preparing intravaginal rings.

20 Claims, 28 Drawing Sheets

Ring configurations

Related U.S. Application Data division of application No. 14/540,530, filed on Nov. 13, 2014, now Pat. No. 10,137,031.

(60) Provisional application No. 61/904,073, filed on Nov. 14, 2013.

(51) Int. Cl.
   *A61K 31/567* (2006.01)
   *A61K 31/505* (2006.01)
   *A61K 45/06* (2006.01)

(58) Field of Classification Search
   CPC ......... A61K 31/46; A61K 31/444; A61F 6/06; A61F 2013/8414; A61F 13/2051; C07C 51/43
   See application file for complete search history.

(56) References Cited

U.S. PATENT DOCUMENTS

| | | |
|---|---|---|
| 3,832,252 A | 8/1974 | Higuchi et al. |
| 3,854,480 A | 12/1974 | Zaffaroni |
| 3,916,899 A | 11/1975 | Theeuwes et al. |
| 3,920,805 A | 11/1975 | Roseman |
| 3,948,254 A | 4/1976 | Zaffaroni |
| 3,991,760 A | 11/1976 | Drobish et al. |
| 3,995,633 A | 12/1976 | Gougeon |
| 4,012,496 A | 3/1977 | Schopflin et al. |
| 4,012,497 A | 3/1977 | Schopflin |
| 4,014,987 A | 3/1977 | Heller et al. |
| 4,016,251 A | 4/1977 | Higuchi et al. |
| 4,043,339 A | 8/1977 | Roseman |
| 4,093,709 A | 6/1978 | Choi et al. |
| 4,155,991 A | 5/1979 | Schopflin et al. |
| 4,202,880 A | 5/1980 | Fildes et al. |
| 4,235,236 A | 11/1980 | Theeuwes |
| 4,237,885 A | 12/1980 | Wong et al. |
| 4,237,888 A | 12/1980 | Roseman et al. |
| 4,250,611 A | 2/1981 | Wong |
| 4,286,587 A | 9/1981 | Wong |
| 4,292,965 A | 10/1981 | Nash et al. |
| 4,469,671 A | 9/1984 | Zimmerman et al. |
| 4,493,699 A | 1/1985 | Zimmerman et al. |
| 4,553,972 A | 11/1985 | Vickery |
| 4,564,362 A | 1/1986 | Burnhill |
| 4,589,880 A | 5/1986 | Dunn et al. |
| 4,596,576 A | 6/1986 | de Nijs |
| 4,762,717 A | 8/1988 | Crowley, Jr. |
| 4,822,616 A | 4/1989 | Zimmermann et al. |
| 4,888,074 A | 12/1989 | Pocknell |
| 4,997,653 A | 3/1991 | Igarashi |
| 5,398,698 A | 3/1995 | Hiller et al. |
| 5,660,187 A | 8/1997 | Hiller et al. |
| 5,694,947 A | 12/1997 | Lehtinen et al. |
| 5,788,980 A | 8/1998 | Nabahi |
| 5,855,906 A | 1/1999 | McClay |
| 5,869,081 A | 2/1999 | Jackanicz et al. |
| 5,972,372 A | 10/1999 | Saleh et al. |
| 5,989,581 A | 11/1999 | Groenewegen |
| 6,039,968 A | 3/2000 | Nabahi |
| 6,063,325 A | 5/2000 | Nahill et al. |
| 6,086,909 A | 7/2000 | Harrison et al. |
| 6,103,256 A | 8/2000 | Nabahi |
| 6,126,958 A | 10/2000 | Saleh et al. |
| 6,264,973 B1 | 7/2001 | Mahashabde et al. |
| 6,394,094 B1 | 5/2002 | McKenna et al. |
| 6,566,095 B1 | 5/2003 | Markham et al. |
| 6,740,333 B2 | 5/2004 | Beckett et al. |
| 6,951,654 B2 | 10/2005 | Malcolm et al. |
| 7,001,912 B2 | 2/2006 | Kuki et al. |
| 7,094,909 B2 | 8/2006 | Kucera et al. |
| 7,109,230 B2 | 9/2006 | Erickson et al. |
| 7,138,408 B2 | 11/2006 | Kuki et al. |
| 7,169,932 B2 | 1/2007 | Kucera et al. |
| 7,199,148 B2 | 4/2007 | Tahri et al. |
| 7,521,064 B2 | 4/2009 | Saxena et al. |
| 7,521,074 B2 | 4/2009 | Mikkelsen et al. |
| 7,824,383 B2 | 11/2010 | Sokal et al. |
| 7,829,112 B2 | 11/2010 | Ron et al. |
| 7,833,545 B2 | 11/2010 | Ron et al. |
| 7,838,024 B2 | 11/2010 | Ron et al. |
| 7,850,986 B2 | 12/2010 | Riihimaki |
| 7,883,718 B2 | 2/2011 | Ron et al. |
| 7,910,126 B2 | 3/2011 | Ahmed et al. |
| 7,935,710 B2 | 5/2011 | Van Roey et al. |
| 8,057,817 B2 | 11/2011 | Shalaby |
| 8,062,658 B2 | 11/2011 | Shalaby et al. |
| 8,580,294 B2 | 11/2013 | Malcolm et al. |
| 10,137,031 B2 * | 11/2018 | Devlin .................. A61K 31/567 |
| 11,259,956 B2 * | 3/2022 | Devlin .................. A61K 45/06 |
| 2002/0161352 A1 | 10/2002 | Lin et al. |
| 2003/0059456 A1 | 3/2003 | Malcolm et al. |
| 2003/0060785 A1 | 3/2003 | Lavean et al. |
| 2003/0134803 A1 | 7/2003 | Cherr et al. |
| 2003/0232088 A1 | 12/2003 | Huang et al. |
| 2004/0089308 A1 | 5/2004 | Welch |
| 2004/0126369 A1 | 7/2004 | Payne et al. |
| 2004/0265355 A1 | 12/2004 | Shalaby |
| 2005/0042292 A1 | 2/2005 | Muldoon et al. |
| 2005/0148995 A1 | 7/2005 | Shepard et al. |
| 2005/0197651 A1 | 9/2005 | Chen et al. |
| 2005/0250746 A1 | 11/2005 | Iammatteo |
| 2006/0083778 A1 | 4/2006 | Allison et al. |
| 2006/0100154 A1 | 5/2006 | Koch et al. |
| 2006/0280771 A1 | 12/2006 | Groenewegen et al. |
| 2007/0037780 A1 | 2/2007 | Ebert et al. |
| 2007/0043332 A1 | 2/2007 | Malcolm et al. |
| 2007/0077269 A1 | 4/2007 | Woodward |
| 2007/0196433 A1 | 8/2007 | Ron et al. |
| 2007/0243229 A1 | 10/2007 | Smith et al. |
| 2008/0206310 A1 | 8/2008 | Davis |
| 2008/0268022 A1 | 10/2008 | McCabe et al. |
| 2008/0300197 A1 | 12/2008 | Kabir et al. |
| 2009/0004246 A1 | 1/2009 | Woolfson et al. |
| 2009/0060997 A1 | 3/2009 | Seitz et al. |
| 2009/0081278 A1 | 3/2009 | De Graaff et al. |
| 2009/0142313 A1 | 6/2009 | Talling et al. |
| 2009/0202612 A1 | 8/2009 | Ahmed et al. |
| 2009/0291120 A1 | 11/2009 | Tuominen et al. |
| 2010/0034810 A1 | 2/2010 | Heeres et al. |
| 2010/0034863 A1 | 2/2010 | Fairhurst et al. |
| 2010/0040671 A1 | 2/2010 | Ahmed et al. |
| 2010/0087402 A1 | 4/2010 | Wang et al. |
| 2010/0104619 A1 | 4/2010 | De Graaff et al. |
| 2010/0129425 A1 | 5/2010 | De Graaff et al. |
| 2010/0166826 A1 | 7/2010 | Kiser |
| 2010/0203104 A1 | 8/2010 | De Graaff et al. |
| 2010/0247564 A1 | 9/2010 | Lee et al. |
| 2010/0285094 A1 | 11/2010 | Gupta |
| 2010/0330138 A1 | 12/2010 | Shalaby et al. |
| 2011/0008409 A1 | 1/2011 | Seitz et al. |
| 2011/0045076 A1 | 2/2011 | Kiser et al. |
| 2011/0165093 A1 | 7/2011 | Van Roey et al. |
| 2011/0189257 A1 | 8/2011 | Chin et al. |
| 2011/0208135 A1 | 8/2011 | Hakala |
| 2011/0236462 A1 | 9/2011 | Shaked et al. |
| 2012/0093911 A1 | 4/2012 | Malcolm et al. |
| 2013/0289027 A1 | 10/2013 | De La Rosa |
| 2014/0056961 A1 | 2/2014 | Malcolm et al. |
| 2014/0128345 A1 | 5/2014 | Woodrow et al. |

FOREIGN PATENT DOCUMENTS

| | | |
|---|---|---|
| EP | 2179722 A1 | 4/2010 |
| WO | WO-1994/016652 A1 | 8/1994 |
| WO | WO-1995/009641 A1 | 4/1995 |
| WO | WO-1997/031631 A1 | 9/1997 |
| WO | WO-1998/008471 A1 | 3/1998 |
| WO | WO-1999/038468 A1 | 8/1999 |
| WO | WO-1999/050250 A1 | 10/1999 |
| WO | WO-2000/074684 A1 | 12/2000 |
| WO | WO-2002/040021 A2 | 5/2002 |
| WO | WO-2002/056793 A2 | 7/2002 |

(56) References Cited

FOREIGN PATENT DOCUMENTS

| WO | WO-2002/076426 A2 | 10/2002 |
|----|-------------------|---------|
| WO | WO-2003/061579 A2 | 7/2003 |
| WO | WO-2003/077926 A1 | 9/2003 |
| WO | WO-2003/089002 A1 | 10/2003 |
| WO | WO-2003/094920 A1 | 11/2003 |
| WO | WO-2004/022033 A1 | 3/2004 |
| WO | WO-2004/030687 A1 | 4/2004 |
| WO | WO-2004/071508 A1 | 8/2004 |
| WO | WO-2004/103159 A2 | 12/2004 |
| WO | WO-2004/103336 A2 | 12/2004 |
| WO | WO-2005/021750 A1 | 3/2005 |
| WO | WO-2005/089723 A1 | 9/2005 |
| WO | WO-2006/010097 A2 | 1/2006 |
| WO | WO-2006/084082 A1 | 8/2006 |
| WO | WO-2006/084083 A2 | 8/2006 |
| WO | WO-2007/012006 A1 | 1/2007 |
| WO | WO-2007/084211 A2 | 7/2007 |
| WO | WO-2007/092326 A2 | 8/2007 |
| WO | WO-2008/007046 A1 | 1/2008 |
| WO | WO-2008/089488 A2 | 7/2008 |
| WO | WO-2009/003125 A1 | 12/2008 |
| WO | WO-2009/021323 A1 | 2/2009 |
| WO | WO-2009/070638 A1 | 6/2009 |
| WO | WO-2009/094190 A2 | 7/2009 |
| WO | WO-2009/111218 A2 | 9/2009 |
| WO | WO-2009/129459 A1 | 10/2009 |
| WO | WO-2009/141309 A1 | 11/2009 |
| WO | WO-2010/054296 A2 | 5/2010 |
| WO | WO-2010/119030 A1 | 10/2010 |
| WO | WO-2010/133652 A1 | 11/2010 |
| WO | WO-2010/133761 A1 | 11/2010 |
| WO | WO-2011/006067 A1 | 1/2011 |
| WO | WO-2011/011099 A1 | 1/2011 |
| WO | WO-2011/011710 A1 | 1/2011 |
| WO | WO-2011/049948 A2 | 4/2011 |
| WO | WO-2011/067302 A1 | 6/2011 |
| WO | WO-2013/013172 A1 | 1/2013 |

OTHER PUBLICATIONS

U.S. Appl. No. 16/155,473, filed Oct. 9, 2018, U.S. Pat. No. 11,259,956, Issued.

Ampofo et al., Comparative Study of Dissolution Profiles of Microbicide Ring Products Prepared from Different Silicone Elastomer Sources. AAPS, Los Angeles, CA, USA, Poster #M1292, Nov. 9, 2009.

Bell et al., Characterization of silicone elastomer vaginal rings containing HIV microbicide TMC120 by Raman spectroscopy. J Pharm Pharmacol. Feb. 2007;59(2):203-7.

Cohen et al., Antiviral agents and HIV prevention: controversies, conflicts, and consensus. AIDS. Aug. 24, 2012;26(13):1585-98.

Di Fabio et al., Inhibition of vaginal transmission of HIV-1 in hu-SCID mice by the non-nucleoside reverse transcriptase inhibitor TMC120 in a gel formulation. AIDS. Jul. 25, 2003;17(11):1597-604.

Edwards et al., Evaluation of content uniformity using a 3-stream versus 2-stream mixing process to manufacture silicone based vaginal rings. AAPS, Los Angeles, CA, USA, Poster #M1375, Nov. 9, 2009, 1 page.

Gupta et al., Polyurethane intravaginal ring for controlled delivery of dapivirine, a nonnucleoside reverse transcriptase inhibitor of HIV-1. J Pharm Sci. Oct. 2008;97(10):4228-39.

Howard-Sparks et al., Release characteristics of dapivirine and tenofovir from vaginal rings consisting of ethylene vinyl acetate, silicone or polyurethane polymers: options for HIV prevention. AAPS, Los Angeles, CA, USA, Poster #T2363, Nov. 8-12, 2009, 1 page.

Malcolm et al., Long-term, controlled release of the HIV microbicide TMC120 from silicone elastomer vaginal rings. J Antimicrob Chemother. Nov. 2005;56(5):954-6.

Nel et al., Safety and pharmacokinetics of dapivirine delivery from matrix and reservoir intravaginal rings to HIV-negative women. J Acquir Immune Defic Syndr. Aug. 1, 2009;51(4):416-23.

Nel et al., Safety, Acceptability, and Adherence of Monthly Dapivirine Vaginal Microbicide Rings for HIV Prevention. 19th Conference of Retroviruses and Opportunistic Infections. Session 22, Paper #1089, Mar. 2012, 1 page.

Romano et al., Safety and availability of dapivirine (TMC120) delivered from an intravaginal ring. AIDS Res Hum Retroviruses. May 2009;25(5):483-8.

Woolfson et al., Intravaginal ring delivery of the reverse transcriptase inhibitor TMC 120 as an HIV microbicide. Int J Pharm. Nov. 15, 2006;325(1-2):82-9.

\* cited by examiner

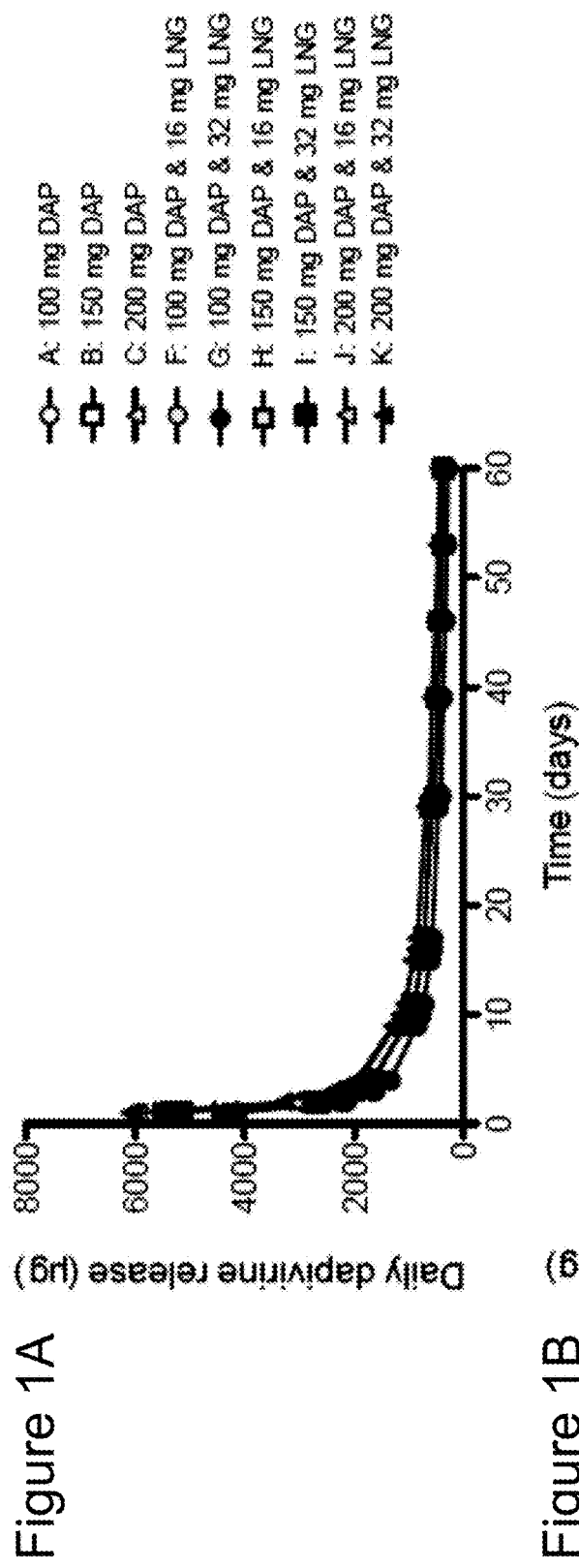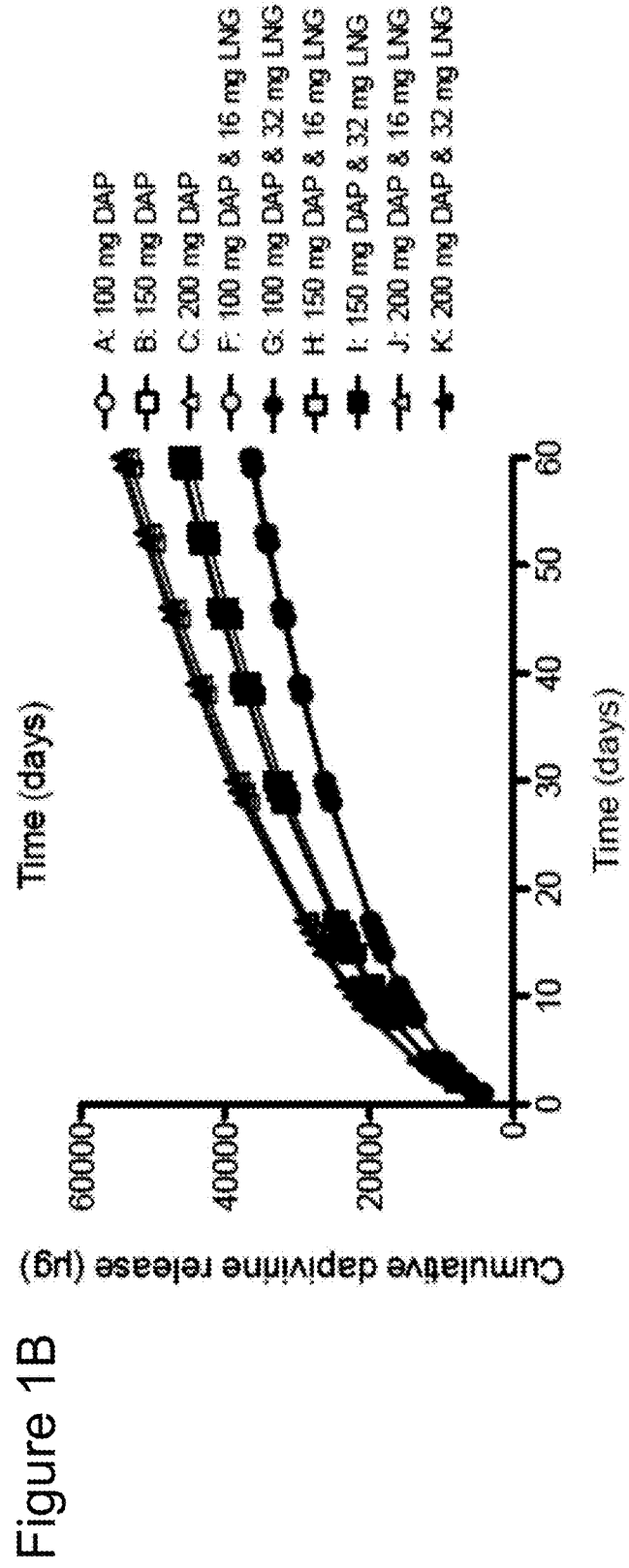
Figure 1A
Figure 1B

| Ring set | Day 1 release (μg) (± sd) | Day 30 release (μg) (± sd) | Cumulative release after 30 days (μg) (± sd) | % Release after 30 days (± sd) | Daily release rate (μg/day[a])[b] | $R^2$ (linear regression analysis)[c] |
|---|---|---|---|---|---|---|
| A | 2047 (± 52) | 138 (± 11) | 9959 (± 109) | 65 (± 1) | 1739 | 0.9982 |
| B | 2255 (± 39) | 162 (± 15) | 11185 (± 188) | 73 (± 2) | 1971 | 0.9992 |
| C | 1932 (± 39) | 131 (± 2) | 9722 (± 55) | 64 (± 1) | 1703 | 0.9954 |

Figure 8

| Ring set | Day 1 release (μg) (± sd) | Day 30 release (μg) (± sd) | Cumulative release after 30 days (μg) (± sd) | % Release after 30 days (± sd) | Daily release rate (μg/day)* | $R^2$ (linear regression analysis)** |
|---|---|---|---|---|---|---|
| A | 44 (± 4) | 115 (± 9) | 3535 (± 40) | 14 (± 0) | 124 | 0.9997 |
| B | 95 (± 78) | 155 (± 34) | 4586 (± 1652) | 18 (± 6) | 159 | 0.9998 |
| C | 32 (± 3) | 107 (± 3) | 3396 (± 57) | 14 (± 0) | 118 | 0.9993 |

|  | Configuration 1 | Configuration 2 |
|---|---|---|
| Description | Reservoir-type vaginal ring | Reservoir-type vaginal ring |
|  | Core: single full-length core loaded with both DAP (2% w/w) and LNG (2% w/w) | Core: two half-length cores: one half core loaded with DAP (2% w/w), one half core loaded with LNG (2% w/w) |
|  | Sheath: blank | Sheath: blank |
| Representative Image* | 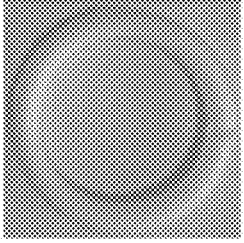 | 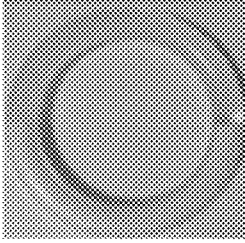 |
| Mean ring mass (g) (± cd) | 7.45 (± 0.02) | 7.46 (± 0.02) |
| Mean core mass (g) (± cd): Core 1 Core 2 | 2.56 (± 0.01) n/a | 1.27 (± 0.02) (DAP) 1.28 (± 0.01) (LNG) |
| Mean sheath mass (g) (± cd) | 4.89 (± 0.02) | 4.91 (± 0.02) |
| Mean theoretical drug loading (mg) (±cd) DAP LNG | 51.2 (± 0.3) 51.2 (± 0.3) | 25.5 (± 0.3) 25.6 (± 0.3) |
| Date of manufacture | 26$^{th}$ Oct 2012 | 31$^{st}$ Oct 2012 |
| Date in vitro release testing commenced | 5$^{th}$ Nov 2012 | 5$^{th}$ Nov 2012 |

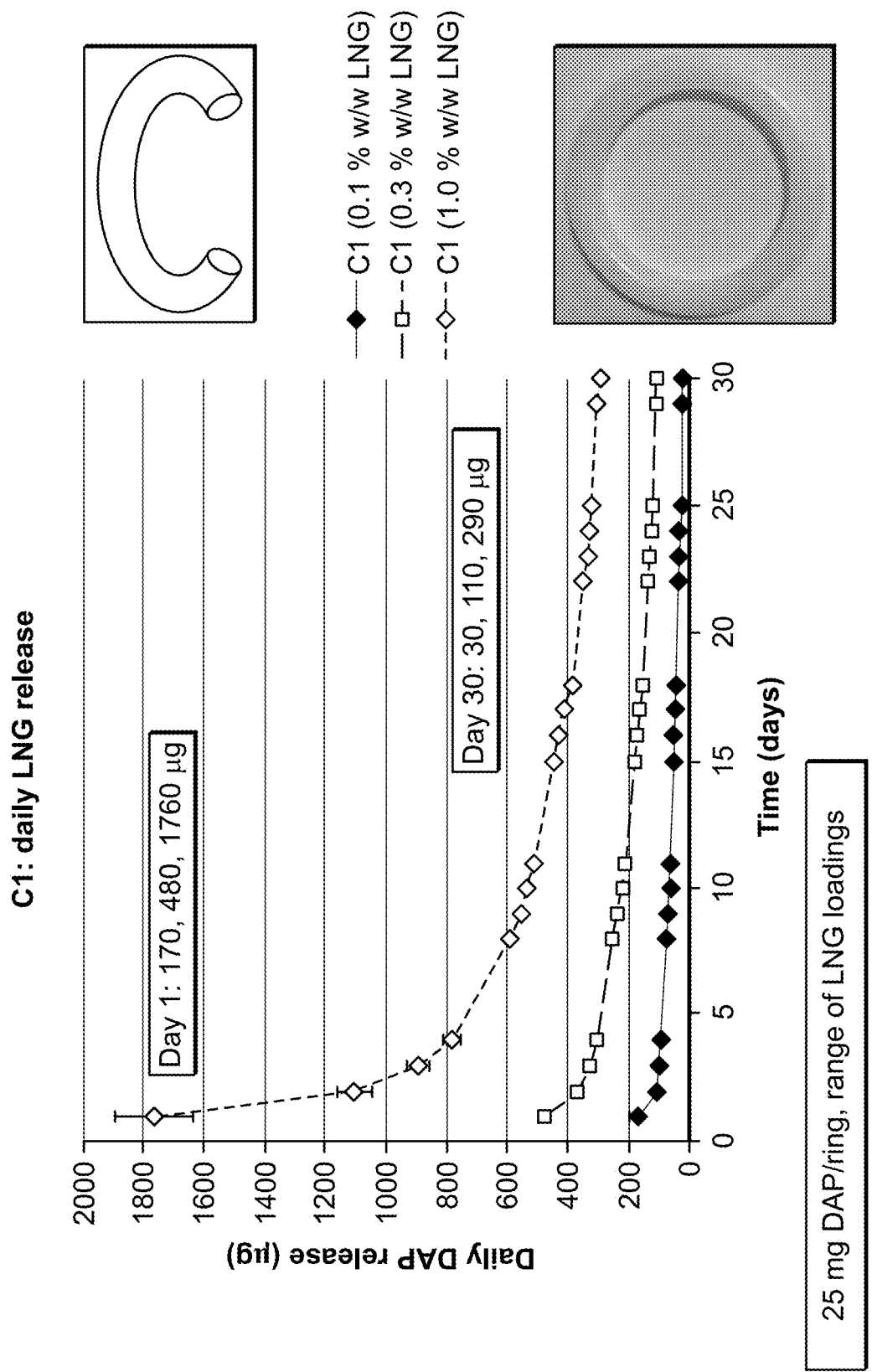

COMBINATION THERAPY INTRAVAGINAL RINGS

RELATED APPLICATION

This application is a continuation application of U.S. patent application Ser. No. 16/155,473, filed Oct. 9, 2018, which is a divisional of U.S. patent application Ser. No. 14/540,530, filed Nov. 13, 2014, which, in turn, claims priority to U.S. Provisional Application No. 61/904,073, filed Nov. 14, 2013. The entire contents of each of the foregoing applications are incorporated herein by reference.

BACKGROUND OF THE INVENTION

The AIDS epidemic continues to exact a devastating toll on the health, economic and political infrastructure, and social fabric of communities worldwide. During 2011, almost 2.5 million people became newly infected with HIV bringing the total number of people living with HIV to an estimated 34.0 million. In the same year, almost 1.7 million people died from AIDS, raising the global death toll to over 35 million since the first cases of AIDS were identified in 1981 (UNAIDS and WHO 2011 AIDS Epidemic Update; December 2011). HIV/AIDS has become the fourth biggest cause of global mortality. Over 95 percent of new infections are occurring in developing countries, where increasing numbers of new HIV infections threaten the sustainability of expanded access to HIV treatment. Developing safe and effective HIV prevention technologies that can be made easily accessible in developing countries is, thus, an urgent public health priority.

Epidemiologic data published in the latest UNAIDS report show that women and girls bear a severe and increasingly heavy burden of the HIV epidemic. In Eastern Europe and Central Asia, an estimated 26% of adults living with HIV in 2007 were women aged 15 years or older, compared with 23% in 2001. In sub-Saharan Africa, women comprised 61% of HIV-infected adults, and among young people (aged 15-24 years) the ratio of infection had risen to three women for every man (UNAIDS and WHO 2007 AIDS Epidemic Update; December 2007).

Each year, there are also 80 million unintended pregnancies, and 358,000 women die annually from pregnancy-related complications. More than 200 million women in developing countries lack access to contraception. Accordingly, there is a strong need for developing combination products that can prevent both HIV infection and unintended pregnancy in females.

Unprotected heterosexual intercourse is currently the leading mode of HIV infection and unintended pregnancy among females. Correct and consistent use of latex condoms is one proven method of preventing HIV transmission and unintended pregnancy; however, condoms are widely regarded as inadequate prevention options for women if they are unable to negotiate condom use for fear of abuse or accusations of infidelity. Additionally, women who have sex with men in exchange for gifts or money may be reluctant to use condoms if the men are willing to pay more for sex without a condom. The female condom has been marketed as an alternative barrier method, but this device is relatively costly and requires a certain level of skill, as well as acceptance by the male partner. Developing HIV and pregnancy prevention options that women can use with or without their partner's knowledge is a pressing global concern, especially given the rapidly growing HIV infection rate among women and the absence of an effective vaccine.

Topical microbicides that can be self-administered to the vagina are one such promising alternative. Multiple clinical trials with various microbicides have been completed or are currently underway, most of which involve microbicides in gel formulation delivered via a single use applicator used prior to coitus. In order for a microbicide to be effective, it is essential that it be used correctly. Therefore it is important that a microbicide is acceptable to users, and it is likely that products that can be used less frequently will be more acceptable and will achieve better user adherence. Additionally, combination products that could prevent both HIV transmission and unintended pregnancy would be more acceptable to users.

Vaginal rings that need only be replaced at relatively long intervals may therefore have benefits over other dosage forms that must be used more frequently. Ring-shaped devices for the controlled administration of steroid substances (substantially water-insoluble drugs) into the vagina are known in the art, such as Estring®, Femring® and Nuvaring®. There are two basic types of vaginal rings: reservoir rings and matrix rings.

A reservoir ring comprises a full or partial-length core loaded with the drug substance, which is completely surrounded by a non-medicated sheath. Accordingly, the release of drug substances from such rings is dependent upon permeation (i.e., molecular dissolution and subsequent diffusion) of the core-loaded drug substance through the outer sheath. Release rates can be modified by changing the thickness of the rate-controlling sheath and/or the length of the drug-loaded core. Reservoir rings were developed to provide controlled (that is, constant daily) release rates. The polymeric materials used in the construction of commercial vaginal rings are typically hydrophobic materials, such as silicone elastomer and poly(ethylene-co-vinyl acetate) (PEVA) materials. Alternatively, polyurethane may be used.

To date, no combination therapy intravaginal rings have been successfully developed. Combining different drugs in the same intravaginal ring poses unique challenges, due to the different solubility and target release rates of different drugs. Accordingly, there remains a need for the development of improved intravaginal rings which can be loaded with a combination of antimicrobial drugs to prevent the transmission of HIV, or a combination of an antimicrobial drug and a contraceptive to prevent the transmission of HIV and unintended pregnancy.

SUMMARY OF THE INVENTION

The present invention provides combination therapy intravaginal drug delivery devices, i.e., intravaginal rings, useful for the administration of therapeutic and/or prophylactic agents to a human. The intravaginal rings of the invention may provide long-term controlled release of dapivirine and an antimicrobial agent, such as maraviroc, DS003, darunavir, GSK1265744 or BMS-663068, or dapivirine and a contraceptive, such as levonorgestrel, estradiol, etonogestrel or nestorone. Surprisingly, the combination of dapivirine and either an antimicrobial compound or a contraceptive in the intravaginal rings of the invention results in the formation of a eutectic composition and provides increased release rates as compared to previous intravaginal rings.

In one aspect, the invention provides an intravaginal ring comprising dapivirine and an antimicrobial compound, wherein less than about 7 mg of dapivirine is released in vitro from said ring during an initial 24 hour period of release, and wherein the release rate of the antimicrobial compound from the intravaginal ring in vitro is increased as compared to the release rate of the antimicrobial compound from an intravaginal ring comprising the antimicrobial compound without dapivirine.

In another aspect, the invention provides an intravaginal ring comprising dapivirine and a contraceptive, wherein less than about 7 mg of dapivirine is released in vitro from said ring during an initial 24 hour period of release, and wherein the release rate of the contraceptive from the intravaginal ring in vitro is increased as compared to the release rate of the contraceptive from an intravaginal ring comprising the contraceptive without dapivirine.

In another aspect, the invention provides an intravaginal ring comprising dapivirine and an antimicrobial compound, wherein less than about 7 mg of dapivirine is released in vitro from said ring during an initial 24 hour period of release, and wherein the dapivirine in the intravaginal ring increases the solubility of the antimicrobial compound as compared to the solubility of the antimicrobial compound in an intravaginal ring comprising the antimicrobial compound without dapivirine.

In another aspect, the invention provides an intravaginal ring comprising dapivirine and a contraceptive, wherein less than about 7 mg of dapivirine is released in vitro from said ring during an initial 24 hour period of release, and wherein the dapivirine in the intravaginal ring increases the solubility of the contraceptive as compared to the solubility of the contraceptive in an intravaginal ring comprising the contraceptive without dapivirine.

In another aspect, the invention provides an intravaginal ring comprising a eutectic composition comprising dapivirine and an antimicrobial compound, wherein less than about 7 mg of dapivirine is released in vitro from said ring during an initial 24 hour period of release.

In another aspect, the invention provides an intravaginal ring comprising a eutectic composition comprising dapivirine and a contraceptive, wherein less than about 7 mg of dapivirine is released in vitro from said ring during an initial 24 hour period of release.

In one embodiment, between about 100 and about 700 µg of dapivirine is released in vitro each day for 23 days after an initial 7 day period of release.

In one embodiment, the antimicrobial compound is released in vitro at a rate of between about 200 µg per day and about 2000 µg per day, between about 400 µg per day and about 4000 µg per day, between about 550 µg per day and about 5500 µg per day, or between about 800 µg per day and about 8000 µg per day for 23 days or 53 days after an initial 7 day period of release.

In one embodiment, the intravaginal ring is a matrix-type ring, and wherein the contraceptive is released in vitro at a rate of about 35 µg per day to about 70 µg per day for about 53 days after an initial 7 day period of release. In another embodiment, the contraceptive is released in vitro at a rate of about 35 µg per day to about 70 µg per day for about 53 days after an initial 7 day period of release.

In one embodiment, the intravaginal ring is a reservoir-type ring, and wherein less than about 2 mg of the contraceptive is released from the ring during an initial 24 hour period of release, and wherein about 20 µg per day to about 290 µg per day of the contraceptive is released in vitro after an initial 7 day period of release. In another embodiment, less than about 1 mg of the contraceptive is released in vitro from the ring during the initial 24 hour period of release. In another embodiment, about 35 µg per day to about 70 µg per day of the contraceptive is released in vitro after the initial 7 day period of release for about 23 days. In another embodiment, about 35 µg per day to about 70 µg per day of the contraceptive is released in vitro after the initial 7 day period of release for about 53 days.

In one embodiment, less than about 100 µg per day of the contraceptive is released in vitro after the initial 7 day period of release for about 23 days. In another embodiment, less than about 100 µg per day of the contraceptive is released in vitro after the initial 7 day period of release for about 53 days.

In one embodiment, less than about 15 µg per day of the contraceptive is released in vitro after the initial 7 day period of release for about 23 days. In another embodiment, less than about 15 µg per day of the contraceptive is released in vitro after the initial 7 day period of release for about 53 days.

In one embodiment, the ring is a matrix-type ring. In another embodiment, the ring is a platinum-catalyzed ring. In another embodiment, the ring comprises a silicone polymer, an EVA polymer, or a polyurethane polymer.

In another embodiment, the ring is a reservoir-type ring comprising a core and a sheath. In one embodiment, the dapivirine and the contraceptive, or the dapivirine and the antimicrobial compound are present in the core of the reservoir-type ring, and the sheath is blank. In another embodiment, the dapivirine and the contraceptive, or the dapivirine and the antimicrobial compound are present in two separate half-length cores, and the sheath is blank. In one embodiment, the contraceptive or the antimicrobial compound are present in the core, and the dapivirine is present in the sheath. In one embodiment, the core is platinum-catalyzed. In one embodiment, the core comprises a silicone polymer, an EVA polymer, or a polyurethane polymer.

In one embodiment, the antimicrobial compound is maraviroc. In another embodiment, the antimicrobial compound is DS003. In another embodiment, the antimicrobial compound is darunavir, GSK1265744 or BMS-663068.

In one embodiment, the contraceptive is levonorgestrel. In another embodiment, the contraceptive is estradiol, etonorgestrel or nestorone.

In one embodiment, dapivirine is present in the ring in a therapeutically effective amount. In another embodiment, dapivirine is present in the ring in a prophylactically effective amount. In one embodiment, about 10 to about 800 mg of dapivirine is present in the ring. In one embodiment, about 100 mg of dapivirine is present in the ring. In another embodiment, about 150 mg of dapivirine is present in the ring. In another embodiment, about 200 mg of dapivirine is present in the ring. In another embodiment, about 10 to about 30 mg of dapivirine is present in the ring. In another embodiment, about 25 mg of dapivirine is present in the ring. In another embodiment, about 15 mg of dapivirine is present in the ring.

In one embodiment, the antimicrobial compound is present in the ring in a therapeutically effective amount. In another embodiment, the antimicrobial compound is present in the ring in a prophylactically effective amount. In another embodiment, about 100 to about 1600 mg of the antimicrobial compound is present in the ring. In another embodiment, about 100 to about 800 mg of the antimicrobial compound is present in the ring. In another embodiment, about 100 mg, 400 mg, 800 mg or 1600 mg of the antimicrobial compound is present in the ring.

In one embodiment, the contraceptive is present in the ring in a therapeutically effective amount. In another embodiment, the contraceptive is present in the ring in a prophylactically effective amount. In one embodiment, about 10 to about 800 mg of the contraceptive is present in the ring. In another embodiment, about 10 to about 100 mg of the contraceptive is present in the ring. In one embodiment, about 16 mg of the contraceptive is present in the ring. In another embodiment, about 25 mg of the contraceptive is present in the ring. In another embodiment, about 32 mg of the contraceptive is present in the ring. In another embodiment, about 50 mg of the contraceptive is present in the ring.

In one embodiment, release rates are stable following 3 months of storage. In another embodiment, release rates are stable following 6 months of storage. In another embodiment, release rates are stable following 12 months of storage. In another embodiment, release rates are stable following 36 months of storage.

In one embodiment, the intravaginal ring has an outer diameter of about 58 mm, an internal diameter of about 43 mm and a cross-sectional diameter of about 7.6 mm. In another embodiment, the intravaginal ring has an outer diameter of about 57 mm and a cross-sectional diameter of about 7.8 mm.

In another aspect, the invention provides a method of blocking DNA polymerization by an HIV reverse transcriptase enzyme in a female human by inserting an intravaginal ring of the invention into the vagina of the female human.

In another aspect, the invention provides a method of preventing HIV infection in a female human, comprising the step of inserting an intravaginal ring of the invention into the vagina of the female human.

In another aspect, the invention provides a method of treating HIV infection in a female human, comprising the step of inserting an intravaginal ring of the invention into the vagina of the female human.

In another aspect, the invention provides a method of preventing pregnancy and blocking DNA polymerization by an HIV reverse transcriptase enzyme in a female human by inserting an intravaginal ring of the invention into the vagina of the female human.

In another aspect, the invention provides a method of preventing pregnancy and preventing HIV infection in a female human by inserting an intravaginal ring of the invention into the vagina of the female human.

In another aspect, the invention provides a method of preventing pregnancy treating HIV infection in a female human by inserting an intravaginal ring of the invention into the vagina of the female human.

Other features and advantages of the invention will be apparent from the following detailed description and claims.

BRIEF DESCRIPTION OF THE DRAWINGS

FIG. 1A and FIG. 1B depict the mean daily (FIG. 1A, ±sd) and cumulative (FIG. 1B) release of dapivirine (DAP) from MED-4870 matrix rings comprising DAP (100, 150 and 200 mg per ring), with or without levonorgestrel (LNG) (0, 16 and 32 mg per ring) over 60 days.

FIG. 8 is a table depicting a summary of the DAP release data for each ring set in Example 2. Release of DAP follows $t^{0.5}$ kinetics, i.e. daily release declines over time. This is typical of matrix rings, where drug is dispersed uniformly throughout the silicone elastomer. It is therefore not appropriate to report the average daily release rate of DAP in terms of µg/day, since this would be misleading. According to Higuchi's equation, cumulative release from matrix devices is directly proportional to the square root of time. The value in the table was obtained by plotting cumulative release against the square root of time and determining the gradient of the best-fit linear trend line. Linear regression analysis refers to the linear regression of a plot of cumulative release against root time.

FIG. 9 is a table depicting a summary of the LNG release data for each ring set in Example 2. Release of LN follows zero order kinetics, i.e. the mass released each day is constant. This is because LN is loaded into the core of the ring and is surrounded by a rate-limiting silicone elastomer sheath (reservoir ring). It is therefore appropriate to report the mean daily release of LN in terms of µg/day. The value in the table was obtained by plotting cumulative release against time and determining the gradient of the best-fit linear trend line. Linear regression analysis refers to the linear regression of a plot of cumulative release against root time.

FIG. 10 depicts details of the ring configurations used in Example 3. Configuration 1 depicts the visible gap between the two ends of the core, due to the cut made in the core prior to over molding. The two separate half-length cores are clearly visible in the Core 2 image wherein the white core is the DAP-loaded segment (white appearance due to the micronized DAP), while the more transparent core is the LNG-loaded segment (LNG was not micronized; small particles of LNG were clearly visible in the silicone elastomer, although these may not be evident from the image in the table.)

FIG. 14A, FIG. 14B, FIG. 14C, and FIG. 14D depict (FIG. 14A) daily dapivirine release, (FIG. 14B) cumulative dapivirine release, (FIG. 14C) daily LNG release, and (FIG. 15D) cumulative LNG release from ring type C1, which is a matrix-type ring comprising both DAP and LNG.

DETAILED DESCRIPTION OF THE INVENTION

Figure 2A:
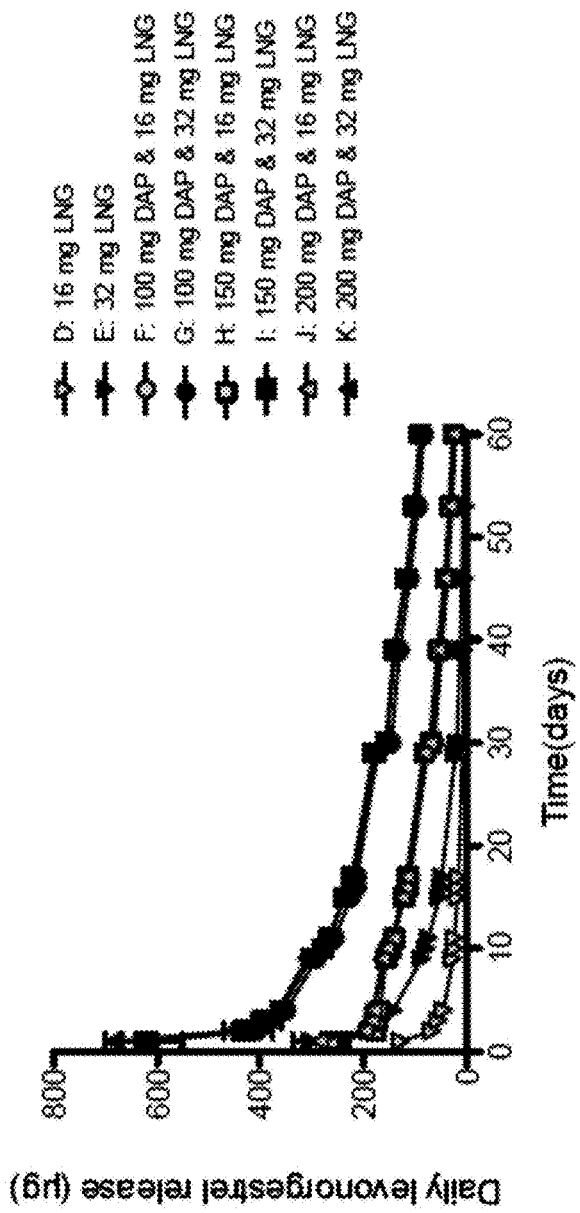
FIG. 2A and FIG. 2B depict the mean daily (FIG. 2A, ±sd) and cumulative (FIG. 2B) release of LNG from MED-4870 matrix rings comprising LNG (16 and 32 mg per ring), with or without DAP (0, 100, 150 and 200 mg per ring) over 60 days.

The present invention provides combination therapy intravaginal drug delivery devices, i.e., intravaginal rings, useful for the administration of therapeutic and/or prophylactic agents to a human. The intravaginal rings of the invention may provide long-term controlled release of dapivirine and an antimicrobial agent, such as maraviroc, DS003, darunavir, GSK1265744 or BMS-663068, or dapivirine and a contraceptive, such as levonorgestrel, estradiol, etonorgestrel or nestorone. Surprisingly, the combination of dapivirine and either an antimicrobial compound or a contraceptive in the intravaginal rings of the invention results in the formation of a eutectic composition and provides increased release rates as compared to previous intravaginal rings.

As used herein, the term "intravaginal ring" or "vaginal ring" refers to a doughnut-shaped polymeric drug delivery device which is designed to be inserted into the vagina of a female human in order to provide controlled release of drugs to the vagina over an extended period of time. Several single-indication intravaginal rings are currently available, including Estring® and Femring®, for the treatment of symptoms of post-menopause, and NuvaRing®, a contraceptive vaginal ring.

The intravaginal rings of the instant invention provide controlled release of dapivirine, alone or in combination with an antimicrobial compound or a contraceptive, and may have any shape and be of any dimensions compatible with intravaginal administration to a female human. Such a ring can be self-inserted into the vagina, where it is held in place due to its shape and inherent elasticity. Such a device provides high user adherence, ease of application and exhibits no leakage or messiness on insertion and subsequent placement within the vaginal space.

As used herein, the term "dapivirine" refers to (4-[[4-[(2,4,6-trimethylphenyl)amino]-2-pyrimidinyl]amino]benzonitrile), a non-nucleoside reverse transcriptase inhibitor. Dapivirine is useful in the prevention and/or treatment of retroviral infection, such as HIV-1 infection. Dapivirine is a crystalline compound that is white to slightly beige in color, has a melting point of about 220° C. and is virtually insoluble in water. More specifically, the solubility of dapivirine is less than 0.001 mg/mLf of water (i.e., less than 1 μg/ml of water). The intravaginal rings of the instant invention may use micronized dapivirine. A composite result (four samples taken of micronized material) showed that 88.15% of the material had a particle size of less than 5 microns (μM).

As used herein, the term "antimicrobial compound" or "antimicrobial agent" (used interchangeably herein) refers to a compound or agent which is capable of inhibiting or destroying the growth of a microbial organism. In a preferred embodiment of the invention, the antimicrobial compound is a non-nucleoside reverse transcriptase inhibitor ("NNRTI"). In another embodiment, the NNRTI is a substituted di-amino pyrimidine derivative. In another embodiment, the antimicrobial compound is a viral entry inhibitor. In one embodiment of the invention, the antimicrobial compound is maraviroc. In one embodiment of the invention, the antimicrobial is DS003. In another embodiment of the invention, the antimicrobial compound is darunavir, GSK 1265744 or BMS-663068. The term "antimicrobial compound" is intended to embrace antibacterial agents, antifungal agents, antiprotozoal agents, antiviral agents and mixtures thereof. For purposes of this invention, the term "antimicrobial compound" or "antimicrobial agent" is a compound other than dapivirine. That is, the intravaginal rings of the invention do not contain only dapivirine as the active agent.

As used herein, the term "contraceptive" refers to an active agent that prevents conception or pregnancy. Contraceptives are well-known in the art and include, but are not limited to, 17a-ethinyl-levonorgestrel-17b-hydroxy-estra-4,9,11-trien-3-one, estradiol, etonogestrel, levonorgestrel, medroxyprogesterone acetate, nestorone, norethindrone, and progesterone. In one embodiment of the invention, the contraceptive is levonorgestrel. In one embodiment of the invention, the contraceptive is estradiol. In one embodiment of the invention, the contraceptive is etonorgestrel. In one embodiment of the invention, the contraceptive is nestorone.

As used herein, the term "eutectic composition" refers to a mixture of chemical compounds that have a single chemical composition that solidifies at a lower temperature than any other composition made up of the same ingredients. The composition is known as the "eutectic composition" and the temperature at which it solidifies is known as the "eutectic temperature." On a phase diagram, the intersection of the eutectic temperature and the eutectic composition gives the "eutectic point." Non-eutectic mixtures will display solidification of one component of the mixture before the other.

As used herein, the term "matrix ring" or "matrix-type ring" refers to an intravaginal ring in which the active agent or agents are homogenously distributed throughout the ring. Matrix rings are typically manufactured by injection molding or extrusion of a compound-containing active mix, leading to the uniform distribution of the active compound throughout the ring. The matrix-type rings of the instant invention may comprise dapivirine and either an antimicrobial agent or a contraceptive agent dispersed in silicone elastomer with normal propylorthosilicate (NPOS) crosslinker. This active mix is subsequently cured using a catalyst, such as platinum (with curing achieved by an addition reaction). The matrix-type rings of the invention may also comprise polyurethane or EVA. Matrix-type intravaginal rings permit single intravaginal dosing of active agent(s), with an initially high "loading" and a subsequent, lower "maintenance" release profile.

Figure 13:
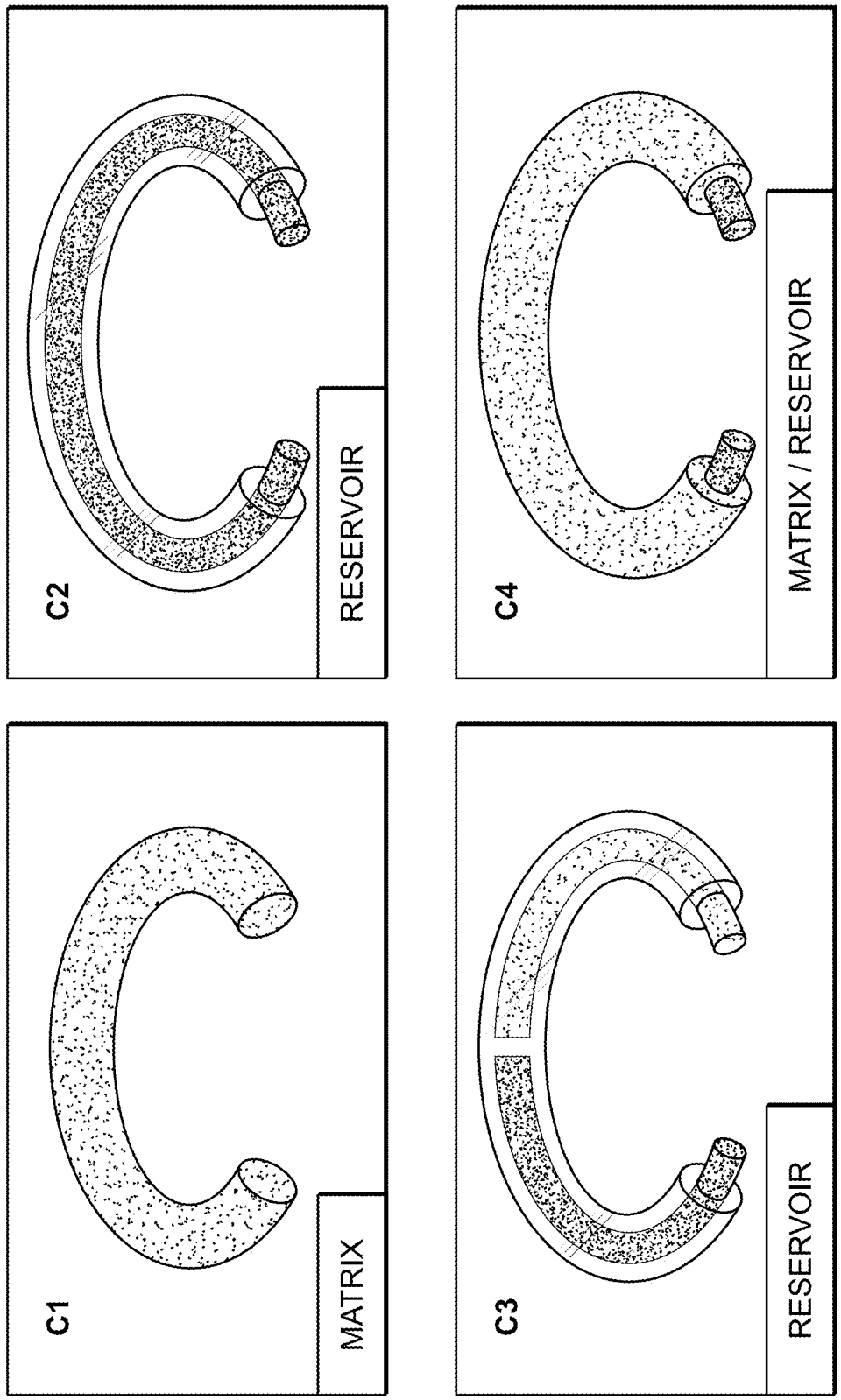
FIG. 13 depicts the four types of ring configurations used in Example 4. Ring type C1 is a matrix-type ring, comprising both dapivirine and LNG. Ring type C2 is a reservoir-type ring, with both dapirivine and LNG loaded in a core which is surrounded by a blank sheath. Ring type C3 is a reservoir-type ring, with dapivirine loaded in half of the core and LNG loaded in the other half of the core, surrounded by a blank sheath. Ring type C4 is a combination matrix/reservoir-type ring, with LNG loaded in the core and dapivirine loaded in the sheath.
Figure 14A:
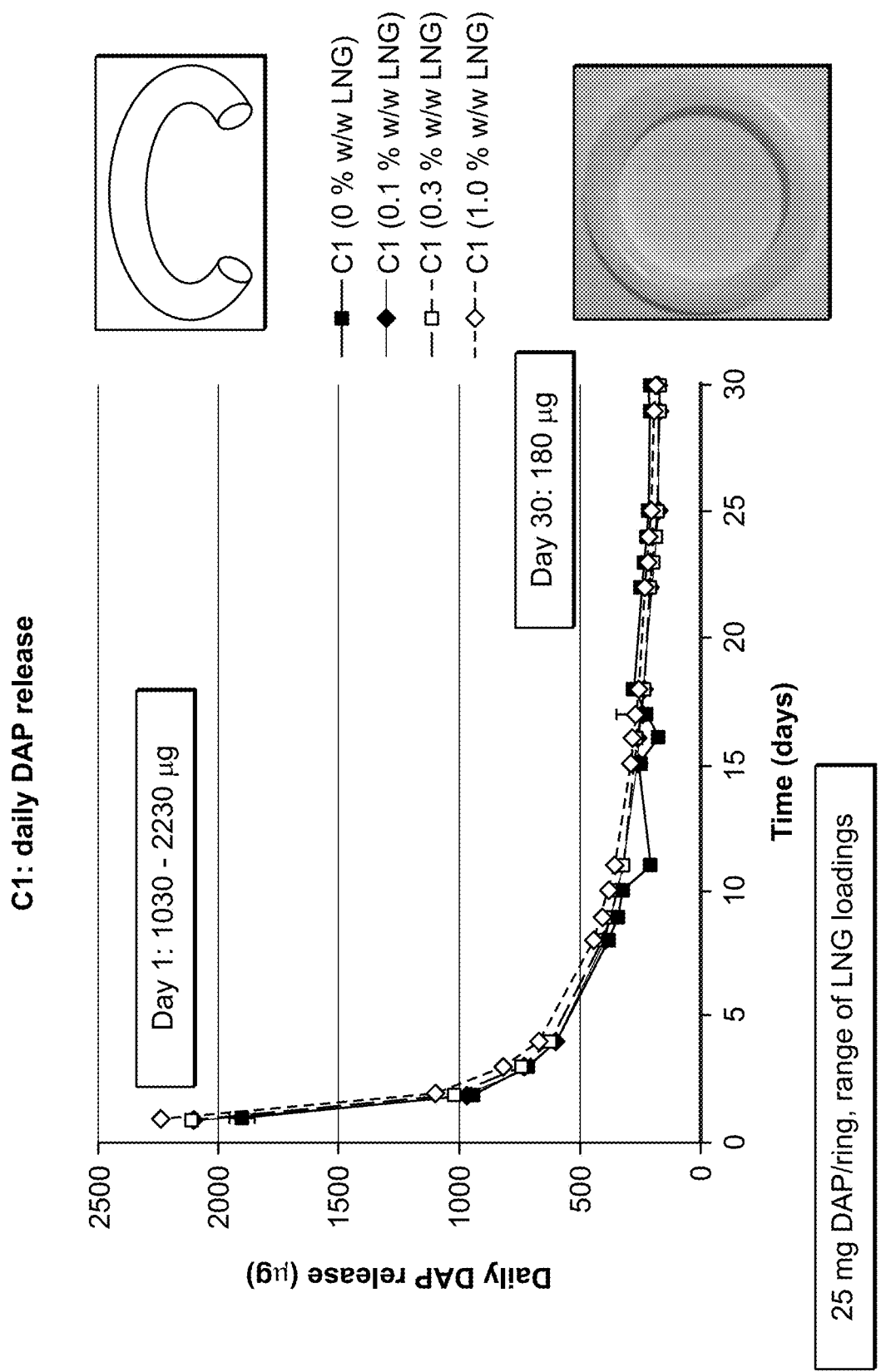
Figure 14B:
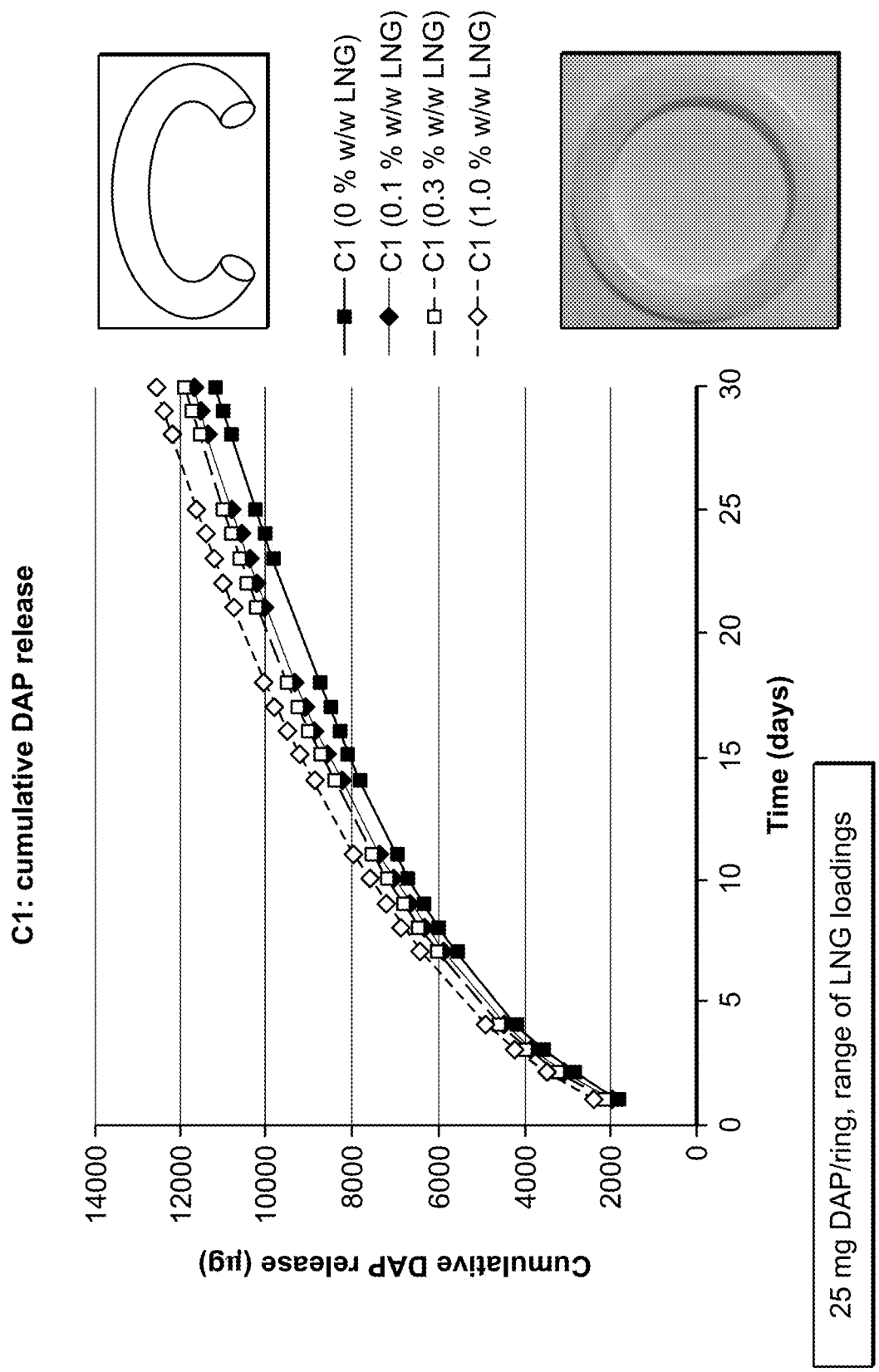
Figure 14D:
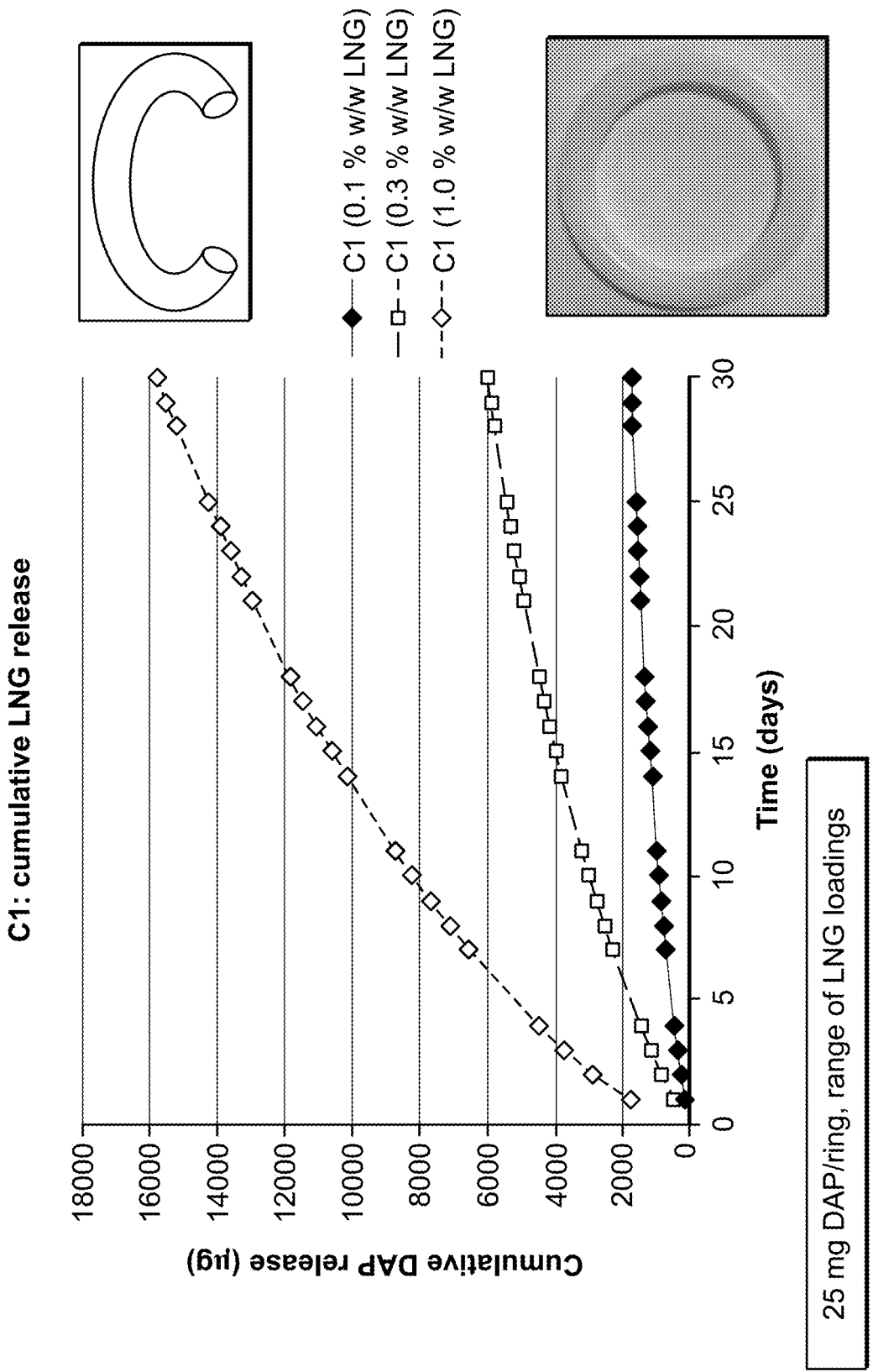
Figure 15A:
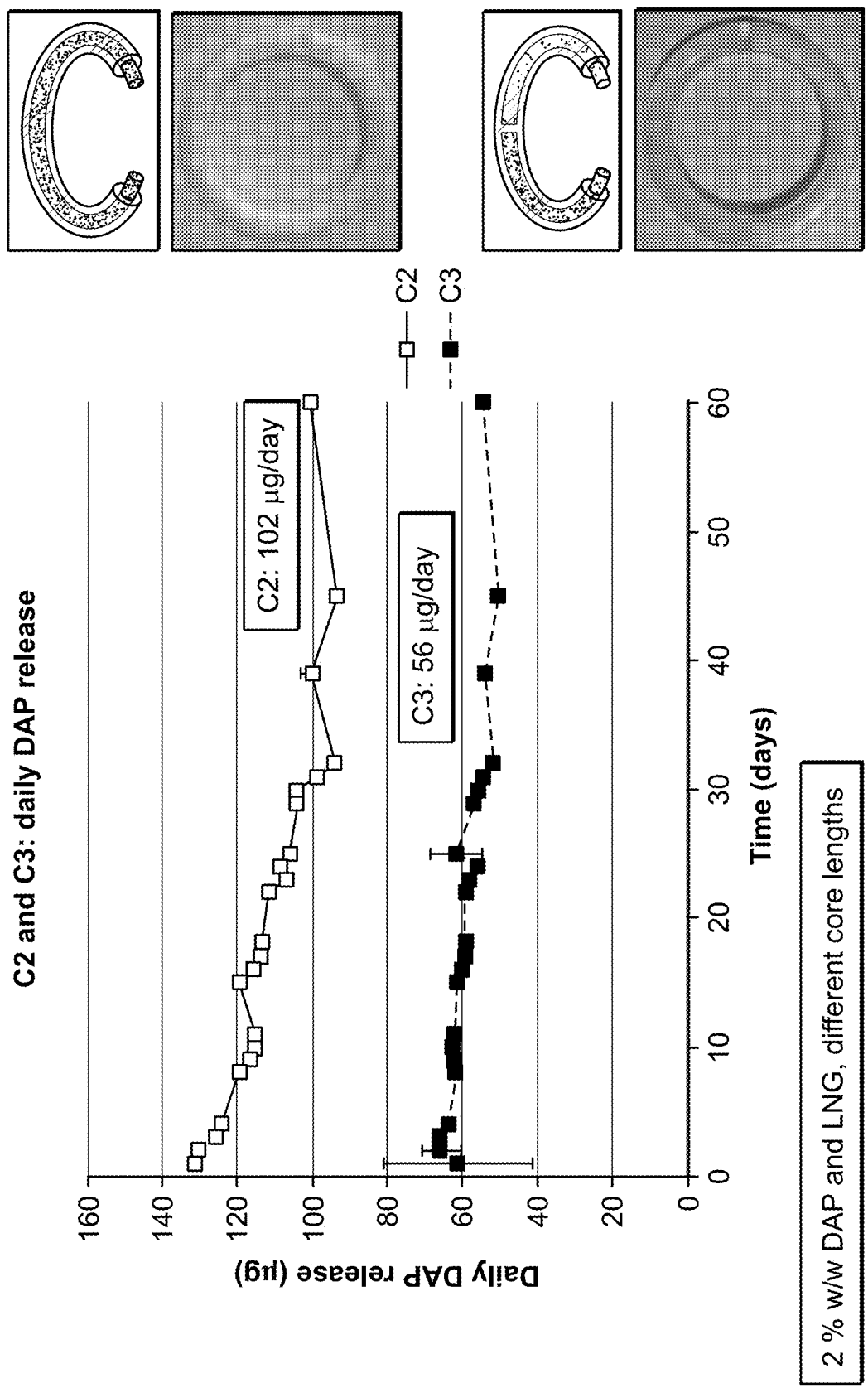
FIG. 15A, FIG. 15B, FIG. 15C, and FIG. 15D depict (FIG. 15A) daily dapivirine release, (FIG. 15B) cumulative dapivirine release, (FIG. 15C) daily LNG release, and (FIG. 15D) cumulative LNG release from ring types C2 (reservoir-type ring with both DAP and LNG loaded in the core, surrounded by a blank sheath), and C3 (reservoir-type ring with DAP and LNG each loaded in separate half-cores, surrounded by a blank sheath).
Figure 15B:
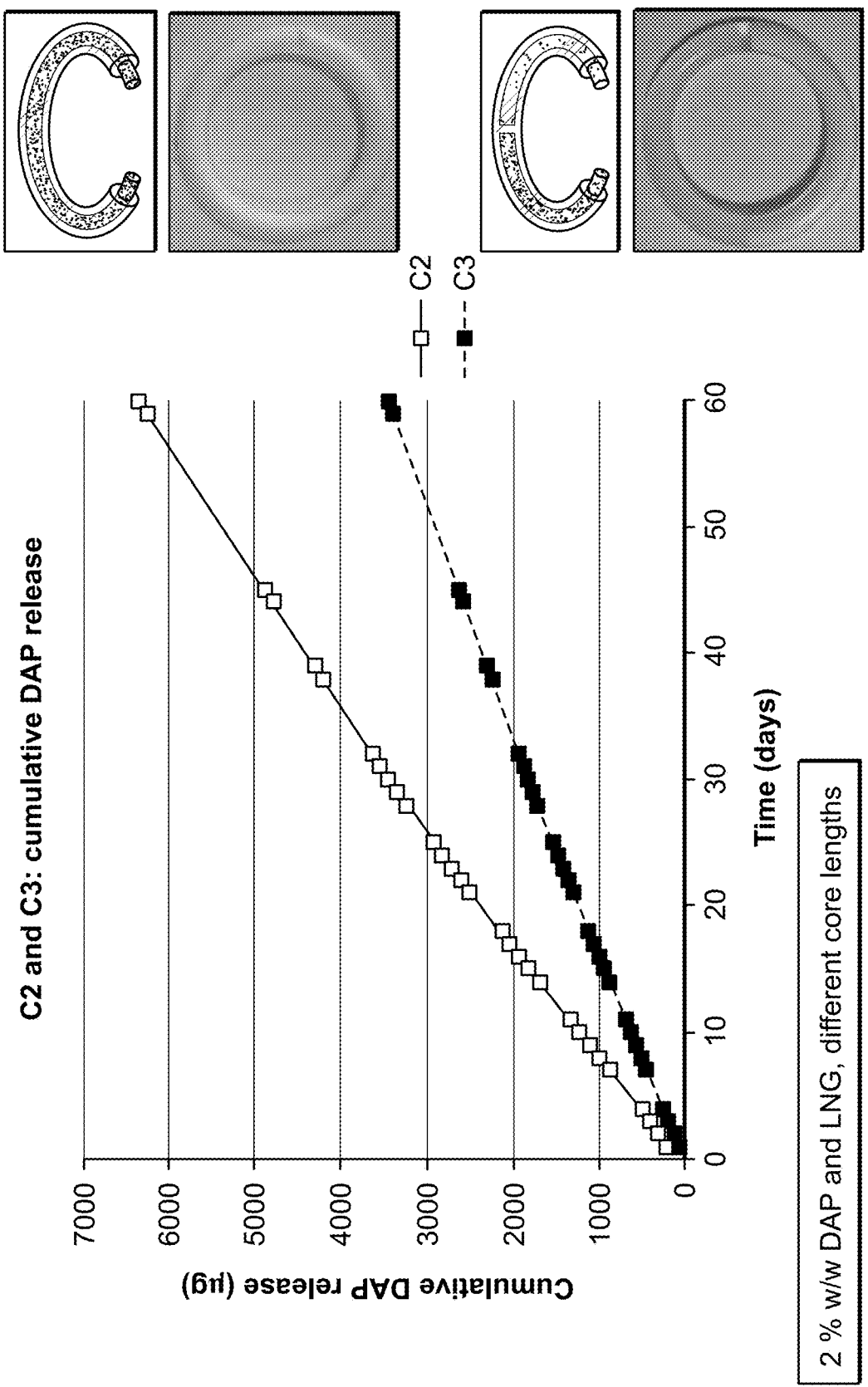
Figure 15C:
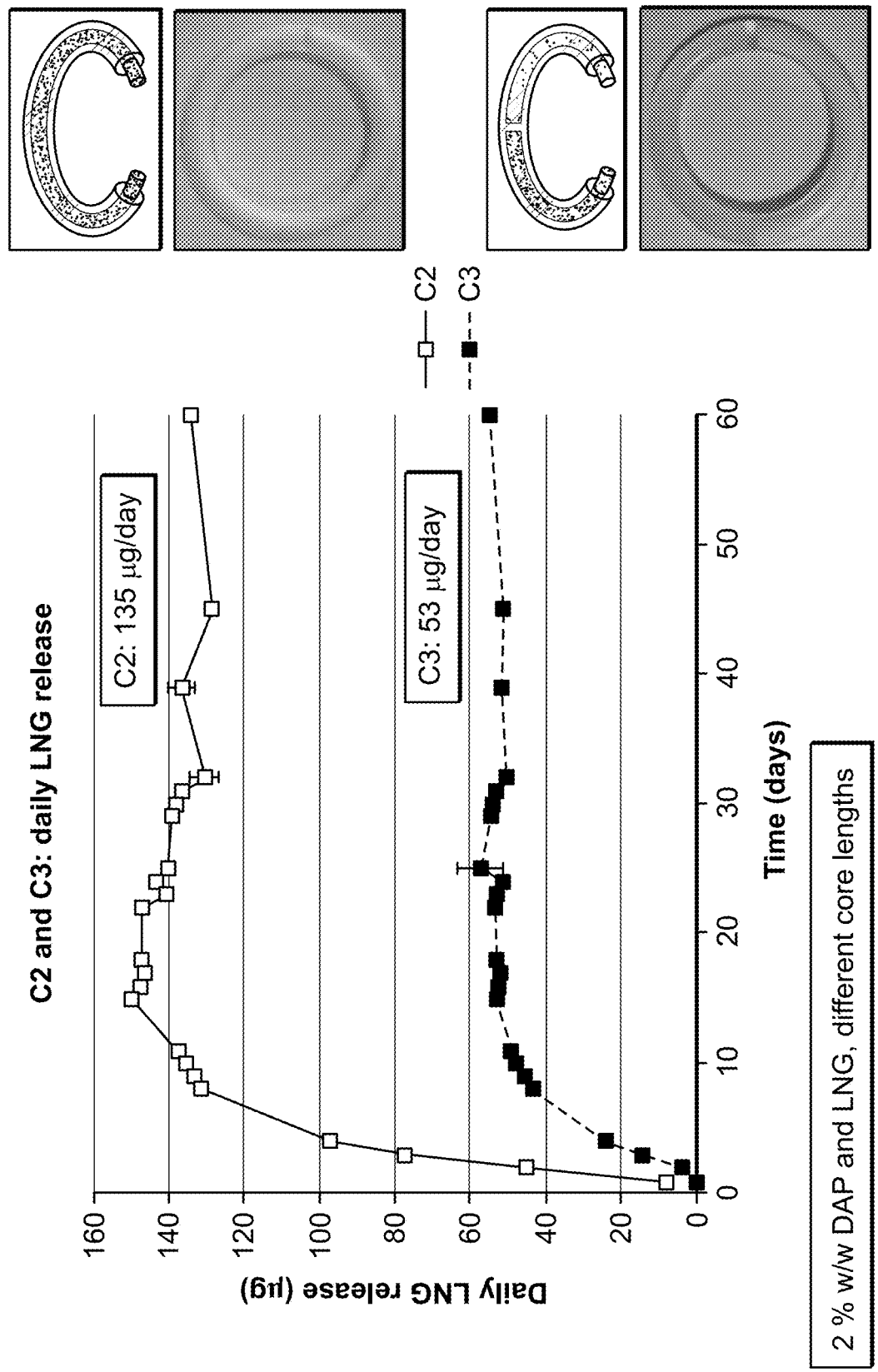
Figure 15D:
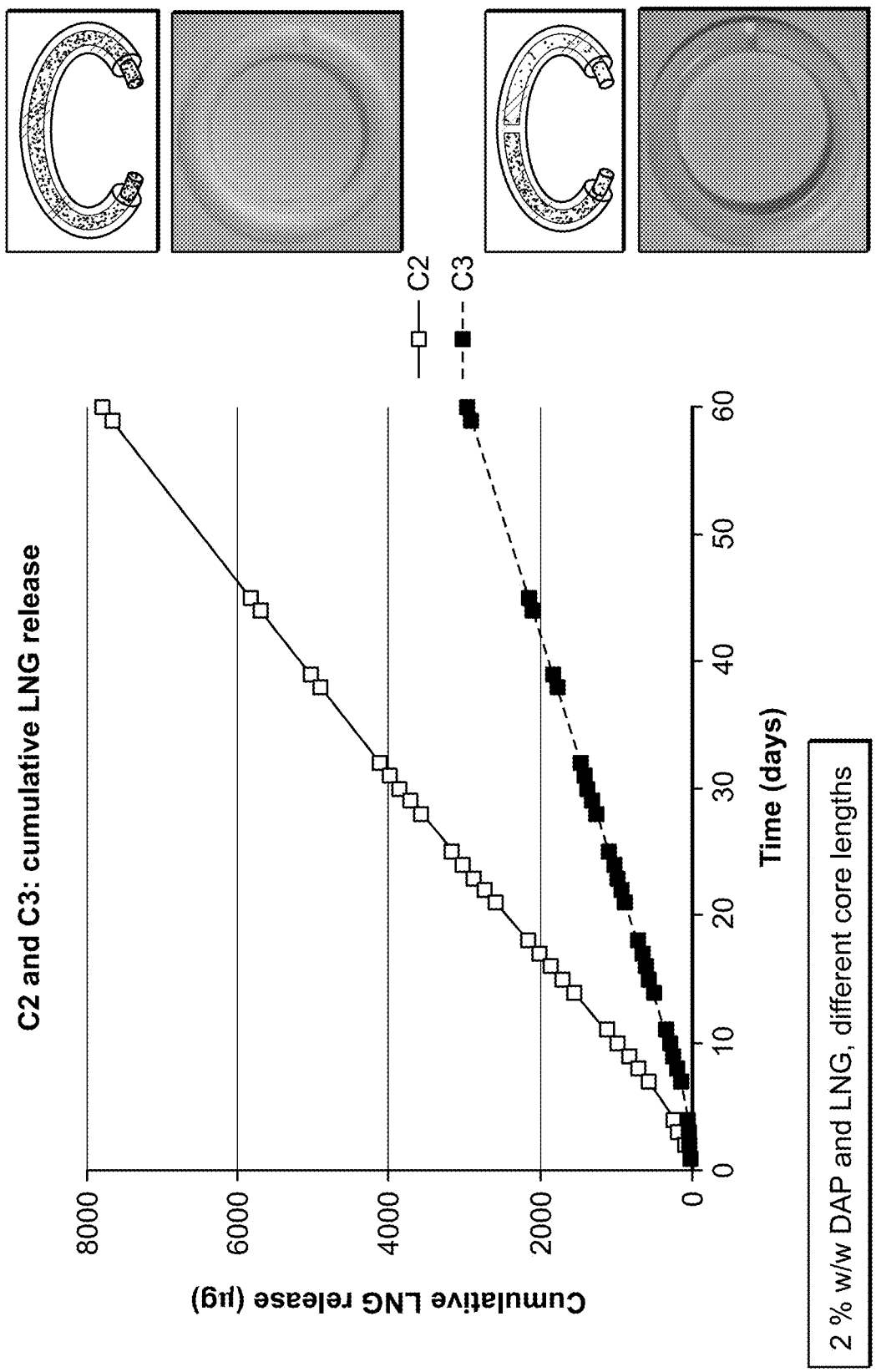

As used herein, the term "reservoir ring" refers to an intravaginal ring comprising a reservoir (a full or partial-length core), which is completely surrounded by a sheath. In one embodiment, both dapivirine and an antimicrobial compound or a contraceptive compound are present in the core of a reservoir ring, with a blank sheath. In another embodiment, dapivirine and either an antimicrobial compound or a contraceptive are present in separate half-cores (or partial cores) of a reservoir ring, with a blank sheath. In yet another embodiment, either the antimicrobial compound or the contraceptive is present in the core of a reservoir ring, and the dapivirine is present in the sheath. Different types of reservoir ring configurations are depicted in FIG. 13. The release of drug substances from such rings is dependent upon permeation (i.e., molecular dissolution and subsequent diffusion) of the core-loaded drug substance through the outer sheath. Release rates can be modified by changing the nature or thickness of the rate-controlling sheath. Reservoir rings were developed to provide controlled (that is, constant daily) release rates.

As used herein, the term "platinum-catalyzed" refers to an intravaginal ring whose cross-linking reaction has been catalyzed using an organo-platinum compound. In one embodiment, the intravaginal ring comprises a silicone elastomer. In yet another embodiment, the intravaginal ring comprises a silicone elastomer and a silicone dispersant. The intravaginal ring may comprise other pharmaceutically compatible agents. Such agents include pharmacologically active agents, as well as, pharmacologically inactive agents known in the art as pharmaceutical excipients.

Various aspects of the invention are described in further detail in the following subsections:

I. Intravaginal Rings

The present invention provides combination therapy intravaginal drug delivery devices, i.e., intravaginal rings, useful for the administration of therapeutic and/or prophylactic agents to a human. The intravaginal rings of the invention may provide long-term controlled release of dapivirine and an antimicrobial agent, such as maraviroc, DS003, darunavir, GSK1265744 or BMS-663068, or dapivirine and a contraceptive, such as levonorgestrel, estradiol, etonorgestrel or nestorone. Surprisingly, the combination of dapivirine and either an antimicrobial compound or a contraceptive in the intravaginal rings of the invention results in the formation of a eutectic composition and provides increased release rates as compared to previous intravaginal rings.

As used herein, the term "intravaginal ring" or "vaginal ring" refers to a doughnut-shaped polymeric drug delivery device which is designed to be inserted into the vagina of a female human in order to provide controlled release of drugs to the vagina over an extended period of time. Several single-indication intravaginal rings are currently available, including Estring® and Femring®, for the treatment of urogenital symptoms of post-menopause, and NuvaRing®, a contraceptive vaginal ring. Intravaginal rings are described in U.S. Pat. No. 6,951,654, U.S. Patent Application Publication Nos. US2007/0043332 and US2009/0004246, PCT Publication Nos. WO99/50250, WO02/076426 and WO03/094920, the entire contents of each of which are expressly incorporated herein by reference.

The intravaginal rings of the instant invention provide controlled release of dapivirine in combination with either an antimicrobial compound or a contraceptive, and may have any shape and be of any dimensions compatible with intravaginal administration to a female human. Such a ring can be self-inserted into the vagina, where it is held in place due to its shape and inherent elasticity. In one embodiment, the intravaginal ring has an outer diameter of 56 mm. In another embodiment, the intravaginal ring has an outer diameter of about 50 mm, about 51 mm, about 52 mm, about 53 mm, about 54 mm, about 55 mm, about 56 mm, about 57 mm, about 58 mm, about 59 mm or about 60 mm. In another embodiment, the intravaginal ring has a cross-sectional diameter of 7.7 mm. In yet another embodiment, the intravaginal ring has a cross-sectional diameter of about 7.0 mm, about 7.1 mm, about 7.2 mm, about 7.3 mm, about 7.4 mm, about 7.5 mm, about 7.6 mm, about 7.7 mm, about 7.8 mm, about 7.9 mm, about 8.0 mm, about 8.1 mm, about 8.2 mm, about 8.3 mm, about 8.4 mm, or about 8.5 mm.

Such an intravaginal ring permits single intravaginal dosing of dapivirine and either an antimicrobial agent or a contraceptive, with a stable release profile. In addition, a device that can be applied less frequently is likely be more acceptable and to achieve better adherence relative to gels that need to be used more frequently In one embodiment, the intravaginal ring comprises a silicone elastomer. In yet another embodiment, the intravaginal ring comprises a silicone elastomer and a silicone dispersant. In another embodiment, the intravaginal ring comprises a polyurethane thermoplastic polymer or an EVA polymer.

The intravaginal ring may comprise other pharmaceutically compatible agents. Such agents include pharmacologically active agents, as well as, pharmacologically inactive agents known in the art as pharmaceutical excipients. Examples of pharmacologically active agents that may be advantageous include, but are not limited to, a local anesthetic such as lidocaine or a local analgesic or a mixture thereof. Examples of pharmacologically inactive agents that may be advantageous include, but are not limited to, a buffer (or buffers), or hydrophilic compounds that enhance the rate of release of the agent from the device, such as for example, polyvinylpyrrolidone (PVP or povidone), modified cellulose ethers (e.g., hydroxyethylcellulose, hydroxypropylcellulose and hydroxypropylmethylcellulose) microcrystalline cellulose, polyacrylic acid, carbomer, alginic acid, carrageenan, cyclodextrins, dextrin, guar gum, gelatin, xanthan gum and sugars (e.g., monosaccharides such as glucose, fructose and galactose, and dissaccharides such as lactose, maltose and fructose). When employed, the release rate enhancing excipient is generally present in an amount of about 0.5 to about 40 w/w % and preferably about 2.5 to about 15 w/w % of the device.

As used herein, the term "matrix ring" or "matrix-type ring" refers to an intravaginal ring in which dapivirine and either an antimicrobial agent or a contraceptive are homogenously distributed throughout the ring. Matrix rings are typically manufactured by injection molding or extrusion of the active compound-containing active mix, leading to the uniform distribution of the active compounds throughout the ring. The matrix-type rings of the instant invention may comprise dapivirine and either an antimicrobial compound or a contraceptive dispersed in silicone elastomer with normal propylorthosilicate (NPOS) crosslinker. This active mix is subsequently cured using a catalyst, such as platinum (with curing achieved by an addition reaction). Matrix-type rings may alternatively comprise a polyurethane or EVA polymer.

As used herein, the term "reservoir ring" refers to an intravaginal ring comprising a reservoir (a full or partial-length core), which is completely surrounded by a sheath. In one embodiment, both dapivirine and an antimicrobial compound or a contraceptive compound are present in the core of a reservoir ring, with a blank sheath. In another embodiment, dapivirine and either an antimicrobial compound or a contraceptive are present in separate half-cores of a reservoir ring, with a blank sheath. In yet another embodiment, either the antimicrobial compound or the contraceptive is present in the core of a reservoir ring, and the dapivirine is present in the sheath. Examples of different types of reservoir-type rings are depicted in FIG. 13. The release of drug substances from such rings is dependent upon permeation (i.e., molecular dissolution and subsequent diffusion) of the core-loaded drug substance through the outer sheath. Release rates can be modified by changing the nature or thickness of the rate-controlling sheath. Reservoir rings were developed to provide controlled (that is, constant daily) release rates.

As used herein, the term "elastomer" refers to an amorphous, or predominantly amorphous, polymer network formed when a polymer or a mixture of polymers undergo cross-linking. Each polymer is comprised of monomeric units, which are linked together to form the network. The monomeric units can comprise carbon, hydrogen, oxygen, silicon, halogen, or a combination thereof.

In some embodiments, the intravaginal ring comprises a polysiloxane. As used herein, a "polysiloxane" refers to any of various compounds containing alternate silicon and oxygen atoms in either a linear or cyclic arrangement usually with one or two organic groups attached to each silicon atom. For example, polysiloxanes include substituted polysiloxanes, and diorganopolysiloxanes such as diarylpolysiloxanes and dialkylpolysiloxanes; an example of the latter is dimethylpolysiloxane. Such dimethylpolysiloxane polymers can be thermoset to the corresponding elastomer by vulcanization with peroxide curing catalysts, e.g., benzoyl peroxide or di-p-chlorobenzoyl peroxide at temperatures of about 200° C. and requiring additional heat after treatment as described in U.S. Pat. Nos. 2,541,137; 2,723,966; 2,863,846; 2,890,188; and 3,022,951, the entire contents of each of which are expressly incorporated herein by reference.

An example of a two-component silicone elastomer, which is platinum-catalyzed at room temperature or under slightly elevated temperature and capable of cross-linking, is MED-4870 (NuSil Technology LLC, Carpinteria, Calif.). In some embodiments of the present invention, an intravaginal ring can comprise silicone liquid (NuSil MED360) as a dispersing agent, and NuSil MED-4870 elastomer. The MED-4870 elastomer is composed of two parts, part A and part B. The chemical composition of MED-4870 part A comprises vinyl terminated polydimethylsiloxane (linear) polymers, platinum-siloxane complex as the catalyst for the cross-linking reaction, and ~30% amorphous (non crystalline) reinforcing silica as a filler. The chemical composition of MED-4870 part B comprises vinyl-terminated polydimethylsiloxane (linear) polymers, hydride functional polydimethysiloxane polymer as a cross-linker, and ~30% amorphous (non-crystalline) reinforcing silica as a filler. Form A and form B undergo cross-linking to form a silicone elastomer.

In some embodiments of the present invention, the polysiloxane elastomer is a diorganopolysiloxane elastomer. In some embodiments, the diorganopolysiloxane elastomer is dimethylpolysiloxane elastomer. In some embodiments, the dimethylpolysiloxane elastomer further comprises a dimethylmethylhydrogen polysiloxane cross-link. In some embodiments of the present invention, the polysiloxane elastomer is MED-4870.

In some embodiments, the polysiloxane elastomer is present in a concentration of about 90% to about 99% by total weight of the ring. In some embodiments, the polysiloxane elastomer is present in a concentration of about 95% by total weight of the ring, or about 97% by total weight of the ring.

Suitable cross-linking agents and curing catalysts are well known in the art. Curing temperatures and times will vary, depending on the particular elastomer(s) used. For example, the curing temperature may vary between room temperature (15-25° C.) and 160° C. but is preferably within the range 60-200° C. The curing time may vary between a few seconds and several hours, depending on the elastomer(s) used. Preferred and suitable elastomers include two-component dimethylpolysiloxane compositions using platinum as the curing catalyst and at a curing temperature of from room temperature to an elevated temperature.

As used herein, the term "platinum-catalyzed" refers to an intravaginal ring whose cross-linking reaction has been catalyzed using an organo-platinum compound.

As used herein, the term "alcohol by-product" refers to a volatile by-product of alcohol (including propanol) produced by tin-catalyzed condensation reactions for cross-linking of solid state silicone. Alcohol by-product contributes to an increased rate of migration of antimicrobial compound from within the matrix of an intravaginal ring to the surface, resulting in the undesirable formation of crystalline deposits of antimicrobial compound on the intravaginal ring.

As used herein, the term "crystalline deposits" refers to the undesirable formation of deposits of crystals of dapivirine, the antimicrobial compound or the contraceptive on the surface of the intravaginal ring.

As used herein, the term "release" or "release rate" refers to the amount or concentration of active agent (i.e., dapivirine, or antimicrobial compound or contraceptive) which leaves the intravaginal ring in any defined time period. "Sustained release" or "sustained release rate" refers to release sufficient to provide antimicrobial properties or contraceptive properties over a specific time period. Release rates of dapivirine, the antimicrobial compound and the contraceptive are defined in more detail in the subsections, below. For example, in one embodiment of the invention, the intravaginal rings are designed to provide sustained release of dapivirine and either the antimicrobial compound or the contraceptive. In one embodiment, less than about 7 mg of dapivirine is released in vitro during an initial 24 hour period of release. In a preferred embodiment of the invention, between about 1 mg and about 3 mg of dapivirine is released in vitro during an initial 24 hour period of release. In one embodiment, less than 1 mg of dapivirine is released in vitro each day for 23 days after an initial 7 day period of release.

In one embodiment, about 100 µg to about 700 µg of dapivirine is released in vitro each day for 23 days after an initial 7 day period of release. In another embodiment, about 100 µg, about 125 µg, about 150 µg, about 175 µg, about 200 µg, about 225 µg, about 250 µg, about 275 µg, about 300 µg, about 350 µg, about 400 µg, about 450 µg, about 500 µg, about 550 µg, about 600 µg, about 650 µg, or about 700 µg of dapivirine is released in vitro each day for 23 days after an initial 7 day period of release.

In another embodiment, less than 1 mg of dapivirine is released in vitro each day for 53 days after an initial 7 day period of release. In one embodiment, about 100 µg to about 700 µg of dapivirine is released in vitro each day for 53 days after an initial 7 day period of release. In another embodiment, about 100 µg, about 125 µg, about 150 µg, about 175 µg, about 200 µg, about 225 µg, about 250 µg, about 275 µg, about 300 µg, about 350 µg, about 400 µg, about 450 µg, about 500 µg, about 550 µg, about 600 µg, about 650 µg, or about 700 µg of dapivirine is released in vitro each day for 53 days after an initial 7 day period of release.

In another embodiment, between about 5 µg and about 300 µg of dapivirine is released in vivo per gram of vaginal fluid each day for 24 days after an initial 3 day period of use. In another embodiment, between about 10 µg and about 100 µg of dapivirine is released in vivo per gram of vaginal fluid each day for 24 days after an initial 3 day period of use. In another embodiment, between about 20 µg and about 80 µg of dapivirine is released in vivo per gram of vaginal fluid each day for 24 days after an initial 3 day period of use. In yet another embodiment, about 5 µg, about 10 µg, about 25 µg, about 50 µg, about 75 µg, about 100 µg, about 125 µg, about 150 µg, about 175 µg, about 200 µg, about 225 µg, about 250 µg, about 275 µg, about 300 µg, about 350 µg, about 400 µg, about 450 µg, about 500 µg, or about 600 µg of dapivirine s released in vivo per gram of vaginal fluid each day for 24 days after an initial 3 day period of use.

Values and ranges included and/or intermediate within the ranges set forth herein are also intended to be within the scope of the present disclosure. Ranges having values recited herein as an upper or lower limit are also intended to be within the scope of the present disclosure. Moreover, the amount of dapivirine, antimicrobial compound, or contraceptive released may clearly be varied depending on, for example, the desired dosing level, the particular compound, the release rate effect of excipients used in the device, and the particular elastomeric system employed.

As used herein, the term "initial 24 hour period of use" refers to the first day, or twenty-four hours, of time after the initial use of the intravaginal ring. The initial 24 hour period of use begins when the intravaginal ring is inserted into the vagina of the female human.

As used herein, the term "each day" refers to an individual 24 hour period.

In one embodiment, less than about 2 mg of the antimicrobial compound is released from the ring in vitro during an initial 24 hour period of release. In another embodiment, less than about 1 mg of the antimicrobial compound is released from the ring in vitro during an initial 24 hour period of release.

In one embodiment, the antimicrobial compound is released in vitro at a rate of about 200 µg per day to about 8000 µg per day for about 23 days after an initial 7 day period of release. In another embodiment, the antimicrobial compound is released in vitro at a rate of about 200 µg per day to about 8000 µg per day for about 53 days after the initial 7 day period of release. In another embodiment, the antimicrobial compound is released in vitro at a rate of about 200 µg per day to about 2000 µg per day, about 400 µg per day to about 4000 µg per day, about 550 µg per day to about 5500 µg per day, or about 800 µg per day to about 8000 µg per day for about 23 days or about 53 days after the initial 7 day period of release.

In one embodiment, less than about 8000 µg per day of the antimicrobial compound is released in vitro after the initial 7 day period of release for about 23 days or for about 53 days. In another embodiment, less than about 5500 µg per day, 4000 µg per day, or 4000 µg per day of the antimicrobial compound is released in vitro after the initial 7 day period of release for about 23 days or for about 53 days. In one embodiment, at least about 200 µg per day, 400 µg per day, 550 µg per day, or 800 µg per day of the antimicrobial compound is released in vitro after the initial 7 day period of release for about 23 days or about 53 days.

In one embodiment, the antimicrobial compound is released in vitro at a rate of about 200 µg per day to about 2000 µg per day for about 30 days or for about 60 days. In another embodiment, the antimicrobial compound is released in vitro at a rate of about 400 µg per day to about 4000 µg per day for about 30 days or for about 60 days. In one embodiment, the antimicrobial compound is released in vitro at a rate of about 550 µg per day to about 5500 µg per day for about 30 days or for about 60 days. In another embodiment, the antimicrobial compound is released in vitro at a rate of about 800 µg per day to about 800 µg per day for about 30 days or for about 60 days.

In one embodiment, less than about 2 mg of the contraceptive is released from the ring in vitro during an initial 24 hour period of release. In another embodiment, less than about 1 mg of the contraceptive is released from the ring in vitro during an initial 24 hour period of release. In one embodiment, the contraceptive is released in vitro at a rate of about 20 µg per day to about 290 µg per day for about 23 days after an initial 7 day period of release. In another embodiment, the contraceptive is released in vitro at a rate of about 20 µg per day to about 290 µg per day for about 53 days after the initial 7 day period of release. In another embodiment, the contraceptive is released in vitro at a rate of about 35 µg per day to about 70 µg per day for about 23 days after the initial 7 day period of release. In another embodiment, the contraceptive is released in vitro at a rate of about 35 µg per day to about 70 µg per day for about 53 days after the initial 7 day period of release.

In one embodiment, less than about 100 µg per day of the contraceptive is released in vitro after the initial 7 day period of release for about 23 days. In another embodiment, less than about 100 µg per day of the contraceptive is released in vitro after the initial 7 day period of release for about 53 days. In one embodiment, less than about 70 µg per day of the contraceptive is released in vitro after the initial 7 day period of release for about 23 days. In one embodiment, less than about 70 µg per day of the contraceptive is released in vitro after the initial 7 day period of release for about 53 days. In one embodiment, less than about 15 µg per day of the contraceptive is released in vitro after the initial 7 day period of release for about 23 days. In one embodiment, less than about 15 µg per day of the contraceptive is released in vitro after the initial 7 day period of release for about 53 days. In one embodiment, about 35 µg per day of the contraceptive is released in vitro after the initial 7 day period of release for about 23 days or for about 53 days.

In one embodiment, the contraceptive is released in vitro at a rate of about 20 μg per day to about 290 μg per day for about 30 days. In another embodiment, the contraceptive is released in vitro at a rate of about 20 μg per day to about 290 μg per day for about 60 days. In one embodiment, the contraceptive is released in vitro at a rate of about 35 μg per day to about 70 μg per day for about 30 days. In another embodiment, the contraceptive is released in vitro at a rate of about 35 μg per day to about 70 μg per day for about 60 days.

In one embodiment, the contraceptive is released in vitro at a rate of less than about 100 μg per day for about 30 days. In another embodiment, the contraceptive is released in vitro at a rate of less than about 100 μg per day for about 60 days. In one embodiment, the contraceptive is released in vitro at a rate of less than about 70 μg per day for about 30 days. In another embodiment, the contraceptive is released in vitro at a rate of less than about 70 μg per day for about 60 days. In one embodiment, the contraceptive is released in vitro at a rate of less than about 35 μg per day for about 30 days. In another embodiment, the contraceptive is released in vitro at a rate of less than about 35 μg per day for about 60 days. In one embodiment, the contraceptive is released in vitro at a rate of less than about 15 μg per day for about 30 days. In another embodiment, the contraceptive is released in vitro at a rate of less than about 15 μg per day for about 60 days.

As used herein, the term "homogenously dispersed throughout" refers to a compound which is uniformly distributed throughout the intravaginal ring.

As used herein, the term "prophylactically effective amount" refers to the amount of antimicrobial compound effective to prevent development of disease in the subject. In one embodiment of the invention, the disease is HIV. In a preferred embodiment of the invention, a prophylactically effective amount is achieved when between about 1 mg and about 3 mg of dapivirine and/or antimicrobial compound is released in vitro during an initial 24 hour period of release. In one embodiment of the invention, a prophylactically effective amount is achieved when between about 100 μg to about 700 μg of dapivirine and/or antimicrobial compound is released in vitro per day after the initial 7 day period of release. In another embodiment, a prophylactically effective amount is achieved when between about 100 μg to about 500 μg of dapivirine and/or antimicrobial compound is released in vitro per day after the initial 7 day period of release. In one embodiment of the invention, a prophylactically effective amount is achieved when between about 200 μg to about 400 μg of dapivirine and/or antimicrobial compound is released in vitro per day after the initial 7 day period of release. In another embodiment of the invention, a prophylactically effective amount is achieved when between about 250 μg to about 350 μg of dapivirine and/or antimicrobial compound is released in vitro per day after the initial 7 day period of release. In another embodiment of the invention, a prophylactically effective amount is achieved when between about 300 μg to about 400 μg of dapivirine and/or antimicrobial compound is released in vitro per day after the initial 7 day period of release. In one embodiment, a prophylactically effective amount is achieved when about 50 μg, about 100 μg, about 125 μg, about 150 μg, about 175 μg, about 200 μg, about 225 μg, about 250 μg, about 275 μg, about 300 μg, about 325 μg, about 350 μg, about 375 μg, about 400 μg, about 450 μg, about 475 μg, about 500 μg, about 550 μg, about 600 μg, about 650 μg, about 700 μg, about 750 μg, about 800 μg, about 850 μg, about 900 μg about 950 μg, about 1 mg, less than about 1 mg or more than about 1 mg of dapivirine and/or antimicrobial compound is released in vitro per day after the initial 7 day period of release.

In another embodiment, a prophylactically effective amount is achieved when between about 5 μg and about 300 μg of dapivirine and/or antimicrobial compound is released in vivo per gram of vaginal fluid each day for 24 days after an initial 3 day period of use. In another embodiment, a prophylactically effective amount is achieved when between about 10 μg and about 100 μg of dapivirine and/or antimicrobial compound is released in vivo per gram of vaginal fluid each day for 24 days after an initial 3 day period of use. In another embodiment, a prophylactically effective amount is achieved when between about 20 μg and about 80 μg of dapivirine and/or antimicrobial compound is released in vivo per gram of vaginal fluid each day for 24 days after an initial 3 day period of use. In yet another embodiment, a prophylactically effective amount is achieved when about 5 μg, about 10 μg, about 25 μg, about 50 μg, about 75 μg, about 100 μg, about 125 μg, about 150 μg, about 175 μg, about 200 μg, about 225 μg, about 250 μg, about 275 μg, about 300 μg, about 350 μg, about 400 μg, about 450 μg, about 500 μg, or about 600 μg of dapivirine and/or antimicrobial compound is released in vivo per gram of vaginal fluid each day for 24 days after an initial 3 day period of use.

Values and ranges included and/or intermediate within the ranges set forth herein are also intended to be within the scope of the present disclosure. Ranges having values recited herein as an upper or lower limit are also intended to be within the scope of the present disclosure.

As used herein, the term "therapeutically effective amount" refers to the amount of compound effective to treat disease in the subject. In one embodiment of the invention, the disease is HIV. In a preferred embodiment of the invention, a therapeutically effective amount is achieved when less than about 7 mg of dapivirine and/or antimicrobial compound is released in vitro during an initial 24 hour period of use. In one embodiment, a therapeutically effective amount is achieved when between about 1 mg and about 3 mg of dapivirine and/or antimicrobial compound is released in vitro during an initial 24 hour period of release. In one embodiment of the invention, a therapeutically effective amount is achieved when between about 100 μg to about 700 μg of dapivirine and/or antimicrobial compound is released in vitro per day after the initial 7 day period of release. In one embodiment of the invention, a therapeutically effective amount is achieved when between about 200 μg to about 400 μg of dapivirine and/or antimicrobial compound is released in vitro per day after the initial 7 day period of release. In another embodiment of the invention, a therapeutically effective amount is achieved when between about 250 μg to about 350 μg of dapivirine and/or antimicrobial compound is released in vitro per day after the initial 7 day period of release. In another embodiment of the invention, a therapeutically effective amount is achieved when between about 180 μg to about 600 μg of dapivirine and/or antimicrobial compound is released in vitro per day after the initial 7 day period of release. In one embodiment, a therapeutically effective amount is achieved when about 100 μg, about 125 μg, about 150 μg, about 175 μg, about 180 μg, about 200 μg, about 225 μg, about 250 μg, about 275 μg, about 300 μg, about 325 μg, about 350 μg, about 375 μg, about 400 μg, about 450 μg, about 475 μg, about 500 μg, about 550 μg, about 600 μg, about 650 μg, or about 700 μg of dapivirine and/or antimicrobial compound is released in vitro per day after the initial 7 day period of release.

In another embodiment, a therapeutically effective amount is achieved when between about 5 μg and about 300 μg of dapivirine and/or antimicrobial compound is released in vivo per gram of vaginal fluid each day for 24 days after an initial 3 day period of use. In another embodiment, a therapeutically effective amount is achieved when between about 10 μg and about 100 μg of dapivirine and/or antimicrobial compound is released in vivo per gram of vaginal fluid each day for 24 days after an initial 3 day period of use. In another embodiment, a therapeutically effective amount is achieved when between about 20 μg and about 80 μg of dapivirine and/or antimicrobial compound is released in vivo per gram of vaginal fluid each day for 24 days after an initial 3 day period of use. In yet another embodiment, a therapeutically effective amount is achieved when about 5 μg, about 10 μg, about 25 μg, about 50 μg, about 75 μg, about 100 μg, about 125 μg, about 150 μg, about 175 μg, about 200 μg, about 225 μg, about 250 μg, about 275 μg, about 300 μg, about 350 μg, about 400 μg, about 450 μg, about 500 μg, or about 600 μg of dapivirine and/or antimicrobial compound is released in vivo per gram of vaginal fluid each day for 24 days after an initial 3 day period of use.

Values and ranges included and/or intermediate within the ranges set forth herein are also intended to be within the scope of the present disclosure. Ranges having values recited herein as an upper or lower limit are also intended to be within the scope of the present disclosure.

As used herein, the term "controlled release rate" refers to a constant release rate that can be determined by the design and drug loading of the vaginal ring.

As used herein, the term "constant release rate" refers to a release rate which does not readily change with device storage over time. Preferably, the release rate of dapivirine, the antimicrobial compound or the contraceptive from the intravaginal ring is constant, or stable and does not readily change over time at room temperature (about 30° C.) or at 40° C. for at least 1 month, at about 2-8° C. for at least 1 year, or for at least 2 years. For example, the release rate of dapivirine, the antimicrobial compound or the contraceptive from the intravaginal rings of the instant invention can be stable for 1, 2, 3, 4, 5, 6, 7, 8, 9, 10, 11, 12, 13, 14, 15, 16, 17, 18, 19, 20, 21, 22, 23, 24, 30, 36, 42 or 48 months.

As used herein, the term "steady release rate" means a release rate that shows relatively little change over time.

A "stable" compound is one which essentially retains its physical stability and/or chemical stability and/or biological activity during the manufacturing process and/or upon storage. Various analytical techniques for measuring stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993).

As used herein, the term "storage" refers to the period of time after which the intravaginal rings are made, but before which the intravaginal rings are used. For example, the intravaginal rings of the instant invention can be stored for 1, 2, 3, 4, 5, 6, 7, 8, 9, 10, 11, 12, 13, 14, 15, 16, 17, 18, 19, 20, 21, 22, 23, 24, 30, 36, 42 or 48 months.

II. Dapivirine

The instant invention is based on the surprising discovery that intravaginal rings comprising dapivirine and either an antimicrobial compound or a contraceptive result in a synergetic composition with enhanced release rates of either the antimicrobial compound, the contraceptive, or dapivirine, as compared to release rates of the compounds, alone. As used herein, the term "dapivirine" refers to (4-[[4-[(2,4,6-trimethylphenyl)amino]-2-pyrimidinyl]amino]benzonitrile), a non-nucleoside reverse transcriptase inhibitor (see structure, below).

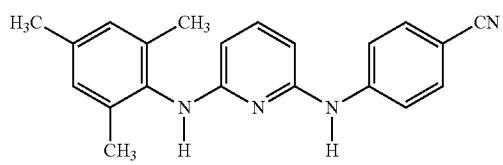 [SMILES: Cc1cc(C)c(Nc2cccc(Nc3ccc(C#N)cc3)n2)c(C)c1]

Dapivirine is useful in the prevention and/or treatment of retroviral infection, such as HIV-1 infection. It is a crystalline compound that is white to slightly beige in color, has a melting point of about 220° C. and is virtually insoluble in water. More specifically, the solubility of dapivirine is less than 0.001 mg/gm of water (i.e., less than 1 μg/ml of water). The intravaginal rings of the instant invention may use micronized dapivirine. A composite result (four samples taken of micronized material) showed that 88.15% of the material had a particle size of less than 5 microns (μM).

Dapivirine was originally developed as an oral antiretroviral compound and was first conceived as an oral therapeutic. Dapivirine has potent activity against wild-type HIV-1 strains and HIV-1 strains harboring different resistance-inducing mutations. (Das et al., *J. Med Chem.,* 2004; 47(10):2550-60.) Dapivirine is a white to off-white or slightly yellow powder, free from visible impurities, has a melting point of approximately 220° C., and is virtually insoluble in water. Dapivirine, a substituted DAPY derivate with the chemical name 4-[[4-[(2,4,6-trimethylphenyl)amino]-2-pyrimidinyl]amino] benzonitrile, is a non-nucleoside reverse transcriptase inhibitor (NNRTI).

In one embodiment, about 10 to about 30 mg of dapivirine is present in the ring. In another embodiment, about 20 mg to about 30 mg of dapivirine is present in the ring. In yet another embodiment, about 10 to about 800 mg, about 50 mg to about 750 mg, about 100 mg to about 700 mg, about 10 mg to about 200 mg, about 10 mg to about 150 mg, about 10 mg to about 100 mg, about 100 mg to about 200 mg, about 150 mg to about 250 mg, about 200 mg to about 600 mg, or about 300 mg to about 400 mg of dapivirine is present in the ring.

In another embodiment, about 15 mg of dapivirine is present in the ring. In another embodiment, about 25 mg of dapivirine is present in the ring. In another embodiment, about 100 mg of dapivirine is present in the ring. In another embodiment, about 150 mg of dapivirine is present in the ring. In another embodiment, about 250 mg of dapivirine is present in the ring. In another embodiment, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 90 mg, about 100 mg, about 125 mg, about 150 mg, about 175 mg, about 200 mg, about 225 mg, about 250 mg, about 275 mg, about 300 mg, about 350 mg, about 400 mg, about 450 mg, about 500 mg, about 550 mg, about 600 mg, about 650 mg, about 700 mg, about 750 mg, or about 800 mg of dapivirine is present in the ring.

In one embodiment, the invention provides intravaginal rings comprising dapivirine and an antimicrobial compound. In another embodiment, the invention provides intravaginal rings comprising dapivirine and a contraceptive. In another embodiment, the invention provides intravaginal rings comprising dapivirine, an antimicrobial compound, and a contraceptive.

The intravaginal rings of the invention may provide long-term controlled release of dapivirine and an antimicrobial agent, such as maraviroc, DS003, darunavir, GSK1265744 or BMS-663068, or dapivirine and a contraceptive, such as levonorgestrel, estradiol, etonorgestrel or nestorone. Surprisingly, the combination of dapivirine and either an antimicrobial compound or a contraceptive in the intravaginal rings of the invention results in the formation of a eutectic composition and provides increased release rates as compared to previous intravaginal rings.

As used herein, the term "eutectic composition" refers to a mixture of chemical compounds that have a single chemical composition that solidifies at a lower temperature than any other composition made up of the same ingredients. The composition is known as the "eutectic composition" and the temperature at which it solidifies is known as the "eutectic temperature." On a phase diagram, the intersection of the eutectic temperature and the eutectic composition gives the "eutectic point." Non-eutectic mixtures will display solidification of one component of the mixture before the other.

In one embodiment of the invention, the combination of dapivirine and an antimicrobial compound, e.g., maraviroc, results in the formation of a eutectic composition and provides increased release rate of the antimicrobial compound as compared to intravaginal rings comprising the antimicrobial compound without dapivirine. In one embodiment of the invention, the combination of dapivirine and an antimicrobial compound, e.g., maraviroc, results in the formation of a eutectic composition and provides increased release rate of dapivirine as compared to intravaginal rings comprising the antimicrobial compound without dapivirine.

In another embodiment of the invention, the combination of dapivirine and a contraceptive, e.g., levonorgestrel, results in the formation of a eutectic composition and provides increased release rate of the contraceptive as compared to intravaginal rings comprising the contraceptive without dapivirine. In one embodiment of the invention, the combination of dapivirine and a contraceptive, e.g., levonorgestrel, results in the formation of a eutectic composition and provides increased release rate of dapivirine as compared to intravaginal rings comprising the contraceptive without dapivirine.

As used herein, the term "release" or "release rate" refers to the amount or concentration of active agent (i.e., dapivirine, or antimicrobial compound or contraceptive) which leaves the intravaginal ring in any defined time period. "Sustained release" or "sustained release rate" refers to release of the active agent sufficient to provide antimicrobial properties or contraceptive properties over a specific time period. For example, in one embodiment of the invention, the intravaginal rings are designed to provide sustained release of dapivirine and either the antimicrobial compound or the contraceptive. In a preferred embodiment of the invention, less than 7 mg of dapivirine is released in vitro during an initial 24 hour period of release. In another embodiment, between about 1 mg and about 3 mg of dapivirine is released in vitro during an initial 24 hour period of release. In one embodiment, less than 1 mg of dapivirine is released in vitro each day for 23 days after an initial 7 day period of release.

As used herein, the term "increased release" or "increased release rate" refers to the release or the release rate of an active agent (e.g., dapivirine, an antimicrobial compound, or a contraceptive) from an intravaginal ring of the invention comprising a combination of dapivirine and either an antimicrobial compound or a contraceptive that is greater, or larger, than the release or the release rate of the active agent (e.g., dapivirine, an antimicrobial compound, or a contraceptive) from an intravaginal ring comprising only one active agent, e.g., dapivirine only, an antimicrobial agent only, or a contraceptive only. Increased release rates can be expressed in terms of increased release per day or cumulative release rate over a period of time, e.g., increased cumulative release over 30 days, over 60 days, or over 90 days. Increased release rates can be expressed in terms of increased release per day after a period of time, e.g., increased cumulative release over 23 days, 53 days or 83 days after an initial 7 day period of release. Increased release rates can also be expressed in terms of increased release per day after a period of time, e.g., increased cumulative release over 29 days, 59 days or 89 days after an initial 24 hour period of release.

In one of the invention, the release rate of the dapivirine from a combination therapy intravaginal ring of the invention (e.g., a ring comprising dapivirine and either an antimicrobial agent, e.g., maraviroc, or a contraceptive, e.g., levonorgestrel) is not increased as compared to the release rate of dapivirine from an intravaginal ring comprising only dapivirine. In one embodiment, the release rate of the antimicrobial compound or the contraceptive is increased from the combination therapy intravaginal ring of the invention as compared to the release rate of the antimicrobial compound or the contraceptive from an intravaginal ring comprising dapivirine without either the antimicrobial compound or the contraceptive.

In another embodiment, the release rate of the dapivirine from a combination therapy intravaginal ring of the invention (e.g., a ring comprising dapivirine and either an antimicrobial agent, e.g., maraviroc, or a contraceptive, e.g., levonorgestrel) is increased as compared to the release rate of dapivirine from an intravaginal ring comprising dapivirine without either the antimicrobial compound or the contraceptive. For example, in one embodiment, the release rate of dapivirine from an intravaginal ring of the invention comprising dapivirine and either an antimicrobial agent or a contraceptive is increased at least about 2-fold per day as compared to the release rate of dapivirine from an intravaginal ring comprising dapivirine without either the antimicrobial agent or the contraceptive. In one embodiment, the release rate of dapivirine from an intravaginal ring of the invention comprising dapivirine and either an antimicrobial agent or a contraceptive is increased at least about 10-fold per day as compared to the release rate of dapivirine from an intravaginal ring comprising dapivirine without either the antimicrobial agent or the contraceptive. In another embodiment, the release rate of dapivirine from an intravaginal ring of the invention comprising dapivirine and either an antimicrobial agent or a contraceptive is increased at least about 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50-fold per day as compared to the release rate of dapivirine from an intravaginal ring comprising dapivirine without either the antimicrobial agent or the contraceptive. In one embodiment, the release rate of dapivirine from an intravaginal ring of the invention comprising dapivirine and either an antimicrobial agent or a contraceptive is increased by about 2-fold to about 50-fold, by about 2-fold to about 25-fold, by about 2-fold to about 20-fold, by about 2-fold to about 15-fold, by about 2-fold to about 10-fold, by about 2-fold to about 5-fold, by about 5-fold to about 25-fold, by about 5-fold to about 20-fold, by about 5-fold to about 15-fold, by about 5-fold to about 10-fold, by about 10-fold to about 25-fold, or by about 1-fold to about 20-fold per day as compared to the release rate of dapivirine from an intravaginal ring comprising dapivirine without either the antimicrobial agent or the contraceptive.

In one embodiment, the cumulative release rate of dapivirine from an intravaginal ring of the invention comprising dapivirine and either an antimicrobial agent or a contraceptive agent is increased at least about 2-fold after 30 days, after 60 days, or after 90 days as compared to the cumulative release rate of dapivirine from an intravaginal ring comprising dapivirine without either the antimicrobial agent or the contraceptive after 30 days, after 60 days, or after 90 days. In one embodiment, the cumulative release rate of dapivirine from an intravaginal ring of the invention comprising dapivirine and either an antimicrobial agent or a contraceptive is increased at least about 10-fold after 30 days, after 60 days, or after 90 days as compared to the cumulative release rate of dapivirine from an intravaginal ring comprising dapivirine without either the antimicrobial agent or the contraceptive after 30 days, after 60 days, or after 90 days. In another embodiment, the cumulative release rate of dapivirine from an intravaginal ring of the invention comprising dapivirine and either an antimicrobial agent or a contraceptive is increased at least about 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50-fold after 30 days, after 60 days, or after 90 days as compared to the cumulative release rate of dapivirine from an intravaginal ring comprising dapivirine without the antimicrobial agent or the contraceptive after 30 days, after 60 days, or after 90 days. In one embodiment, the cumulative release rate of dapivirine from an intravaginal ring of the invention comprising dapivirine and either an antimicrobial agent or a contraceptive is increased by about 2-fold to about 50-fold, by about 2-fold to about 25-fold, by about 2-fold to about 20-fold, by about 2-fold to about 15-fold, by about 2-fold to about 10-fold, by about 2-fold to about 5-fold, by about 5-fold to about 25-fold, by about 5-fold to about 20-fold, by about 5-fold to about 15-fold, by about 5-fold to about 10-fold, by about 10-fold to about 25-fold, or by about 1-fold to about 20-fold after 30 days, after 60 days, or after 90 days as compared to the cumulative release rate of dapivirine from an intravaginal ring comprising dapivirine without the antimicrobial agent or the contraceptive after 30 days, after 60 days, or after 90 days.

Values and ranges included and/or intermediate within the ranges set forth herein are also intended to be within the scope of the present disclosure. Ranges having values recited herein as an upper or lower limit are also intended to be within the scope of the present disclosure.

III. Antimicrobial Compounds

The instant invention is based on the surprising discovery that intravaginal rings comprising dapivirine and an antimicrobial compound result in a synergetic composition with enhanced release rates of either the antimicrobial compound or dapivirine, as compared to release rates of the compounds, alone.

As used herein, the term "antimicrobial compound" or "antimicrobial agent" (used interchangeably herein) refers to a compound or agent which is capable of inhibiting or destroying the growth of a microbial organism. In one embodiment, the antimicrobial compound is a non-nucleoside reverse transcriptase inhibitor ("NNRTI"). In one embodiment, the antimicrobial compound is a viral entry inhibitor. In one embodiment of the invention, the antimicrobial compound is maraviroc. In one embodiment of the invention, the antimicrobial is DS003. In another embodiment of the invention, the antimicrobial compound is darunavir, GSK 1265744 or BMS-663068. The term "antimicrobial compound" is intended to embrace antibacterial agents, antifungal agents, antiprotozoal agents, antiviral agents and mixtures thereof. For purposes of this invention, the term "antimicrobial compound" or "antimicrobial agent" is a compound other than dapivirine. That is, the intravaginal rings of the invention do not contain only dapivirine as the active agent.

In another embodiment of the invention, the antimicrobial compound is a non-nucleoside reverse transcriptase inhibitor ("NNRTI"). In one embodiment, the NNRTI is a substituted di-amino pyrimidine derivative. Useful NNRTI class compounds include, but are not limited to, nevirapine, delavirdine, etravirine and efavirenz. NNRTIs bind to the hydrophobic pocket near the active site of the HIV reverse transcriptase (RT) enzyme, blocking DNA polymerization. (See, e.g., Tarby, *Curr. Top. Med. Chem.*, 2004; 4(10):1045-57, U.S. Patent Application Publication No. US2006/0166943, and PCT Publication No. WO03/094920, the entire contents of each of which are expressly incorporated herein by reference.) This prevents viral replication and, therefore, production of infectious virus. (Borkow et al., *J. Virol.*, 1997; 71(4):3023-30.)

In another preferred embodiment of the invention, the antimicrobial compound is a viral entry inhibitor. In another embodiment, the viral entry inhibitor is maraviroc. In another preferred embodiment of the invention, a nucleoside reverse transcriptase inhibitor is used.

The term "antimicrobial compound" is intended to embrace antibacterial agents, antifungal agents, antiprotozoal agents, antiviral agents and mixtures thereof.

Suitable antibacterial agents include Acrosoxacin, Amifloxacin, Amoxycillin, Ampicillin, Aspoxicillin, Azidocillin, Azithromycin, Aztreonam, Balofloxacin, Benzylpenicillin, Biapenem, Brodimoprim, Cefaclor, Cefadroxil, Cefatrizine, Cefcapene, Cefdinir, Cefetamet, Cefmetazole, Cefprozil, Cefroxadine, Ceftibuten, Cefuroxime, Cephalexin, Cephalonium, Cephaloridine, Cephamandole, Cephazolin, Cephradine, Chlorquinaldol, Chlortetracycline, Ciclacillin, Cinoxacin, Ciprofloxacin, Clarithromycin, Clavulanic Acid, Clindamycin, Clofazimine, Cloxacillin, Danofloxacin, Dapsone, Demeclocycline, Dicloxacillin, Difloxacin, Doxycycline, Enoxacin, Enrofloxacin, Erythromycin, Fleroxacin, Flomoxef, Flucloxacillin, Flumequine, Fosfomycin, Isoniazid, Levofloxacin, Mandelic Acid, Mecillinam, Metronidazole, Minocycline, Mupirocin, Nadifloxacin, Nalidixic Acid, Nifuirtoinol, Nitrofurantoin, Nitroxoline, Norfloxacin, Ofloxacin, Oxytetracycline, Panipenem, Pefloxacin, Phenoxymethylpenicillin, Pipemidic Acid, Piromidic Acid, Pivampicillin, Pivmecillinam, Prulifloxacin, Rufloxacin, Sparfloxacin, Sulbactam, Sulfabenzamide, Sulfacytine, Sulfametopyrazine, Sulphacetamide, Sulphadiazine, Sulphadimidine, Sulphamethizole, Sulphamethoxazole, Sulphanilamide, Sulphasomidine, Sulphathiazole, Temafloxacin, Tetracycline, Tetroxoprim, Tinidazole, Tosufloxacin, Trimethoprim and salts or esters thereof.

Preferred antibacterial agents include tetracyclines such as Doxycycline, Tetracycline or Minocycline; macrolides such as Azithromycin, Clarithromycin and Erythromycin;

nitroimidazoles such as Metronidazole or Tinidazole; quinolones such as Ofloxacin, Norfloxacin, Cinoxacin, Ciprofloxacin and Levofloxacin; Clindamycin and Dapsone.

Suitable antifungal agents include Bifonazole, Butoconazole, Chlordantoin, Chlorphenesin, Ciclopirox Olamine, Clotrimazole, Eberconazole, Econazole, Fluconazole, Flutrimazole, Isoconazole, Itraconazole, Ketoconazole, Miconazole, Nifuroxime, Tioconazole, Terconazole, Undecenoic Acid and salts or esters thereof.

Preferred antifungal agents include Clotrimazole, Econazole, Fluconazole, Itraconazole, Ketoconazole, Miconazole, Terconazole and Tioconazole.

Suitable antiprotozoal agents include Acetarsol, Azanidazole, Chloroquine, Metronidazole, Nifuratel, Nimorazole, Omidazole, Propenidazole, Secnidazole, Sineflngin, Tenonitrozole, Temidazole, Tinidazole and salts or esters thereof.

Metronidazole, Tinidazole and Chloroquine are most preferred antiprotozoal agents.

Suitable antiviral agents include Acyclovir, Brivudine, Cidofovir, Curcumin, Dapirivine, Desciclovir, 1-Docosanol, Edoxudine, Fameyclovir, Fiacitabine, Ibacitabine, Imiquimod, Lamivudine, Penciclovir, Valacyclovir, Valganciclovir and salts or esters thereof. Curcumin, Acyclovir, Famcyclovir, Dapirivine and Valacyclovir are preferred antiviral agents.

The most preferred antimicrobial agents of this invention include, without limitation, Dapirivine, Metronidazole, Acyclovir, Clotrimazole, Fluconazole, Terconazole, Azithromycin, Erythromycin, Doxycycline, Tetracycline, Minocycline, Clindamycin, Famcyclovir, Valacyclovir, Clarithromycin, a prodrug or salt thereof and combinations thereof.

Mixtures of antibacterial agents, mixtures of antifungal agents; mixtures of antiviral agents; mixtures of antiprotozoal agents and mixtures of agents from two or more of these categories are also envisaged by the present invention. In addition, it is also envisaged that the present invention embraces at least one antimicrobial agent (microstatic and/or microcidal agent) with one or more other pharmaceutically active agent.

In one embodiment of the invention, the intravaginal ring comprises dapivirine and one antimicrobial agent. In another embodiment of the invention, the intravaginal ring comprises dapivirine and at least two, at least three, at least four, or at least five antimicrobial agents. In another embodiment of the invention, the intravaginal ring comprises dapivirine, a antimicrobial agent, and a contraceptive.

Antimicrobial compounds contained in the rings of the present invention are further described at least in U.S. Patent Application Publication Nos. 2012/0093911 and 2006/0166943 and PCT Publication Nos. WO99/50250, WO02/076426 and WO03/094920, the entire contents of each of which are expressly incorporated herein by reference. The antimicrobial compounds contained in the rings of the present invention can be prepared according to art-known procedures. In particular, they are prepared according to the procedures described in EP 1002795, WO 99/50250, WO 99/50256 and WO 00/27828, the entire contents of each of which are incorporated herein by reference.

The antimicrobial compounds contained in the rings of the present invention may have microbicidal activity and have the ability to prevent the transmission of HIV. In particular, they can prevent sexual or vaginal transmission of HIV by preventing either the production of infectious viral particles or infection of uninfected cells. If infected cells in sperm can reach the mucosa, the compounds of the present invention can prevent HIV infection of host cells, such as macrophages, lymphocytes, Langerhans and M cells. Thus, these compounds prevent systemic HIV infection of a human being, exhibiting a prophylactic action against HIV.

In one embodiment, about 10 to about 30 mg of antimicrobial agent is present in the ring. In another embodiment, about 20 mg to about 30 mg of antimicrobial agent is present in the ring. In yet another embodiment, about 10 to about 800 mg, about 50 mg to about 750 mg, about 100 mg to about 700 mg, or about 200 mg to about 600 mg, about 300 mg to about 400 mg, or about 100 mg to about 1600 mg of antimicrobial agent is present in the ring.

In another embodiment, about 15 mg, 16 mg, 25 mg, 32 mg, 100 mg, 150 mg or 250 mg of antimicrobial agent is present in the ring. In another embodiment, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 90 mg, about 100 mg, about 125 mg, about 150 mg, about 175 mg, about 200 mg, about 225 mg, about 250 mg, about 275 mg, about 300 mg, about 350 mg, about 400 mg, about 450 mg, about 500 mg, about 550 mg, about 600 mg, about 650 mg, about 700 mg, about 750 mg, about 800 mg, about 900 mg, about 1000 mg, about 1100 mg, about 1200 mg, about 1300 mg, about 1400 mg, about 1500 mg, or about 1600 mg of antimicrobial agent is present in the ring.

Surprisingly, the combination of dapivirine and an antimicrobial compound, e.g., maraviroc, in the intravaginal rings of the invention results in the formation of a eutectic composition and provides an increased release rate of the antimicrobial compound as compared to the release rate of the antimicrobial compound in intravaginal rings comprising the antimicrobial compound without dapivirine. For example, in one embodiment, the release rate of the antimicrobial agent from an intravaginal ring of the invention comprising dapivirine and the antimicrobial agent is increased at least about 2-fold per day as compared to the release rate of the antimicrobial agent from an intravaginal ring comprising the antimicrobial agent without dapivirine. In one embodiment, the release rate of the antimicrobial agent from an intravaginal ring of the invention comprising dapivirine and the antimicrobial agent is increased at least about 10-fold per day as compared to the release rate of the antimicrobial agent from an intravaginal ring comprising the antimicrobial agent without dapivirine. In another embodiment, the release rate of the antimicrobial agent from an intravaginal ring of the invention comprising dapivirine and the antimicrobial agent is increased at least about 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50-fold per day as compared to the release rate of the antimicrobial agent from an intravaginal ring comprising the antimicrobial agent without dapivirine. In one embodiment, the release rate of the antimicrobial agent from an intravaginal ring of the invention comprising dapivirine and the antimicrobial agent is increased by about 2-fold to about 50-fold, by about 2-fold to about 25-fold, by about 2-fold to about 20-fold, by about 2-fold to about 15-fold, by about 2-fold to about 10-fold, by about 2-fold to about 5-fold, by about 5-fold to about 25-fold, by about 5-fold to about 20-fold, by about 5-fold to about 15-fold, by about 5-fold to about 10-fold, by about 10-fold to about 25-fold, or by about 1-fold to about 20-fold per day as compared to the release rate of the antimicrobial agent from an intravaginal ring comprising the antimicrobial agent without dapivirine.

In one embodiment, the cumulative release rate of the antimicrobial agent from an intravaginal ring of the invention comprising dapivirine and the antimicrobial agent is increased at least about 2-fold after 30 days, after 60 days, or after 90 days as compared to the cumulative release rate of the antimicrobial agent from an intravaginal ring comprising the antimicrobial agent without dapivirine after 30 days, after 60 days, or after 90 days. In one embodiment, the cumulative release rate of the antimicrobial agent from an intravaginal ring of the invention comprising dapivirine and the antimicrobial agent is increased at least about 10-fold after 30 days, after 60 days, or after 90 days as compared to the cumulative release rate of the antimicrobial agent from an intravaginal ring comprising the antimicrobial agent without dapivirine after 30 days, after 60 days, or after 90 days. In another embodiment, the cumulative release rate of the antimicrobial agent from an intravaginal ring of the invention comprising dapivirine and the antimicrobial agent is increased at least about 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50-fold after 30 days, after 60 days, or after 90 days as compared to the cumulative release rate of the antimicrobial agent from an intravaginal ring comprising the antimicrobial agent without dapivirine after 30 days, after 60 days, or after 90 days. In one embodiment, the cumulative release rate of the antimicrobial agent from an intravaginal ring of the invention comprising dapivirine and the antimicrobial agent is increased by about 2-fold to about 50-fold, by about 2-fold to about 25-fold, by about 2-fold to about 20-fold, by about 2-fold to about 15-fold, by about 2-fold to about 10-fold, by about 2-fold to about 5-fold, by about 5-fold to about 25-fold, by about 5-fold to about 20-fold, by about 5-fold to about 15-fold, by about 5-fold to about 10-fold, by about 10-fold to about 25-fold, or by about 1-fold to about 20-fold after 30 days, after 60 days, or after 90 days as compared to the cumulative release rate of the antimicrobial agent from an intravaginal ring comprising the antimicrobial agent without dapivirine after 30 days, after 60 days, or after 90 days.

In one embodiment, the release rate of the dapivirine from an intravaginal ring comprising dapivirine and the antimicrobial compound is not increased as compared to the release rate of dapivirine from an intravaginal ring comprising only dapivirine. In another embodiment, the release rate of the dapivirine from an intravaginal ring comprising dapivirine and the antimicrobial compound is also increased as compared to the release rate of dapivirine from an intravaginal ring comprising only dapivirine.

Values and ranges included and/or intermediate within the ranges set forth herein are also intended to be within the scope of the present disclosure. Ranges having values recited herein as an upper or lower limit are also intended to be within the scope of the present disclosure.

IV. Contraceptives

The instant invention is based on the surprising discovery that intravaginal rings comprising dapivirine and a contraceptive result in a synergetic composition with enhanced release rates of either the contraceptive or dapivirine, as compared to release rates of the compounds, alone.

As used herein, the term "contraceptive" refers to an active agent that prevents conception or pregnancy. Contraceptives are well-known in the art and include, but are not limited to, steroid hormones and include, for example, an estrogen, a progestin, a progesterone, a testosterone, derivatives thereof, or combinations thereof. Examples of contraceptives include 17a-ethinyl-levonorgestrel-17b-hydroxy-estra-4,9,11-trien-3-one, estradiol, etonogestrel, levonorgestrel, medroxyprogesterone acetate, nestorone, norethindrone, and progesterone. In one embodiment of the invention, the contraceptive is levonorgestrel. In one embodiment of the invention, the contraceptive is estradiol. In one embodiment of the invention, the contraceptive is etonogestrel. In one embodiment of the invention, the contraceptive is nestorone.

As used herein, an "estrogen" refers to any of various natural or synthetic compounds that stimulate the development of female secondary sex characteristics and promote the growth and maintenance of the female reproductive system, or any other compound that mimics the physiological effect of natural estrogens. Estrogens suitable for use with the present invention also include compounds that can be converted to active estrogenic compounds. For example, in some embodiments, a conjugated estrogen can be administered from an intravaginal device of the present invention. As used herein, the term "conjugated" refers to the sulfate ester, glucuronide ester, or mixed sulfate-glucuronide esters, of an estrogen. Estrogens suitable for use with the present invention also include pharmaceutically suitable salt forms of estrogens. In some embodiments, the salt can be a sodium, potassium, or 2-amino-2-(hydroxymethyl)-1,3-propanediol (Tris) salt. An estrogen suitable for use with the present invention can be useful as a contraceptive agent.

Estrogens suitable for use in the present invention include, but are not limited to, natural and synthetic compounds having estrogenic activity, such as, for example, estradiol (17β-estradiol), 17α-estradiol, estriol, estrone, and their esters, such as the acetate, sulfate, valerate or benzoate esters of these compounds, including, for example, estradiol 17β-cypionate, estradiol 17-propionate, estradiol 3-benzoate, and piperazine estrone sulfate; ethinyl estradiol; conjugated estrogens (natural and synthetic); agonistic anti-estrogens; and selective estrogen receptor modulators.

Prodrugs of suitable estrogens can also be used in the device of the present invention. As used herein, a "prodrug" denotes a derivative of a known direct acting drug, which derivative has enhanced delivery characteristics and therapeutic value as compared to the drug and is transformed into the active drug by an enzymatic or chemical process. Examples of estrogen prodrugs include, but are not limited to, estradiol acetate (which is converted in vivo to 17β-estradiol) and mestranol (which is converted in vivo to ethinyl estradiol). In some embodiments, the estrogen is estradiol, estriol, mestranol, ethinyl estradiol, diethylstilbestrol, or combinations thereof.

As used herein, a "progestin" refers to a progestogen, a progestational substance, or any pharmaceutically acceptable substance in the steroid art that generally possesses progestational activity including synthetic steroids that have progestational activity. Progestins suitable for use with the present invention can be of natural or synthetic origin. Progestins generally possess a cyclo-pentanophertanthrene nucleus.

Progestins suitable for use in the present invention include, but are not limited to, natural and synthetic compounds having progestational activity, such as, for example, progesterone, medroxyprogesterone, medroxyprogesterone acetate, chlormadinone acetate, norethindrone, cyproterone acetate, norethindrone acetate, desogestrel, levonorgestrel, drospirenone, trimegestone, norgestrel, norgestimate, norelgestromin, etonogestrel, dienogest, gestodene, megestrol, and other natural and/or synthetic gestagens. In some embodiments, the progestin is progesterone, etonogestrel, levonorgestrel, gestodene, norethisterone, drospirenone, or combinations thereof. In one embodiment, the progestin is levonorgestrel. In another embodiment, the progestin is nesterone.

Prodrugs of suitable progestins can also be used in the intravaginal device of the present invention. Ethynodiol diacetate, which is converted in vivo to norethindrone, is an example of a progestin prodrug that can be used in the present invention. Additional examples of progestin prodrugs include, but are not limited to, norgestimate (which is converted in vivo to 17-deacetyl norgestimate, also known as norelgestromin), desogestrel (which is converted in vivo to 3-keto desogestrel, also known as etonogestrel), and norethindrone acetate (which is converted in vivo to norethindrone).

In some embodiments, the progestin is desogestrel, etonogestrel, norgestimate, or combinations thereof.

In some embodiments, the active agent is a modified testosterone, e.g., a derivative of the synthetic steroid ethisterone. In some embodiments, the modified testosterone is danazol.

In some embodiments, the intravaginal ring of the present invention may comprise dapivirine and two contraceptive agents, such as a progestin and an estrogen. In some embodiments, the intravaginal ring comprises dapivirine and a combination of a progestin and an estrogen.

In one embodiment, about 10 to about 30 mg of contraceptive is present in the ring. In another embodiment, about 20 mg to about 30 mg of contraceptive is present in the ring. In yet another embodiment, about 10 to about 800 mg, about 50 mg to about 750 mg, about 100 mg to about 700 mg, or about 200 mg to about 600 mg, about 300 mg to about 400 mg of contraceptive is present in the ring.

In another embodiment, about 15 mg of contraceptive is present in the ring. In another embodiment, about 16 mg of contraceptive is present in the ring. In another embodiment, about 25 mg of contraceptive is present in the ring. In another embodiment, about 32 mg of contraceptive is present in the ring. In another embodiment, about 100 mg of contraceptive is present in the ring. In another embodiment, about 150 mg of contraceptive is present in the ring. In another embodiment, about 250 mg of contraceptive is present in the ring. In another embodiment, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 90 mg, about 100 mg, about 125 mg, about 150 mg, about 175 mg, about 200 mg, about 225 mg, about 250 mg, about 275 mg, about 300 mg, about 350 mg, about 400 mg, about 450 mg, about 500 mg, about 550 mg, about 600 mg, about 650 mg, about 700 mg, about 750 mg, or about 800 mg of contraceptive is present in the ring.

Surprisingly, the combination of dapivirine and a contraceptive, e.g., levonorgestrel, in the intravaginal rings of the invention results in the formation of a eutectic composition and provides an increased release rate of the contraceptive, e.g., levonorgestrel, as compared to the release rate of the contraceptive, e.g., levonorgestrel, in intravaginal rings comprising the contraceptive, e.g., levonorgestrel, without dapivirine. For example, in one embodiment, the release rate of the contraceptive from an intravaginal ring of the invention comprising dapivirine and the contraceptive is increased at least about 2-fold per day as compared to the release rate of the contraceptive from an intravaginal ring comprising the contraceptive without dapivirine. In one embodiment, the release rate of the contraceptive from an intravaginal ring of the invention comprising dapivirine and the contraceptive is increased at least about 10-fold per day as compared to the release rate of the contraceptive from an intravaginal ring comprising the contraceptive without dapivirine. In another embodiment, the release rate of the contraceptive from an intravaginal ring of the invention comprising dapivirine and the contraceptive is increased at least about 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50-fold per day as compared to the release rate of the contraceptive from an intravaginal ring comprising the contraceptive without dapivirine. In one embodiment, the release rate of the contraceptive from an intravaginal ring of the invention comprising dapivirine and the contraceptive is increased by about 2-fold to about 50-fold, by about 2-fold to about 25-fold, by about 2-fold to about 20-fold, by about 2-fold to about 15-fold, by about 2-fold to about 10-fold, by about 2-fold to about 5-fold, by about 5-fold to about 25-fold, by about 5-fold to about 20-fold, by about 5-fold to about 15-fold, by about 5-fold to about 10-fold, by about 10-fold to about 25-fold, or by about 1-fold to about 20-fold per day as compared to the release rate of the contraceptive from an intravaginal ring comprising the contraceptive without dapivirine.

In one embodiment, the cumulative release rate of the contraceptive from an intravaginal ring of the invention comprising dapivirine and the contraceptive is increased at least about 2-fold after 30 days, after 60 days, or after 90 days as compared to the cumulative release rate of the contraceptive from an intravaginal ring comprising the contraceptive without dapivirine after 30 days, after 60 days, or after 90 days. In one embodiment, the cumulative release rate of the contraceptive from an intravaginal ring of the invention comprising dapivirine and the contraceptive is increased at least about 10-fold after 30 days, after 60 days, or after 90 days as compared to the cumulative release rate of the contraceptive from an intravaginal ring comprising the contraceptive without dapivirine after 30 days, after 60 days, or after 90 days. In another embodiment, the cumulative release rate of the contraceptive from an intravaginal ring of the invention comprising dapivirine and the contraceptive is increased at least about 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50-fold after 30 days, after 60 days, or after 90 days as compared to the cumulative release rate of the contraceptive from an intravaginal ring comprising the contraceptive without dapivirine after 30 days, after 60 days, or after 90 days. In one embodiment, the cumulative release rate of the contraceptive from an intravaginal ring of the invention comprising dapivirine and the contraceptive is increased by about 2-fold to about 50-fold, by about 2-fold to about 25-fold, by about 2-fold to about 20-fold, by about 2-fold to about 15-fold, by about 2-fold to about 10-fold, by about 2-fold to about 5-fold, by about 5-fold to about 25-fold, by about 5-fold to about 20-fold, by about 5-fold to about 15-fold, by about 5-fold to about 10-fold, by about 10-fold to about 25-fold, or by about 1-fold to about 20-fold after 30 days, after 60 days, or after 90 days as compared to the cumulative release rate of the contraceptive from an intravaginal ring comprising the contraceptive without dapivirine after 30 days, after 60 days, or after 90 days.

In one embodiment, the release rate of the dapivirine from an intravaginal ring of the invention comprising dapivirine and a contraceptive is not increased as compared to the release rate of dapivirine from an intravaginal ring comprising only dapivirine. In another embodiment, the release rate of the dapivirine from an intravaginal ring of the invention comprising dapivirine and a contraceptive is also increased as compared to the release rate of dapivirine from an intravaginal ring comprising only dapivirine.

Values and ranges included and/or intermediate within the ranges set forth herein are also intended to be within the scope of the present disclosure. Ranges having values recited herein as an upper or lower limit are also intended to be within the scope of the present disclosure.

V. Methods for Preventing/Treating HIV and/or Pregnancy

The present invention provides methods of preventing and/or treating HIV and preventing pregnancy using the intravaginal rings of the invention comprising dapivirine and a contraceptive. The present invention also provides methods of preventing and/or treating HIV using the intravaginal rings of the invention comprising dapivirine and an antimicrobial compound. In one aspect, the present invention provides methods of blocking DNA polymerization by an HIV reverse transcriptase enzyme in a female human, comprising the step of inserting an intravaginal ring of the invention into the vagina of the female human. In another aspect, the present invention provides methods of preventing HIV infection in a female human, comprising the step of inserting an intravaginal ring of the invention into the vagina of the female human. In yet another aspect, the invention provides methods of treating HIV infection in a female human, comprising the step of inserting an intravaginal ring of the invention into the vagina of the female human. In another aspect, the invention provides methods of preventing pregnancy in a female human, comprising the step of inserting an intravaginal ring of the invention into the vagina of the female human.

The ring that is inserted into a human may contain a prophylactically effective amount or a therapeutically effective amount of dapivirine and an antimicrobial compound, e.g., maraviroc. The ring that is inserted into a human may contain a prophylactically effective amount or a therapeutically effective amount of dapivirine and a contraceptive, e.g., levonorgestrel.

As used herein, the term "prophylactically effective amount" refers to the amount of dapivirine or the amount of antimicrobial compound effective to prevent development of disease in the subject. In one embodiment of the invention, the disease is HIV. In a preferred embodiment of the invention, a prophylactically effective amount is achieved when less than about 7 mg, or when between about 1 mg and about 3 mg of dapivirine and/or antimicrobial compound is released in vitro during an initial 24 hour period of release. In one embodiment of the invention, a prophylactically effective amount is achieved when between about 100 µg to about 700 µg, or when between about 100 mg to about 700 mg of dapivirine and/or antimicrobial compound is released in vitro per day after the initial 7 day period of release. In one embodiment of the invention, a prophylactically effective amount is achieved when between about 200 µg to about 400 µg of dapivirine and/or antimicrobial compound is released in vitro per day after the initial 7 day period of release. In another embodiment of the invention, a prophylactically effective amount is achieved when between about 250 µg to about 350 µg of dapivirine and/or antimicrobial compound is released in vitro per day after the initial 7 day period of release. In another embodiment of the invention, a prophylactically effective amount is achieved when between about 300 µg to about 400 µg of dapivirine and/or antimicrobial compound is released in vitro per day after the initial 7 day period of release. In one embodiment, a prophylactically effective amount is achieved when about 50 µg, about 100 µg, about 125 µg, about 150 µg, about 175 µg, about 200 µg, about 225 µg, about 250 µg, about 275 µg, about 300 µg, about 325 µg, about 350 µg, about 375 µg, about 400 µg, about 450 µg, about 475 µg, about 500 µg, about 550 µg, about 600 µg, about 650 µg, about 700 µg, about 750 µg, about 800 µg, about 850 µg, about 900 µg about 950 µg, about 1 mg, less than 1 mg or more than 1 mg of dapivirine and/or antimicrobial compound is released in vitro per day after the initial 7 day period of release.

In another embodiment, a prophylactically effective amount is achieved when between about 5 µg and about 300 µg of dapivirine and/or antimicrobial compound is released in vivo per gram of vaginal fluid each day for 24 days after an initial 3 day period of use. In another embodiment, a prophylactically effective amount is achieved when between about 10 µg and about 100 µg of dapivirine and/or antimicrobial compound is released in vivo per gram of vaginal fluid each day for 24 days after an initial 3 day period of use. In another embodiment, a prophylactically effective amount is achieved when between about 20 µg and about 80 µg of dapivirine and/or antimicrobial compound is released in vivo per gram of vaginal fluid each day for 24 days after an initial 3 day period of use. In yet another embodiment, a prophylactically effective amount is achieved when about 5 µg, about 10 µg, about 25 µg, about 50 µg, about 75 µg, about 100 µg, about 125 µg, about 150 µg, about 175 µg, about 200 µg, about 225 µg, about 250 µg, about 275 µg, about 300 µg, about 350 µg, about 400 µg, about 450 µg, about 500 µg, or about 600 µg of dapivirine and/or antimicrobial compound is released in vivo per gram of vaginal fluid each day for 24 days after an initial 3 day period of use.

As used herein, the term "prophylactically effective amount" refers to the amount of contraceptive effective to prevent contraception or pregnancy in the subject. In one embodiment of the invention, a prophylactically effective amount is achieved when less than about 2 g of the contraceptive is released in vitro during an initial 24 hour period of release. In another embodiment, a prophylactically effective amount is achieved when less than about 1 g of the contraceptive is released in vitro during an initial 24 hour period of release. In one embodiment of the invention, a prophylactically effective amount is achieved when about 20 µg per day to about 290 µg per day of the contraceptive is released in vitro for about 23 days after the initial 7 day period of release. In one embodiment of the invention, a prophylactically effective amount is achieved when about 20 µg per day to about 290 µg per day of the contraceptive is released in vitro for about 53 days after the initial 7 day period of release. In one embodiment of the invention, a prophylactically effective amount is achieved when about 35 µg per day to about 70 µg per day of the contraceptive is released in vitro for about 23 days after the initial 7 day period of release. In one embodiment of the invention, a prophylactically effective amount is achieved when about 35 µg per day to about 70 µg per day of the contraceptive is released in vitro for about 53 days after the initial 7 day period of release.

In one embodiment of the invention, a prophylactically effective amount is achieved when less than about 100 μg per day of the contraceptive is released in vitro after the initial 7 day period of release for about 23 days. In one embodiment of the invention, a prophylactically effective amount is achieved when less than about 100 μg per day of the contraceptive is released in vitro after the initial 7 day period of release for about 53 days. In one embodiment of the invention, a prophylactically effective amount is achieved when less than about 70 μg per day of the contraceptive is released in vitro after the initial 7 day period of release for about 23 days. In one embodiment of the invention, a prophylactically effective amount is achieved when less than about 70 μg per day of the contraceptive is released in vitro after the initial 7 day period of release for about 53 days. In one embodiment of the invention, a prophylactically effective amount is achieved when less than about 15 μg per day of the contraceptive is released in vitro after the initial 7 day period of release for about 23 days. In one embodiment of the invention, a prophylactically effective amount is achieved when less than about 15 μg per day of the contraceptive is released in vitro after the initial 7 day period of release for about 53 days. In one embodiment of the invention, a prophylactically effective amount is achieved when about 35 μg per day of the contraceptive is released in vitro after the initial 7 day period of release for about 23 days or for about 53 days.

In one embodiment of the invention, a prophylactically effective amount is achieved when about 20 μg per day to about 290 μg per day of the contraceptive is released in vitro for about 30 days. In one embodiment of the invention, a prophylactically effective amount is achieved when about 20 μg per day to about 290 μg per day of the contraceptive is released in vitro for about 60 days. In one embodiment of the invention, a prophylactically effective amount is achieved when about 35 μg per day to about 70 μg per day of the contraceptive is released in vitro for about 30 days. In one embodiment of the invention, a prophylactically effective amount is achieved when about 35 μg per day to about 70 μg per day of the contraceptive is released in vitro for about 60 days.

In one embodiment of the invention, a prophylactically effective amount is achieved when less than about 100 μg per day of the contraceptive is released in vitro for about 30 days. In one embodiment of the invention, a prophylactically effective amount is achieved when less than about 100 μg per day of the contraceptive is released in vitro for about 60 days. In one embodiment of the invention, a prophylactically effective amount is achieved when less than about 70 μg per day of the contraceptive is released in vitro for about 30 days. In one embodiment of the invention, a prophylactically effective amount is achieved when less than about 70 μg per day of the contraceptive is released in vitro for about 60 days. In one embodiment of the invention, a prophylactically effective amount is achieved when less than about 35 μg per day of the contraceptive is released in vitro for about 30 days. In one embodiment of the invention, a prophylactically effective amount is achieved when less than about 35 μg per day of the contraceptive is released in vitro for about 60 days. In one embodiment of the invention, a prophylactically effective amount is achieved when less than about 15 μg per day of the contraceptive is released in vitro for about 30 days. In one embodiment of the invention, a prophylactically effective amount is achieved when less than about 15 μg per day of the contraceptive is released in vitro for about 60 days.

Values and ranges included and/or intermediate within the ranges set forth herein are also intended to be within the scope of the present disclosure. Ranges having values recited herein as an upper or lower limit are also intended to be within the scope of the present disclosure.

As used herein, the term "therapeutically effective amount" refers to the amount of compound effective to treat disease in the subject. In one embodiment of the invention, the disease is HIV. In a preferred embodiment of the invention, a therapeutically effective amount is achieved when less than about 7 mg, or between about 1 mg and about 3 mg of dapivirine and/or antimicrobial compound is released in vitro during an initial 24 hour period of release. In one embodiment of the invention, a therapeutically effective amount is achieved when between about 100 μg to about 700 μg, or between about 100 mg and about 500 mg of dapivirine and/or antimicrobial compound is released in vitro per day after the initial 7 day period of release. In one embodiment of the invention, a therapeutically effective amount is achieved when between about 200 μg to about 400 μg of dapivirine and/or antimicrobial compound is released in vitro per day after the initial 7 day period of release. In another embodiment of the invention, a therapeutically effective amount is achieved when between about 250 μg to about 350 μg of dapivirine and/or antimicrobial compound is released in vitro per day after the initial 7 day period of release. In another embodiment of the invention, a therapeutically effective amount is achieved when between about 100 μg to about 400 μg of dapivirine and/or antimicrobial compound is released in vitro per day after the initial 7 day period of release. In one embodiment, a therapeutically effective amount is achieved when about 100 μg, about 125 μg, about 150 μg, about 175 μg, about 200 μg, about 225 μg, about 250 μg, about 275 μg, about 300 μg, about 325 μg, about 350 μg, about 375 μg, about 400 μg, about 450 μg, about 475 μg, about 500 μg, about 550 μg, about 600 μg, about 650 μg, or about 700 μg of dapivirine and/or antimicrobial compound is released in vitro per day after the initial 7 day period of release.

In another embodiment, a therapeutically effective amount is achieved when between about 5 μg and about 300 μg of dapivirine and/or antimicrobial compound is released in vivo per gram of vaginal fluid each day for 24 days after an initial 3 day period of use. In another embodiment, a therapeutically effective amount is achieved when between about 10 μg and about 100 μg of dapivirine and/or antimicrobial compound is released in vivo per gram of vaginal fluid each day for 24 days after an initial 3 day period of use. In another embodiment, a therapeutically effective amount is achieved when between about 20 μg and about 80 μg of dapivirine and/or antimicrobial compound is released in vivo per gram of vaginal fluid each day for 24 days after an initial 3 day period of use. In yet another embodiment, a therapeutically effective amount is achieved when about 5 μg, about 10 μg, about 25 μg, about 50 μg, about 75 μg, about 100 μg, about 125 μg, about 150 μg, about 175 μg, about 200 μg, about 225 μg, about 250 μg, about 275 μg, about 300 μg, about 350 μg, about 400 μg, about 450 μg, about 500 μg, or about 600 μg of dapivirine and/or antimicrobial compound is released in vivo per gram of vaginal fluid each day for 24 days after an initial 3 day period of use.

Values and ranges included and/or intermediate within the ranges set forth herein are also intended to be within the scope of the present disclosure. Ranges having values recited herein as an upper or lower limit are also intended to be within the scope of the present disclosure.

Those of skill in the prevention and/or treatment of HIV and the prevention of pregnancy could determine the appropriate therapeutically effective amount or prophylactically effective amount from the data presented here in the Examples section. The exact dosage may depend on the particular active agent used.

The term "subject" means female humans who use the rings. Administration of the rings of the present invention to a subject can be carried out using known procedures, at dosages and for periods of time effective to treat or prevent HIV or to prevent pregnancy.

As used herein, the term "vagina" or "vaginal" refers to the passage leading from the opening of the vulva to the cervix of the uterus in female humans. As used herein, the term "intravaginal administering" refers to the administration of a ring of the invention to the vagina of a female human.

The rings of the present invention may be administered into the vagina of a subject prior to sexual intercourse, e.g., 1, 2, 3, 4, 5 or 6 weeks, prior to sexual intercourse. In some embodiments, the rings of the invention may be administered into the vagina of a subject after sexual intercourse, e.g., 1, 2, 3, 4, 5, 6, 7, 8, 9, 10, 11, 12, 13, 14 or 15 days after sexual intercourse.

The term sexual intercourse means vaginal sex.

The term "partners" as used herein defines two or more humans, who are sexually active with each other, i.e., who have sexual intercourse with each other.

As used herein, the term "preventing HIV infection" or "preventing HIV transmission" includes the application or administration of an intravaginal ring of the invention to a subject who is at risk of developing HIV, or who has been exposed to but not yet developed HIV, in order to decrease the likelihood that the subject will develop HIV. In one embodiment of the invention, the term "preventing HIV infection" includes the application or administration of an intravaginal ring of the invention to a subject who is at risk of developing HIV, or who has been exposed to but not yet developed HIV, in order to decrease the likelihood that the subject will develop HIV, as compared to a subject who has not been administered an intravaginal ring. In one embodiment of the invention, proper use of the intravaginal rings of the invention leads to prevention of HIV infection in about 1%, about 5%, about 10%, about 15%, about 20%, about 25%, about 30%, about 35%, about 40%, about 45%, about 50%, about 55%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% of the subjects who are at risk of developing HIV or who have been exposed to but not yet developed HIV. Values and ranges included and/or intermediate within the ranges set forth herein are also intended to be within the scope of the present disclosure. Ranges having values recited herein as an upper or lower limit are also intended to be within the scope of the present disclosure.

As used herein, the term "preventing pregnancy" includes the application or administration of an intravaginal ring of the invention to a subject who is at risk of becoming pregnant in order to decrease the likelihood that the subject will become pregnant. In one embodiment of the invention, the term "preventing pregnancy" includes the application or administration of an intravaginal ring of the invention to a subject who is at risk of becoming pregnant in order to decrease the likelihood that the subject will become pregnant, as compared to a subject who has not been administered an intravaginal ring. In one embodiment of the invention, proper use of the intravaginal rings of the invention leads to prevention of pregnancy infection in about 1%, about 5%, about 10%, about 15%, about 20%, about 25%, about 30%, about 35%, about 40%, about 45%, about 50%, about 55%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% of the subjects who are at risk of becoming pregnant. Values and ranges included and/or intermediate within the ranges set forth herein are also intended to be within the scope of the present disclosure. Ranges having values recited herein as an upper or lower limit are also intended to be within the scope of the present disclosure.

The term "treating" includes the application or administration of an intravaginal ring of the invention to a subject, or application or administration of an intravaginal ring of the invention to a subject who has HIV, with the purpose of curing, healing, alleviating, relieving, altering, remedying, ameliorating, preventing, improving, or affecting HIV. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; or improving a subject's physical or mental well-being. Treatment may be therapeutic or prophylactic. The treatment or amelioration of symptoms can be based on objective or subjective parameters; including the results of a physical examination.

VI. Methods for Preparing Rings of the Invention

Rings of the invention may be manufactured by any method known by those skilled-in-the-art, but preferably by injection molding or extrusion, and more preferably by reaction injection molding of silicone elastomer systems. The term 'injection molding' refers to manufacturing processes for producing parts/devices from either thermoplastic or thermosetting materials using suitably designed injection molds. Examples of thermoplastic materials include polyethylene and PEVA; examples of thermosetting materials include silicone rubbers/elastomers. Without limitation, matrix-type silicone elastomer rings containing dapivirine may be prepared by (i) adding and mixing the dapivirine into one or more components of the silicone system (e.g., base, crosslinking agent, catalyst, excipient, dispersant, etc) (ii) injecting the mix into suitably designed injection molds, and (iii) optionally, applying heat to cause the silicone mix to cure/crosslink forming an elastomer.

The present invention further provides methods of preparing the intravaginal rings of the invention described above. These methods generally comprise dispersing dapivirine and either an antimicrobial agent or a contraceptive, and an elastomer, e.g., polysiloxane, in an appropriate solvent or dispersing agent, e.g., silicone liquid, and curing the rings with a platinum catalyst, e.g., a platinum-siloxane complex, thereby preparing a platinum-catalyzed ring. Any of the well-known elastomers, e.g., polysiloxanes, described supra may be used to prepare the platinum-catalyzed rings of the invention. In one embodiment, an elastomer, e.g., polysiloxane, for use in the methods of the invention is a dimethylsiloxane, e.g., vinyl-terminated polydimethylsiloxane. In another embodiment, an elastomer, e.g., polysiloxane, for use in the methods of the invention is a diorganopopolysiloxane, e.g., dimethylpolysiloxane. In another embodiment, the elastomer, e.g., polysiloxane, for use in the methods of the invention is MED-8470. In certain embodiments, the methods further comprise use of a cross-linker, e.g., hydride functional polydimethylsiloxane or dimethylmethylhydrogen polysiloxane cross-link.

In one embodiment, the method further comprises catalyzing the rings in a ring mould. The mould can then be opened, following which the intravaginal ring is removed and trimmed. Ring moulds, are preferably coated with, for example, Teflon™ or an electrolytically applied metalised coating. Ring moulds may be constructed of hardened carbon steel, stainless steel, aluminum, or any other material deemed to be appropriate. It will be appreciated that the mould dimensions and design impart the physical shape of the intravaginal drug delivery device, for example, a partial or complete ring, or any other desired shape. Preferably, the device has a partial or complete toroidal shape, more preferably a partial or complete torus shape, or a substantially cylindrical shape. By toroid is meant a ring-like body generated by rotating any closed loop (including an ellipse, a circle or any irregular curve) about a fixed line external to that loop. The toroid shape may be a complete or partial toroid. By torus is meant a ring-like body generated by rotating a circle about a fixed line external to the circle. The torus shape may be a complete or partial ring-like shape. The geometric characteristics of the mould and intravaginal rings can be varied as required by the use.

Alternatively, the intravaginal ring device, or components thereof, may be prepared by extrusional processes, e.g., co-extrusion or blend extrusion, well known to those skilled in the art (see, e.g., U.S. Pat. No. 5,059,363, the entire contents of which are incorporated herein by reference).

The present invention is further illustrated by the following examples, which should not be construed as further limiting. The contents of all figures and all references, patents and published patent applications cited throughout this application, as well as the Figures, are expressly incorporated herein by reference in their entirety.

EXAMPLES

Example 1: Eleven Prototype Rings in MED4870 Comprising Dapivirine and a Contraceptive The purpose of this work was to establish whether a matrix-type ring containing both dapivirine (DAP) and a contraceptive, such as levonorgestrel (LNG), might be a suitable formulation for a product, i.e., a ring that prevents HIV transmission and also provides effective contraceptive cover over a period of 30 days or 60 days.

Three loadings of DAP were chosen for further investigation in this study: 100 mg, 150 mg and 200 mg. LNG loadings of 16 mg and 32 mg were selected as being likely to provide clinically meaningful in vitro release rates over 60 days. Various combinations of the two APIs at these loadings were also included in the study, with eleven prototype formulations manufactured in total (see Table 1). Testing of formulations that continued to provide release of DAP and LNG at levels higher than the minimum acceptable level at day 60 was continued out to a total of 92 days.

A Babyplast injection molder and a mold set of cross-sectional diameter 7.82 mm, outer diameter 56.67 mm were used to manufacture the rings. The silicone elastomer used was MED-4870.

Dapivirine (micronised) was supplied by IPM. Levonorgestrel (non-micronised) was supplied by Haorui Pharma-Chem Inc. (Irvine, Calif.). MED-4870 silicone elastomer was obtained from NuSil. HPLC-grade acetonitrile, HPLC-grade isopropanol and potassium dihydrogen orthophosphate (AnalR analytical reagent) were purchased from VWR International Ltd. (Dublin, Ireland). Phosphoric acid (85% w/w in water) was purchased from Sigma-Aldrich (Gillingham, UK). A Millipore Direct-Q 3 UV Ultrapure Water System (Watford, UK) was used to obtain HPLC-grade water.

TABLE 1

Eleven matrix-type ring prototype formulations

| Formulation Code | DAP Loading (mg/ring) | DAP Loading % w/w | LNG Loading mg/ring | LNG Loading % w/w |
|---|---|---|---|---|
| A | 100 | 1.25 | — | — |
| B | 150 | 1.875 | — | — |
| C | 200 | 2.5 | — | — |
| D | — | — | 16 | 0.2 |
| E | — | — | 32 | 0.4 |
| F | 100 | 1.25 | 16 | 0.2 |
| G | 100 | 1.25 | 32 | 0.4 |
| H | 150 | 1.875 | 16 | 0.2 |
| I | 150 | 1.875 | 32 | 0.4 |
| J | 200 | 2.5 | 16 | 0.2 |
| K | 200 | 2.5 | 32 | 0.4 |

Premixes were first prepared by mixing appropriate quantities of each API with Part A or Part B of the silicone elastomer (Table 2). For each formulation, Premix A and Premix B were prepared in a 100 g batch size. The steps for preparation of 100 g of each premix were as follows: 1) Quantity of API (DAP and/or LNG) weighed into SpeedMixer tub according to Table 2. 2) Quantity of MED-4870 (Part A or Part B) added to SpeedMixer tub according to Table 2. 3) SpeedMixer tub sealed and contents mixed using SpeedMixer (3 min at 3000 rpm). 4) Premixes stored in fridge until required for injection moulding. 5) On date of manufacture, premixes were removed from fridge, hand mixed for 30 s and then SpeedMixed for 120 s @ 3000 rpm.

TABLE 2

Quantities of each component in 100 g premix

| Formulation | Mass of DAP (g) | Mass of LNG (g) | Mass of MED-4870 Part A or Part B (g) |
|---|---|---|---|
| A | 1.25 | — | 98.75 |
| B | 1.8758 | — | 98.125 |
| C | 2.5 | — | 97.5 |
| D | — | 0.2 | 99.8 |
| E | — | 0.4 | 99.6 |
| F | 1.25 | 0.2 | 99.55 |
| G | 1.25 | 0.4 | 98.35 |
| H | 1.875 | 0.2 | 97.925 |
| I | 1.875 | 0.4 | 97.725 |
| J | 2.5 | 0.2 | 97.3 |
| K | 2.5 | 0.4 | 97.1 |

Prior to injection moulding of rings, premixes of A and B were combined in a 1:1 ratio, according to the following procedure:

1. Premix A and 50 g of Premix B were added to the SpeedMixer tub in layers (25 g Premix A, then 25 g Premix B, then 25 g Premix A, then 25 g Premix B) and hand mixed for 30 s.
2. Tub placed into SpeedMixer (30 s at 3000 rpm).
3. Process repeated for each formulation until 4×100 g total A/B mixture produced.
4. Contents of each tub were transferred to a 500 g cartridge that operated with the dosing system on the Babyplast injection molder.

Heating of the ring mold assembly on the Babyplast machine was performed via 2×200 W heater cartridges on both the fixed and mobile plates. Injection parameters were as follows: Clamping pressure: 100 bar, Injection pressure: 50 bar, Mould temperature: 160° C., Cure time: 60 s. The measured dimensions of the ring mold were as follows: outer diameter: 56.67 mm, cross-sectional diameter: 7.82 mm.

In vitro release testing was performed daily (excluding weekends) for all rings over 30 days, followed by twice weekly sampling through day 60. Selected formulations (C and K) were tested twice weekly up to day 92. On day 0, each ring was placed into a 250 mL glass bottle containing 200 mL dissolution medium (1:1 mixture of isopropanol and water) and stored in an orbital shaking incubator (37° C., 60 rpm, 25 mm orbital throw). The dissolution medium was sampled and replaced (100 mL) daily with the exception of weekends (200 mL volume over weekend) until day 30. On day 30, 200 mL release medium was added to each bottle. The next sample time-point was day 38, and the release medium was sampled and completely replaced (100 mL). Samples were taken again on day 39 and the release medium was replaced with 200 mL. The same protocol was followed on days 45 and 46, days 52 and 53, and days 59 and 60. On the basis of observed release at day 60, release testing was extended to day 92 for formulations C and K; sampling was conducted on days 66 and 67, 73 and 74, 80 and 81, 87 and 88, 91 and 92 according to the same protocol. Drug release was quantified by reverse-phase HPLC analysis of all samples with UV detection.

The 'multi-API HPLC method' was used for analysis of all samples obtained during the dissolution study. Briefly, 25 µL of each sample was injected onto a Thermo Scientific BDS Hypersil C18 column (150 mm×4.6 mm, 3 µm particle size) fitted with a guard column. The column was held at 25° C. and isocratic elution was performed using a mobile phase of 55% 7.7 mM phosphate buffer (pH 3.0) and 45% HPLC-grade acetonitrile (1.2 mL/min) with a run time of 9 min. DAP was detected using a wavelength of 210 nm after 6.2 min, while LNG was detected after 7.7 min using a wavelength of 240 nm.

DAP and LNG release in vitro were compared for each ring set using a one-way ANOVA, followed by post-hoc analysis using the Tukey-Kramer multiple comparisons test. The following results were compared for both drugs: Day 1 release, Day 30 release, Day 60 release and Total release over 60 days. Analysis was conducted using GraphPad Prism software and significance was noted for a P value of less than 0.05: *=significant (0.01<P<0.05), =very significant (0.001<P<0.01), *=extremely significant (P<0.001), and ns=not significant (P >0.05).

Details of manufactured rings included in the in vitro release study are presented in Table 3.

TABLE 3

Mean mass of rings used in the in vitro release study (n = 6 per formulation)

| Formulation Code | Mean ring mass (g) (±sd) | DAP loading | | LNG loading | |
|---|---|---|---|---|---|
| | | Target DAP loading (mg) | Mean theoretical DAP loading (mg) (±sd) | Target LNG loading (mg) | Mean theoretical LNG loading (mg) (±sd) |
| A | 7.99 (±0.01) | 100 | 99.91 (±0.14) | — | — |
| B | 7.98 (±0.01) | 150 | 149.66 (±0.22) | — | — |
| C | 8.01 (±0.01) | 200 | 200.20 (±0.25) | — | — |
| D | 7.98 (±0.01) | — | — | 16 | 15.97 (±0.03) |
| E | 7.95 (±0.01) | — | — | 32 | 31.82 (±0.02) |
| F | 7.97 (±0.01) | 100 | 99.62 (±0.02) | 16 | 15.94 (±0.00) |
| G | 8.00 (±0.01) | 100 | 100.02 (±0.07) | 32 | 32.01 (±0.02) |
| H | 8.00 (±0.01) | 150 | 150.04 (±0.05) | 16 | 16.00 (±0.00) |
| I | 8.00 (±0.01) | 150 | 149.96 (±0.08) | 32 | 31.99 (±0.2) |
| J | 7.97 (±0.01) | 200 | 119.19 (±0.17) | 16 | 15.94 (±0.01) |
| K | 8.06 (±0.01) | 200 | 201.53 (±0.17) | 32 | 32.24 (±0.03) |

Daily and cumulative release charts for DAP and LNG from each ring set are presented in FIGS. 1 and 2 respectively, up to and including day 60. A summary of all in vitro release data is presented in Tables 4 and 5.

TABLE 4

Summary of DAP release date for each formulation (n = 6).

| Code | Day 1 release (µg) (±sd) | Day 30 release (µg) (±sd) | Day 60 release (µg) (±sd) | Cumulative release after 60 days (mg) (±sd) | % Release after 60 days (±sd) | Daily release rate (µg/day) | $R^2$ (linear regression analysis) |
|---|---|---|---|---|---|---|---|
| A | 4132 (±65) | 414 (±2) | 284 (±2) | 36.7 (±0.2) | 37 (±0.3) | 4781 | 0.9993 |
| B | 5149 (±126) | 514 (±6) | 363 (±5) | 45 (±0.2) | 30 (±0.1) | 5878 | 0.9997 |

TABLE 4-continued

Summary of DAP release date for each formulation (n = 6).

| Code | Day 1 release (µg) (±sd) | Day 30 release (µg) (±sd) | Day 60 release (µg) (±sd) | Cumulative release after 60 days (mg) (±sd) | % Release after 60 days (±sd) | Daily release rate (µg/day) | $R^2$ (linear regression analysis) |
|---|---|---|---|---|---|---|---|
| C | 5951 (±90)  | 618 (±6) | 437 (±1) | 53.3 (±0.3) | 27 (±0.2) | 6975 | 0.9998 |
| F | 4149 (±38)  | 409 (±4) | 284 (±2) | 36.1 (±0.1) | 36 (±0.1) | 4710 | 0.9994 |
| G | 4333 (±210) | 407 (±3) | 285 (±2) | 36.5 (±0.3) | 37 (±0.3) | 4741 | 0.9993 |
| H | 5360 (±280) | 525 (±4) | 373 (±4) | 46.0 (±0.1) | 31 (±0.1) | 5992 | 0.9997 |
| I | 5320 (±175) | 531 (±5) | 376 (±2) | 46.4 (±0.3) | 31 (±0.2) | 6056 | 0.9997 |
| J | 6113 (±60)  | 629 (±4) | 449 (±3) | 54.2 (±0.1) | 27 (±0.1) | 7098 | 0.9999 |
| K | 6038 (±103) | 634 (±5) | 454 (±3) | 54.8 (±0.3) | 27 (±0.1) | 7173 | 0.9997 |

TABLE 5

Summary of LNG release date for each formulation (n = 6).

| Code | Day 1 release (µg) (±sd) | Day 30 release (µg) (±sd) | Day 60 release (µg) (±sd) | Cumulative release after 60 days (mg) (±sd) | % Release after 60 days (±sd) | Daily release rate (µg/day) | $R^2$ (linear regression analysis) |
|---|---|---|---|---|---|---|---|
| D | 129 (±14) | 6.5 (±3)  | 2.0 (±1) | 0.89 (±0.03) | 6 (±0.2)  | 109  | 0.9503 |
| E | 303 (±35) | 20 (±2)   | 5.2 (±1) | 2.5 (±0.06)  | 8 (±0.2)  | 317  | 0.9347 |
| F | 245 (±18) | 64 (±2)   | 23 (±2)  | 5.0 (±0.09)  | 31 (±0.5) | 757  | 0.9909 |
| G | 612 (±61) | 147 (±5)  | 84 (±4)  | 10.9 (±0.2)  | 34 (±0.6) | 1608 | 0.9984 |
| H | 261 (±21) | 69 (±2)   | 25 (±2)  | 5.1 (±0.07)  | 32 (±0.4) | 781  | 0.9937 |
| I | 621 (±19) | 158 (±2)  | 91 (±3)  | 11.6 (±0.1)  | 36 (±0.4) | 1701 | 0.9984 |
| J | 286 (±13) | 72 (±2)   | 29 (±2)  | 5.4 (±0.09)  | 34 (±0.5) | 819  | 0.9945 |
| K | 684 (±17) | 155 (±4)  | 91 (±2)  | 11.6 (±0.1)  | 36 (±0.4) | 1696 | 0.9986 |

Formulations C and K were selected for extended in vitro release testing, up to day 92. Daily and cumulative release charts for DAP (formulations C and K) and LNG (formulation K only) are presented in FIGS. 3 and 4 respectively, up to and including day 92. A summary of the DAP and LNG release data over 92 days for formulations C and K is provided in Table 6.

TABLE 6

DAP and LNG release data over 92 days for C and K (n = 6)

| Code | API | Day 92 Release (µg)(±sd) | Cumulative release after 92 days (mg) (±sd) | % Release after 92 days (µg/day) | Daily release rate | $R^2$ (linear regression analysis) |
|---|---|---|---|---|---|---|
| C | DAP | 301 (±23) | 64.8 (±0.25) | 32 (±0.1) | 6852 | 0.9996 |
| K | DAP | 299 (±5)  | 66.6 (±0.33) | 33 (±0.2) | 7032 | 0.9995 |
|   | LNG | 46 (±2)   | 13.7 (±0.19) | 43 (±0.6) | 1595 | 0.9955 |

Release of DAP for each set of the DAP-loaded formulations followed the typical profile expected for matrix rings, i.e., a high mass was released on day 1 followed by steadily declining daily release over the course of the study (FIG. 1A). There is a linear relationship between cumulative release and root time for all formulations (Table 4), indicating that DAP was released via a diffusion-controlled mechanism.

Increasing the DAP loading produced a significant increase in the DAP release rate (P<0.001 for all relevant comparisons). However, the additional presence of LNG in the rings did not have a significant influence on DAP release. For rings containing 100 mg DAP and 0, 16 or 32 mg LNG (i.e., formulations A, F and G), there was no significant difference in DAP release for any of the comparisons made (P>0.05), with the exception of total release from formulations A and F (P<0.01). The total release of DAP from formulations A and F was 36.7 and 36.1 mg respectively, so the difference may not be evident in vivo and may simply be due to some minor inter-batch variation in the rings. The same is true for rings containing 150 mg DAP (B, G and H) and 200 mg DAP (C, J and K); while some of the release data appears to be significantly different, the actual values for release are very similar and may not be clinically significant. Alternatively, the presence of LNG could be causing a small increase in DAP release that would only become more apparent if much higher loadings of LNG were present in the rings. In all cases, low values of percentage RSD for the daily release data were observed, indicating that release is highly reproducible.

Based on in vitro release data generated, each formulation tested has potential as a 60-day product. Day 60 DAP release was 284-285 µg for the 100 mg DAP rings, 363-376 µg for the 150 mg DAP rings, and 437-454 µg for the 200 mg DAP rings, all exceeding the Day 60 release target of greater than 200 µg.

Figure 3A:
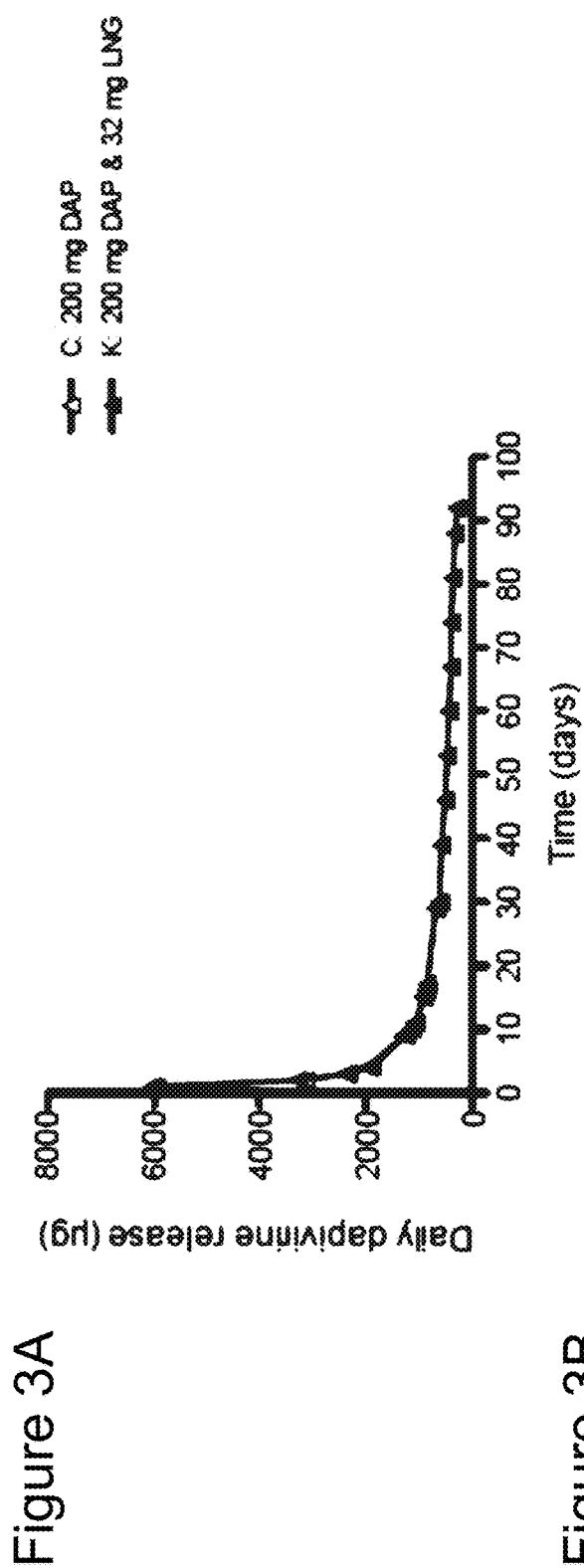
FIG. 3A and FIG. 3B depict the mean daily (FIG. 3A, ±sd) and cumulative (FIG. 3B) release of DAP from MED-4870 matrix rings comprising DAP (200 mg per ring), with or without LNG (32 mg per ring) over 92 days.
Figure 3B:
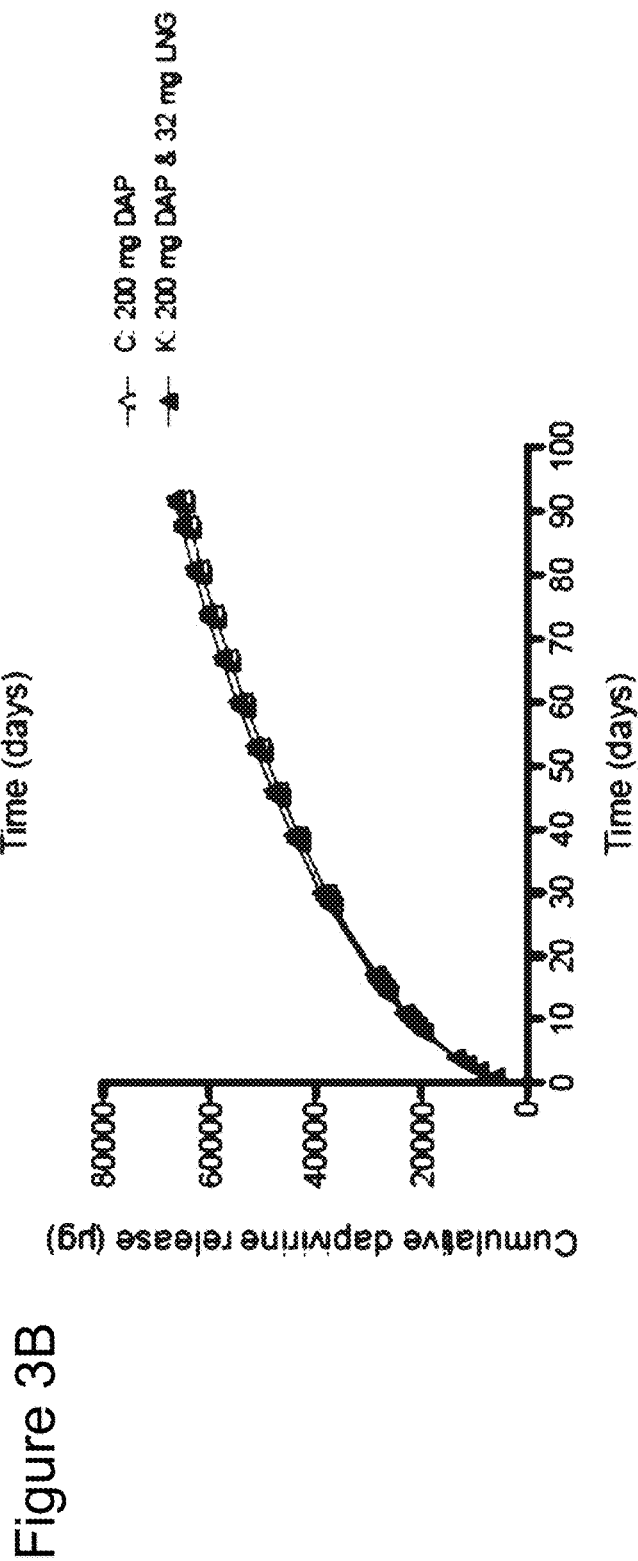
Figure 4A:
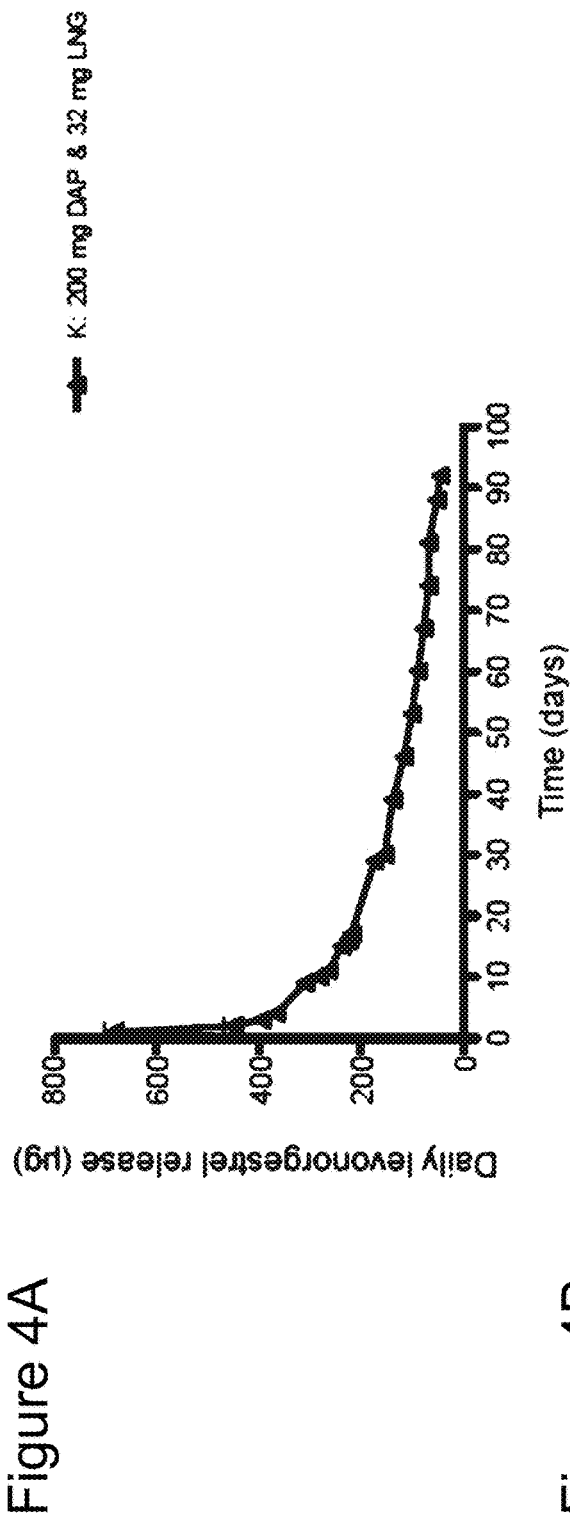
FIG. 4A and FIG. 4B depict the mean daily (FIG. 4A, ±sd) and cumulative (FIG. 4B) release of LNG from MED-4870 matrix rings comprising LNG (32 mg per ring) and DAP (200 mg per ring) over 92 days.
Figure 4B:
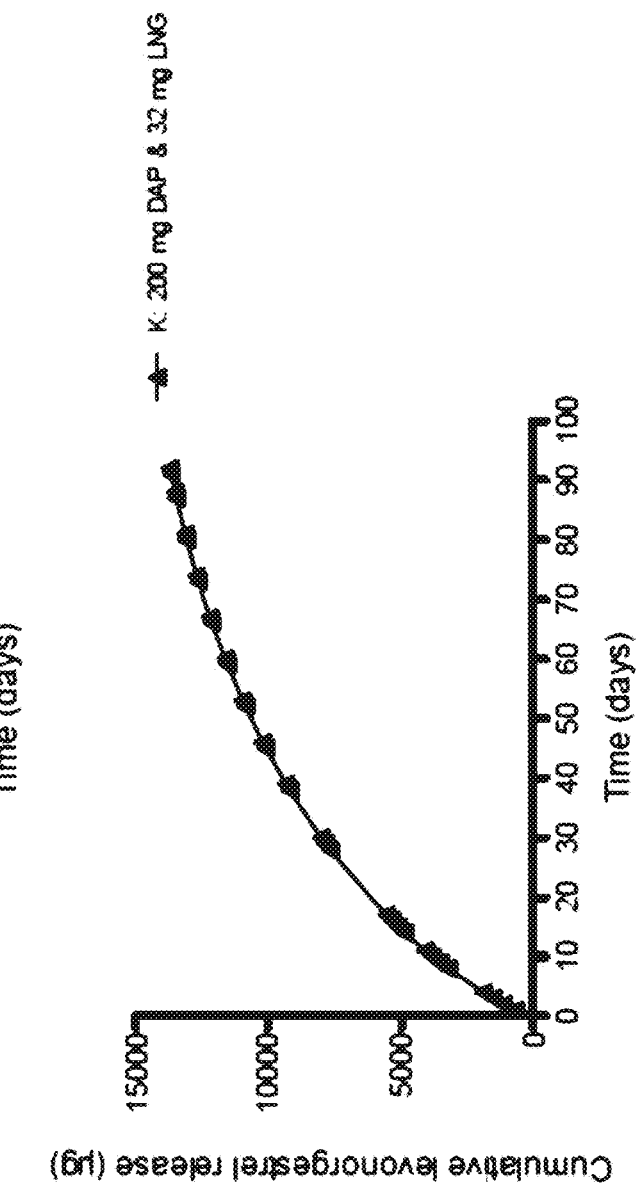

LNG highest release occurred on day 1, followed by declining daily release over time (FIG. 3A). LNG release increased with increased initial LNG loading (P<0.001 in all cases when equivalent formulations with different LNG loadings are compared). Release was diffusion-controlled for at least part of the release period. A linear relationship between cumulative release and root time was observed for formulations F-K over the full 60 days (i.e., DAP/LNG combination rings), but only up to day 17 for formulations D and E (i.e., LNG-only rings) (Table 6). This suggests that the presence of DAP in the rings is influencing LNG release. LNG release is very significantly increased by the presence of DAP when LNG-only rings are compared to DAP/LNG rings with equivalent LNG loading (FIGS. 3A and 3B) (P<0.001 in all cases). For the LNG-only rings, release was almost unquantifiable by day 60, despite only a small fraction of the initial drug loading having been released (6 and 8% for D and E, respectively). Each of the combination rings still released significant quantities of LNG on day 60, with 31-36% of the initial loading released over the course of the study (Table 6).

The presence of DAP in the ring may be enhancing the solubility of LNG in the silicone elastomer, resulting in a corresponding increase in release. Another possibility is that DAP and LNG are forming a eutectic mixture, which in turn is causing an increase in LNG release through a reduction in the melting point of each drug. The data suggests that it is the co-presence of DAP in the ring, rather than the magnitude of the initial loading, that causes a significant increase in LNG release. In most cases, a comparison of LNG release from rings containing the same loading of LNG but varying loadings of DAP showed no significant difference in release.

The LNG loadings for rings tested in this study were selected based on target day 60 release values for LNG of 35 µg and 70 µg. Formulations F, H and J all contained 16 mg LNG; release of LNG on day 60 was in the range 23-29 µg for each of these rings. This is slightly below the lower LNG target of 35 µg/day on day 60, indicating that the loading may need to be increased to ensure final daily release is above this target. A higher LNG loading of 32 mg was studied in formulations G, I and K; day 60 release from these rings ranged from 84 to 91 µg, i.e., above the higher target of 70 µg.

Two ring formulations, C and K, were selected for extended in vitro release testing (out to day 92). Formulation C contained 200 mg DAP; formulation K contained 200 mg DAP and 32 mg LNG. Release of both DAP and LNG continued according to the same trends observed up to day 60, i.e., release of both APIs steadily decreased over the study (FIG. 3) and there was a linear relationship between cumulative release and root time over the entire 92 days (Table 6). The purpose of the extended study was to determine whether a matrix ring might be suitable for use out to 3 months, as this would bring added benefits in terms of cost and user-adherence. For DAP, both formulations provided similar release on day 92 (301 and 299 µg for formulations C and K, respectively), which is well in excess of the target minimum level of 200 µg. Release of LNG from formulation K was 46 µg on day 92. This is above the lower target of 35 µg, but less than the higher target of 70 µg. A matrix formulation may therefore be suitable for use over 3 months.

Figure 5A:
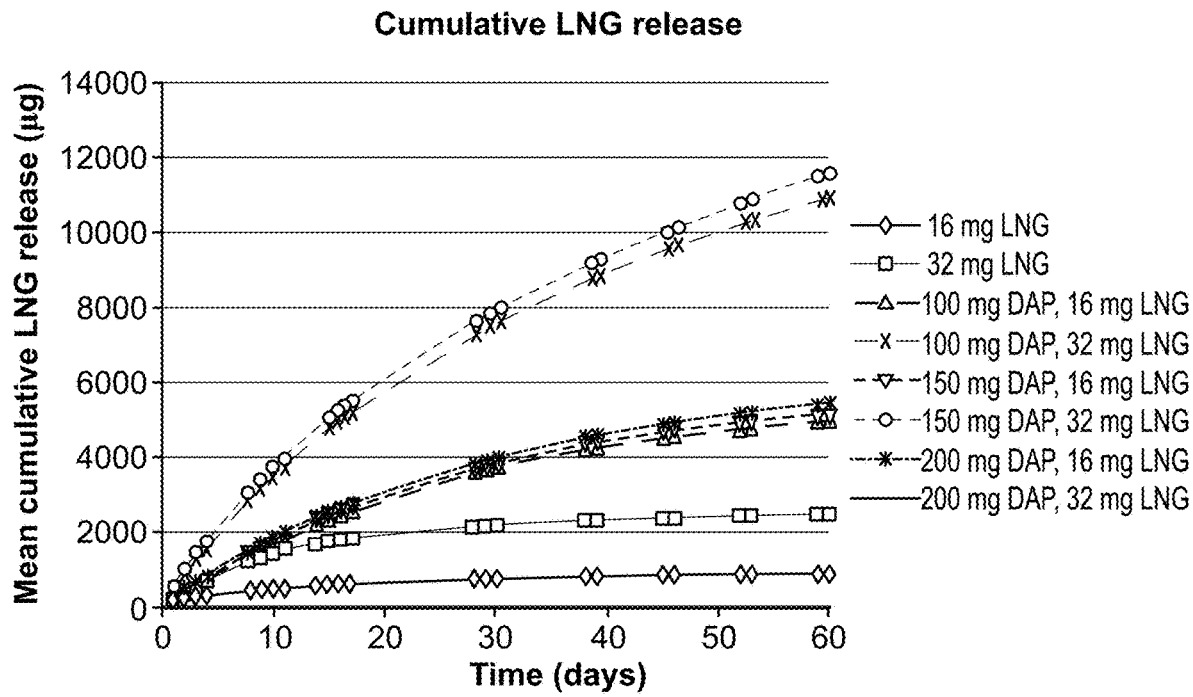
FIG. 5A and FIG. 5B depict LNG (FIG. 5A) and DAP (FIG. 5B) cumulative release versus time plots for various ring formulations described in Example 1.

LNG release is dependent on the initial LNG loading within the ring. Thus, rings with 16 mg LNG release less than those with 32 mg LNG. This is apparent for both the levonorgestrel-only rings and the combination rings (FIG. 5).

Figure 5B:
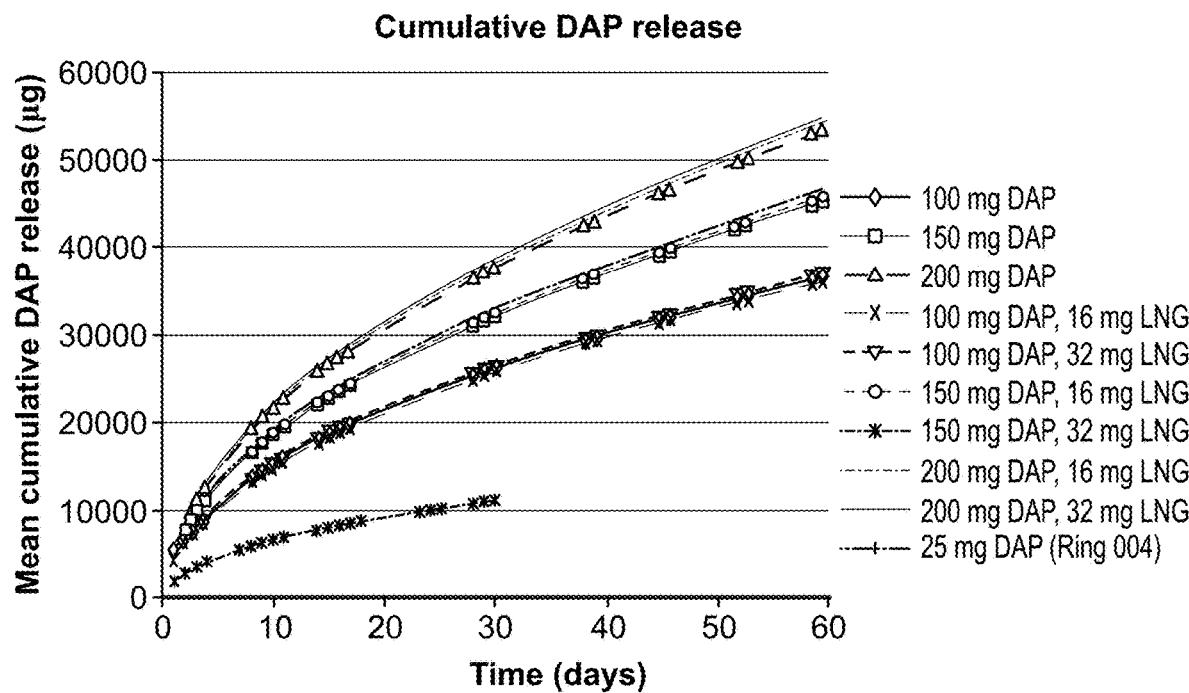

Levonorgestrel release is significantly increased in the presence of DAP compared with LNG alone. For example, Day 60 cumulative release for the 16 mg LNG-only ring was 885 mcg; when 100, 150 and 200 mg of DAP is included in the ring, Day 60 cumulative release was 5004, 5144 and 5408 mcg, respectively. Similarly, Day 60 cumulative release for the 32 mg LNG-only ring (red squares, FIG. 5) was 2506 mcg; when 100, 150 and 200 mg of DAP is included in the ring, Day 60 cumulative release was increased to 10934, 11556 and 11611 mcg, respectively. It is clear from these data that the actual loading of dapivirine is not important. Based on the drug loadings tested, it appears that the dapivirine merely needs to be present in the ring in order to enhance levonorgestrel release Dapivirine in vitro release is highly dependent on DAP loading. FIG. 5B shows three distinct groups of release profiles (excluding the 25 mg DAP ring profile), corresponding to rings containing 100, 150, 200 mg DAP. The LNG component in the rings does not influence DAP release in any meaningful way.

It is particularly surprising that the same increase in LNG release is observed in the presence of DAP irrespective of the DAP loading amount. The same increase in LNG would likely be observed when the DAP loading is reduced to 25 mg, or even 10 mg.

When solid drugs are incorporated into silicone elastomer vaginal rings, a fraction of the solid drug component dissolves in the silicone elastomer matrix. Assuming that excess solid drug is present in the matrix, the drug will ultimately saturate the silicone elastomer, in the same way that adding solid drug to water will result in a saturated solution. Therefore, for the 100, 150 and 200 mg DAP rings, each would contain the same concentration of dissolved DAP in the silicone elastomer matrix, despite the differences in overall DAP loading. It is this fixed concentration, solubilised DAP component in the combination rings that produces an increase in the LNG release, compared with LNG-only rings. In other words, the dissolved DAP component in the silicone elastomer is creating an environment in which LNG has increased solubility compared with its normal solubility in silicone elastomer.

Freezing-point depression describes the process in which adding a solute to a solvent produces a decrease in the freezing point of the solvent. Everyday examples include salt in water, alcohol in water, or the mixing of two solids such as impurities in a finely powdered drug. In such cases, the added compound is the solute, and the original solid can be thought of as the solvent. The resulting solution or solid-solid mixture has a lower freezing point (melting point) than the pure solvent or solid did. A eutectic system is a mixture of chemical compounds (or elements) that has a single chemical composition that solidifies at a lower temperature than any other composition made up of the same ingredients. This composition is known as the eutectic composition and the temperature at which it solidifies is known as the eutectic temperature. On a phase diagram the intersection of the eutectic temperature and the eutectic composition gives the eutectic point. This phenomenon is also demonstrated for the dapivirine-maraviroc system (see Example 6, below). The dapivirine-levonorgestrel system also behaves in the same way, such that the melting point of each component is reduced in the presence of the other component (in a concentration-dependent manner) such that a eutectic composition exists. Reducing the melting point of a drug in a two-component mixture often correlates with an increase in its solubility, which in turn enhances permeation and release. The increased levonorgestrel release observed from the rings also containing dapivirine is likely the result of decreased melting point of the levonorgestrel.

Example 2: Reservoir Rings Comprising a Contraceptive in the Core and Dapivirine in the Matrix Sheath The purpose of this work was to study a combination ring strategy comprising the contraceptive hormone levonorgestrel (LN) in the core and dapivirine in the sheath. Initial work involved the manufacture and in vitro release testing of two sets of rings—one having a tin-catalysed silicone elastomer core (MED8-6382) and the other a platinum-catalysed silicone elastomer core (DDU-4320). For both formulations, cores were overmolded with platinum-catalysed silicone elastomer (DDU-4320).

Levonorgestrel was selected as the contraceptive hormone for this study, since initial experiments demonstrated that it is compatible with platinum-catalyzed silicone elastomer and can be effectively released in vitro.

Rings were manufactured using the DDU-4320 grade of platinum-catalysed silicone elastomer. DDU-4320 is the fully approved medical grade of LSR9-9508-30.

In an earlier report, a LN release rate of approximately 30 µg/day was achieved from reservoir rings consisting of a levonorgestrel (LN)-loaded core with a blank sheath, with both components manufactured from LSR9-9508-30. However, initial results (reservoir ring with LN-loaded core and dapivirine (DAP)-loaded sheath, manufactured from DDU-4320) indicated that the LN release was substantially higher than that previously achieved, with a release rate of 124 µg/day. Given the markedly different release rates, additional rings were manufactured to further investigate the increased LN release rate. A second set of reservoir rings with a LN-loaded core and DAP-loaded sheath, manufactured using DDU-4320, were included in a second in vitro release study. Additional control rings were also manufactured using DDU-4320, and included a LN-loaded matrix ring, a LN-loaded reservoir ring (LN in the core, blank sheath) and a DAP-loaded reservoir ring (blank core, DAP-loaded sheath).

Dapivirine (micronised) was supplied by IPM. Levonorgestrel (non-micronised) was supplied by Haorui Pharma-Chem Inc. (Irvine, Calif.). DDU-4320 and MED8-6382 silicone elastomers were supplied by NuSil. HPLC-grade acetonitrile, HPLC-grade isopropanol and potassium dihydrogen orthophosphate (AnalR analytical reagent) were purchased from VWR International Ltd. (Dublin, Ireland). Phosphoric acid (85% w/w in water) was purchased from Sigma-Aldrich (Gillingham, UK). A Millipore Direct-Q 3 UV Ultrapure Water System (Watford, UK) was used to obtain HPLC-grade water.

Reservoir-type vaginal rings consisting of an active core (1% w/w LN) with a DAP loaded sheath (0.3125% w/w) were manufactured, using either DDU-4320 (addition cure system) or MED8-6382 (condensation cure system) for the core and (in all cases) DDU-4320 for the sheath, on a laboratory-scale injection-moulding machine. The manufacture of reservoir rings using this equipment is a three-stage process.

LN-loaded DDU-4320 cores were prepared by mixing 0.5 g LN with 49.5 g silicone elastomer (part A or part B) in a FlackTek SpeedMixer™ DAC 150 FVZ-K (3000 rpm, 1.5 min). Premix A and premix B were combined by speedmixing (1:1, 3000 rpm, 15 s) and then transferred to a SEMCO® injection cartridge. The cartridge was placed in a manual injection gun and the silicone elastomer was injected into a heated core-mould mounted on the injection-moulder and cured (90° C., 30 s). The dimensions of the core mould were as follows: Outer diameter=54.9 mm, Internal diameter=45.9 mm, Cross-sectional diameter=4.5 mm.

MED8-6382 cores were manufactured using MED8-6382 base and MED8-6382 crosslinker, which were first blended (25:1, 3500 rpm, 3 min) in a FlackTek SpeedMixer™ DAC 150 FVZ-K. The appropriate quantity of LN was mixed with the silicone elastomer using the SpeedMixer (3500 rpm, 3 min) to obtain 100 g drug-loaded premix (1% w/w LN). Catalyst (tin(II) 2-ethylhexanoate) was added (0.5% w/w) and the formulation was thoroughly mixed by hand. This active mix was transferred to a SEMCO® injection cartridge, which was placed in a manual injection gun. Cores were manufactured by injecting the mix into a heated mould (85° C.) mounted on a laboratory-scale injection moulding machine and curing for 90 s. A single cut was made in each MED8-6382 core prior to overmoulding to ensure a tight fit in the mould, since shrinkage of the full core after curing resulted in misalignment of cores within the sheath when no cut was made.

Once cured, each core was overmoulded in two steps using DAP-loaded DDU-4320 (0.3125% w/w DAP). DAP (0.156 g) was mixed with silicone elastomer (49.877 g of part A or part B) in the SpeedMixer (3000 rpm, 1.5 min). The active premixes (A and B) were combined (1:1) using the SpeedMixer (3000 rpm, 15 s), transferred to a SEMCO® injection cartridge, injected into a heated mould holding the unsheathed or partially sheathed core, and then cured (90° C., 90 s). The dimensions of the full-size ring moulds were as follows: Outer diameter=58.0 mm, Internal diameter=42.8 mm, Cross-sectional diameter=7.6 mm. The sheath thickness of the final rings was 1.55 mm. Six replicates of each formulation were manufactured and included in in vitro release testing. Prior to the release study, rings were stored at room temperature for three days in an open container. Rings with a DDU-4320 core will be referred to as "Set A" throughout this report, while rings with a MED8-6382 core will be referred to as "Set B".

Following this initial in vitro release study, an additional set of reservoir rings consisting of a DDU-4320 core (containing 1% w/w LN) and a DDU-4320 sheath (containing 0.3125% w/w DAP) were manufactured and a second in vitro release study was conducted. The purpose of this second release study was to confirm the results obtained from the first study. This additional ring set will be referred to as "Set C" (same formulation as Set A but manufactured at a later date). Following manufacture, rings in Set C were stored for one week in sealed foil pouches, prior to commencement of the in vitro release study. During manufacture of Set C, cores were cut prior to overmolding in the same manner as Set B (note that the cores in rings of Set A were NOT cut prior to overmolding). This additional step of cutting the core was added to the manufacturing process following the observation that cores composed of MED8-6382 shrank after curing. Although this was not observed to the same extent with DDU-4320 cores, it was decided that the cores of Set C should be cut to investigate whether this had any impact on the release of dapivirine and/or levonorgestrel from the rings.

In vitro release testing was performed for all rings over 30 days. Each ring was placed into a 250 mL glass bottle containing 50 mL dissolution medium (1:1 mixture of isopropanol and water) and stored in an orbital shaking incubator (37° C., 60 rpm, 25 mm orbital throw). The dissolution medium was sampled and replaced (50 mL) daily with the exception of weekends (50 mL volume over weekend). Drug release was quantified by reverse-phase HPLC with UV detection.

Details of manufactured rings are presented in Tables 7 and 8.

TABLE 7

Formulation Details for Each Ring Set

| Ring Set | Details |
|---|---|
| A | Reservoir Ring<br>LN-loaded DDU-4320 core (1% w/w LN) (not cut prior to overmoulding)<br>DAP-loaded DDU-4320 sheath (0.3125% w/w)<br>(first batch) |
| B | Reservoir Ring<br>LN-loaded DDU-6382 core (1% w/w LN) (cut prior to overmoulding)<br>DAP-loaded DDU-4320 sheath (0.3125% w/w)<br>(only one batch manufactured) |
| C | Reservoir Ring<br>LN-loaded DDU-4320 core (1% w/w LN) (cut prior to overmoulding)<br>DAP-loaded DDU-4320 sheath (0.3125% w/w)<br>(second batch) |

TABLE 8

Details of rings included in in vitro release study (n = 6).

| Ring Set | Mean ring mass (g) (±sd) | Mean core mass (g) (±sd) | Mean sheath mass (g) (±sd) | Mean theoretical LN loading (mg) (±sd) | Mean theoretical dapivirine loading (mg) (±sd) |
|---|---|---|---|---|---|
| A | 7.43 (±0.02) | 2.54 (±0) | 4.89 (±0.02) | 25.4 (±0) | 15.3 (±0.1) |
| B | 7.48 (±0.06) | 2.55 (±0) | 4.93 (±0.06) | 25.5 (±0) | 15.4 (±0.2) |
| C | 7.39 (±0.02) | 2.51 (±0.03) | 4.88 (±0.02) | 25.1 (±0.3) | 15.3 (±0.1) |

Figure 6A:
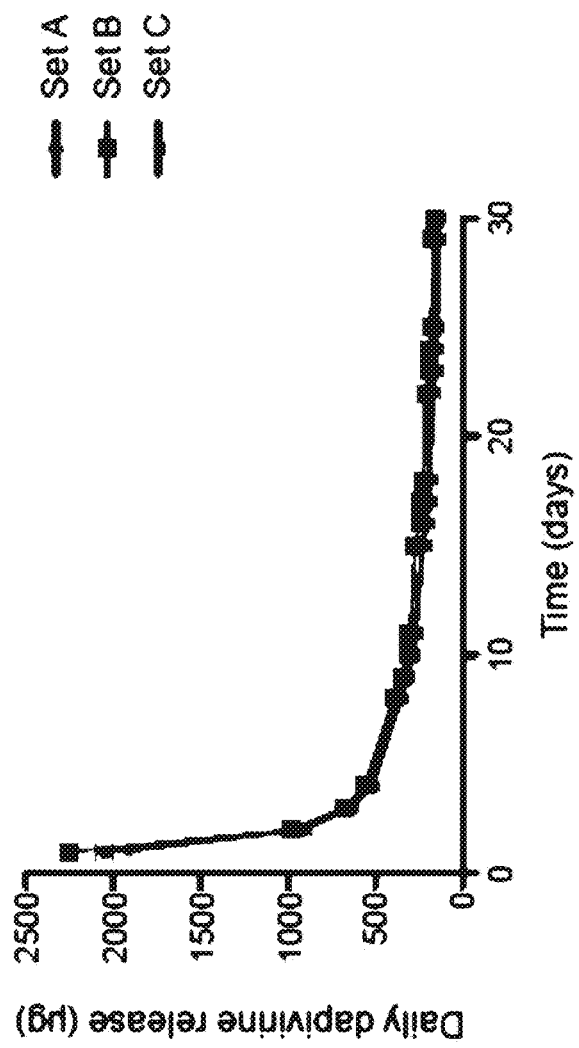
FIG. 6A and FIG. 6B depict the mean daily (FIG. 6A, ±sd) and cumulative (FIG. 6B) release of DAP from rings comprising a LNG-loaded core (1% w/w, DDU-4320) (sets A and C) or MED8-6382 (set B) and a DAP-loaded sheath (0.3125% w/w, DDU-4320) (n=6). The DAP daily release plots are very similar for the three ring sets. Cumulative release plots show a slight increase for Set B, likely due to the release enhancing influence of propanol produced as a by-product of the curing of the MED8-6382 silicone system.
Figure 6B:
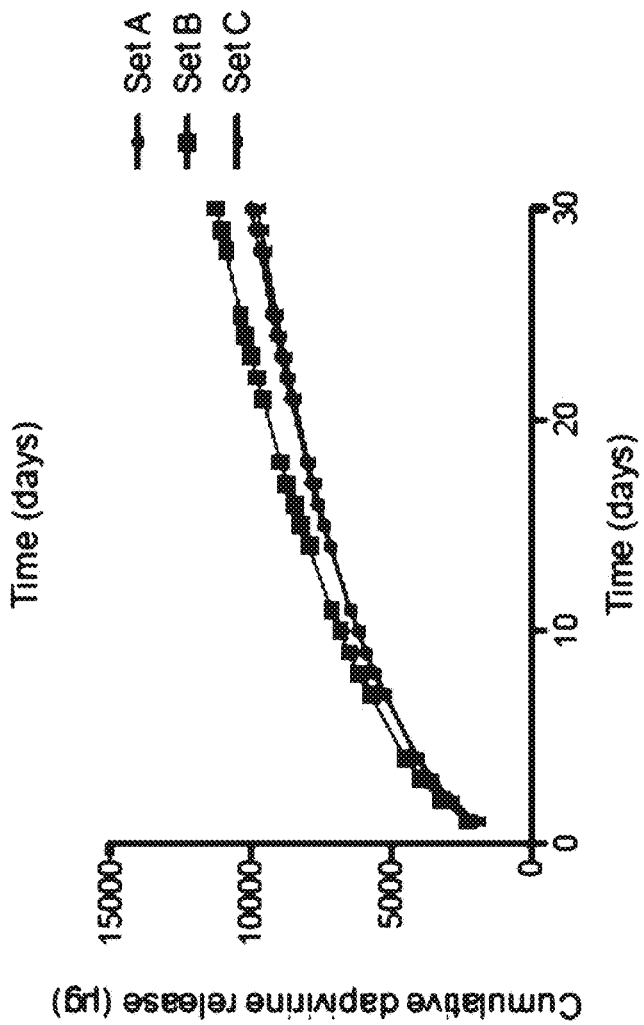
Figures 7A, 7B:
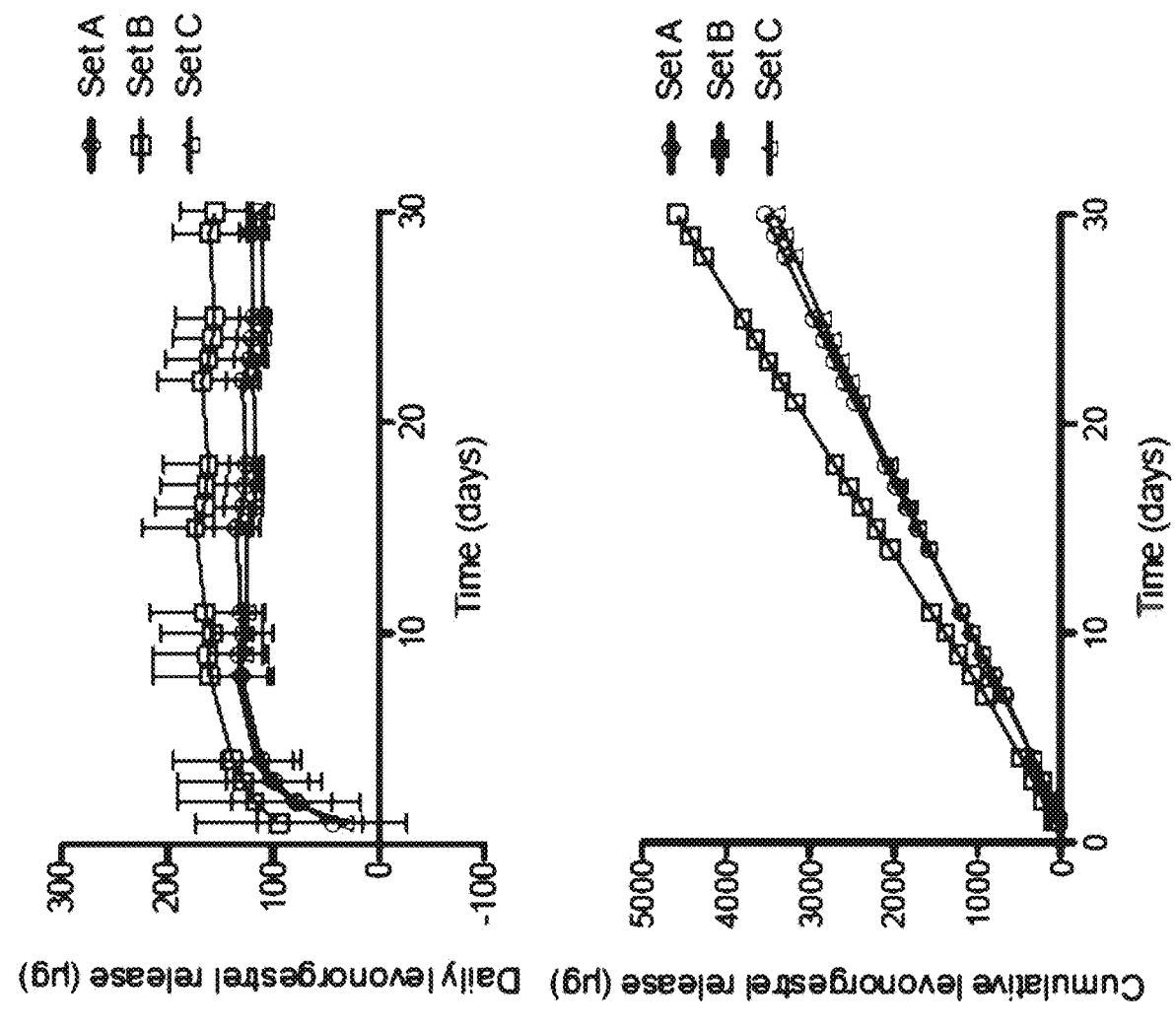
FIG. 7A and FIG. 7B depict the mean daily (FIG. 7A, ±sd) and cumulative (FIG. 7B) release of LNG from rings comprising a LNG-loaded core (1% w/w, DDU-4320) (sets A and C) or MED8-6382 (set B) and a DAP-loaded sheath (0.3125% w/w, DDU-4320) (n=6).

Daily and cumulative release rates for DAP and LNG from each ring set are presented in FIGS. 6 and 7, respectively. A summary of the in vitro release data is presented in FIGS. 8 and 9.

DAP release followed t1/2 kinetics for all ring sets (i.e., Sets A, B and C), as indicated by the release profiles and the linear relationship between cumulative release and root time ($R2 \geq 0.995$, see FIG. 6). The release rates for DAP from ring Sets A and C were very similar; 65 and 64% of the total DAP loading was released over the 30-day duration of the in vitro release study from Set A and Set C, respectively. The overall release rates were 1739 μg/day (Set A) and 1703 μg/day (Set C). These two sets of rings were prepared according to an identical manufacturing method, with one exception—the cores in ring Set A were not cut prior to overmolding, while the cores in Set C were cut as a means of ensuring the core was located centrally within the sheath. Given the similar release profile of DAP from the two formulations, it can be concluded that cutting the core does not have a marked effect on the release rate of DAP. The very small decrease in DAP release associated with Set C may be attributed to the reduced length/surface area of the core exposed to the overmolded, rate-limiting sheath layer. This indicates that the presence of LN in the core does not have a significant effect on the release of DAP from the ring.

The release of DAP from Set B was increased compared with Sets A and C. The cores in Set B rings were manufactured from MED8-6382, i.e., tin-catalysed silicone elastomer. A total of 73% of the initial DAP loading was released over 30 days, at a rate of 1971 μg/day. A likely reason for the enhanced release from MED8-6382 is the presence of propanol in the ring at manufacture, which is produced as a by-product during curing. The propanol is expected to increase solubility of DAP within the rings, and subsequently increase its release rate.

Release of LN followed zero order kinetics (i.e., near constant daily release rates) for all three formulations ($R2 \geq 0.9993$ for Sets A, B and C). Sets A and C provided similar LN release rates; for both sets, 14% of the original loading of LN was released over 30 days, with a mean release rate of 124 and 118 μg/day for Sets A and C, respectively. However, these results are markedly different to those obtained previously for a comparable formulation manufactured from LSR9-9508-30. The rings were manufactured using LSR9-9508-30 and consisted of a LN-loaded core and blank sheath; only 3% of the initial LN loading was released by day 30, with a mean release rate of 30 μg/day.

This discrepancy in the results prompted the manufacture and in vitro release testing of Set C, along with additional sets of control rings. Results from Set C confirmed those obtained for Set A, indicating that the presence of DAP in the sheath and/or the change in silicone elastomer batch has caused a substantial increase in the release rate of LN. LN release from rings consisting of a LN-loaded DDU-4320 core and blank DDU-4320 sheath was also higher than from those rings described previously. This indicates that while factors such as the change in the batch of silicone elastomer (from LSR9-9508-30 to DDU-4320; same material, updated product code) have impacted the LN release rate, the presence of DAP in the sheath is also causing an increase in LN release.

The release of LN was higher with Set B compared with Sets A and C, following the same trend observed for DAP release; 18% of the total loading was released at a rate of 159 μg/day. The presence of DAP in the sheath and/or the use of DDU-4320 causes an increase in the release rate of LN.

Summary of Example 2

DAP release follows t1/2 kinetics (typical of matrix devices) and occurs at a similar rate regardless of whether LN is present in the core of the ring.
LN release follows zero order kinetics (typical of reservoir devices) and occurs at a higher rate when DAP is present in the sheath.
Release of both DAP and LN is increased when the core of the ring is manufactured from MED8-6382 (tin-catalysed silicone elastomer) rather than DDU-4320 (platinum-catalysed silicone elastomer). This is attributed to the solubility enhancing effect of the propanol produced as a by-product of the silicone curing reaction.

A sheath thickness of 1.55 mm provides release of LN at a rate of approximately 120 μg/day (DAP being present in the sheath).

Example 3: Reservoir-Type Rings Comprising Dapivirine and a Contraceptive Loaded into a Single Core Reservoir-type vaginal rings consist of a drug-loaded core overmoulded with a rate-limiting polymeric sheath. Drug release occurs via the diffusion of solubilized drug molecules through the core and sheath materials followed by drug partitioning into the fluid medium surrounding the ring. With excess solid drug in the core to maintain the concentration of dissolved drug at saturation, drug release from reservoir-type rings obeys zero order kinetics, i.e., release occurs at a constant daily rate. The rate of drug release depends on the sheath thickness (reducing the thickness of the sheath results in an increase in drug release rate, when release is diffusion controlled), core length (reducing the length of the core results in a decrease in drug release rate) and the ability of the drug to permeate the sheath (a function of the drug's solubility and diffusion co-efficient in the material of the sheath). Unlike matrix-type rings, the drug loading in a reservoir-type ring has no effect on the rate of drug release (assuming excess solid drug is present, as stated above); however, drug loading does influence the duration of release.

Reservoir rings have the potential to deliver drug(s) over very long time periods, up to a year and perhaps even longer (assuming there is a sufficient quantity of drug located in the core to sustain drug release for this length of time). In this study, reservoir-type rings are explored for the purpose of providing release of both dapivirine (DAP) and levonorgestrel (LNG) for 6 months or longer at constant daily rates.

The simplest reservoir ring design comprises both drugs loaded into a single full-length core. A disadvantage with this approach may arise when the release rate of one drug needs to be altered relative to the other, since changing the sheath thickness and/or core length effects release of both drugs equally. An alternative approach is to load each drug into separate cores. In this study, both ring designs are investigated—a full-length core ring formulation containing both DAP and LNG, and another ring containing two half-length cores (DAP in the first and LNG in the second). Release data for the latter ring configuration allowed determination of the individual release rates of both drugs. This information may be used to design a reservoir ring where the release rate of each drug can be tailored independently of the other in order to obtain individual target release rates.

Dapivirine (micronised) was supplied by IPM. Levonorgestrel (non-micronised) was supplied by Haorui Pharma-Chem Inc. (Irvine, Calif.). DDU-4320 silicone elastomer was supplied by NuSil. Specifications of each API and the silicone elastomer are provided in Annex C. HPLC-grade acetonitrile, HPLC-grade isopropanol and potassium dihydrogen orthophosphate (AnalR analytical reagent) were purchased from VWR International Ltd. (Dublin, Ireland). Phosphoric acid (85% w/w in water) was purchased from Sigma-Aldrich (Gillingham, UK). A Millipore Direct-Q 3 UV Ultrapure Water System (Watford, UK) was used to obtain HPLC-grade water.

Reservoir-type vaginal rings comprising a full-length core containing both DAP and LNG (each at a loading of 2% w/w) and overmoulded with a blank sheath were manufactured using DDU-4320 on a laboratory-scale injection-moulding machine. The manufacture of reservoir rings using this equipment is a three-stage process: 1) Injection-moulding of the drug-loaded core, 2) Overmoulding one side of core with sheath layer, 3) Overmoulding of remaining exposed side of core to produce completely overmoulded/sheathed core, i.e., reservoir ring. The final ring consists of a central silicone elastomer core surrounded by a silicone elastomer sheath of uniform thickness (FIG. 10).

Figure 2B:
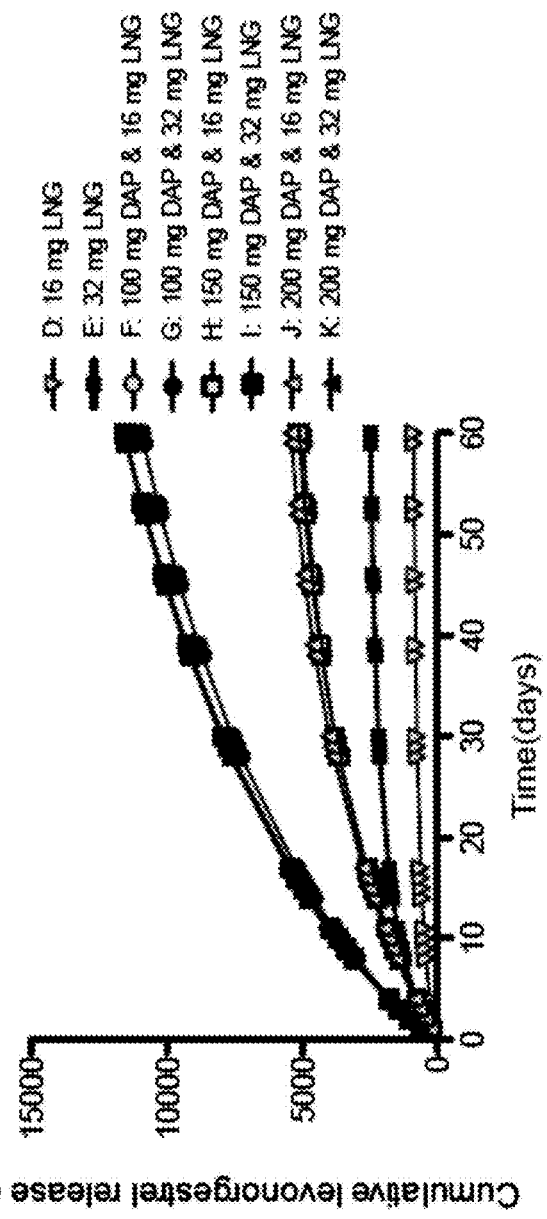

Cores were manufactured by mixing DDU-4320 (part A or B) with the appropriate mass of DAP and LNG (2% w/w loading of both drugs), using a FlackTek SpeedMixer™ DAC 150 FVZ-K (3000 rpm, 1.5 min), to form a premix. Premix A and Premix B were combined by speedmixing (1:1, 3000 rpm, 15 s) and then transferred to a SEMCO® injection cartridge. The cartridge was placed in a manual injection gun and the drug-loaded silicone elastomer was injected into a heated mould (90° C.) mounted on the injection-moulder and cured for 30 s. The dimensions of the core mould were as follows: Outer diameter=54.9 mm, Internal diameter=45.9 mm, Cross-sectional diameter=4.5 mm. Once cured, a cut was made at a single point in the core. The core was then transferred to a new mould set consisting of a lower core mould and an upper fullsize ring mould for the first stage of overmoulding (step 2 of the overall process). Parts A and B of DDU-4320 were mixed (1:1) in the SpeedMixer (3000 rpm, 15 s), then injected into the heated mould (90° C.) and cured for 90 s, as described for the cores (FIG. 2B).

The third and final manufacturing step involved transferring the partially sheathed core to another new mould set, consisting of full-size ring moulds on both the upper and lower platform of the injection-moulder. Overmoulding was completed by injection of the blank DDU-4320 A/B mix prepared for the first overmoulding stage, under the same conditions (90° C., 90 s cure time) (FIG. 2C). The dimensions of the full-size ring moulds were as follows: Outer diameter=58.0 mm, Internal diameter=42.8 mm, Cross-sectional diameter=7.6 mm.

This process produced reservoir rings with full-length cores, loaded with DAP and LNG (each at a loading of 2% w/w) and overmoulded with a blank sheath. A second formulation consisting of two half-length cores overmoulded with a blank sheath was also manufactured. Each half-length core was loaded with a single drug: one with DAP (2% w/w) and the other with LNG (2% w/w), i.e., each drug was formulated separately within the core of the ring. The two different core formulations were manufactured following the same process outlined previously for the DAP/LNG combination core, i.e., full-length complete cores were produced initially. These cores were cut in half to obtain a half-length drug-loaded core. At step 2 of the manufacturing process, one half-length DAP core and one half-length LNG core were each placed in the mould for overmoulding with blank silicone elastomer. The final overmoulding step, i.e., step 3 of the process, was the same as that outlined for the combination-core reservoir rings.

The two different reservoir-type rings manufactured will be referred to as Configuration 1 and Configuration 2 throughout this report (see FIG. 10):

Configuration 1: Full-length core loaded with both DAP and LNG, each at a loading of 2% w/w, overmoulded with blank DDU-4320.

Configuration 2: Two half-length cores, one loaded with DAP only (2% w/w) and the other loaded with LNG only (2% w/w), overmoulded with blank DDU-4320.

In vitro release testing was performed daily for 30 days. The sampling interval was then reduced to twice weekly (on two consecutive days) until day 95, and twice fortnightly thereafter (again, on two consecutive days). On Day 0, each ring was placed into a 250 mL glass bottle containing 50 mL dissolution medium (1:1 mixture of isopropanol and water) and stored in an orbital shaking incubator (37° C., 60 rpm, 25 mm orbital throw). The dissolution medium was sampled and replaced (50 mL) daily with the exception of weekends (100 mL added to maintain sink conditions).

After Day 30, 50 mL release medium was added over a daily interval and 200 mL was added over a weekly/fortnightly interval, as appropriate. Drug release was quantified by reverse-phase HPLC with UV detection.

Figure 11A:
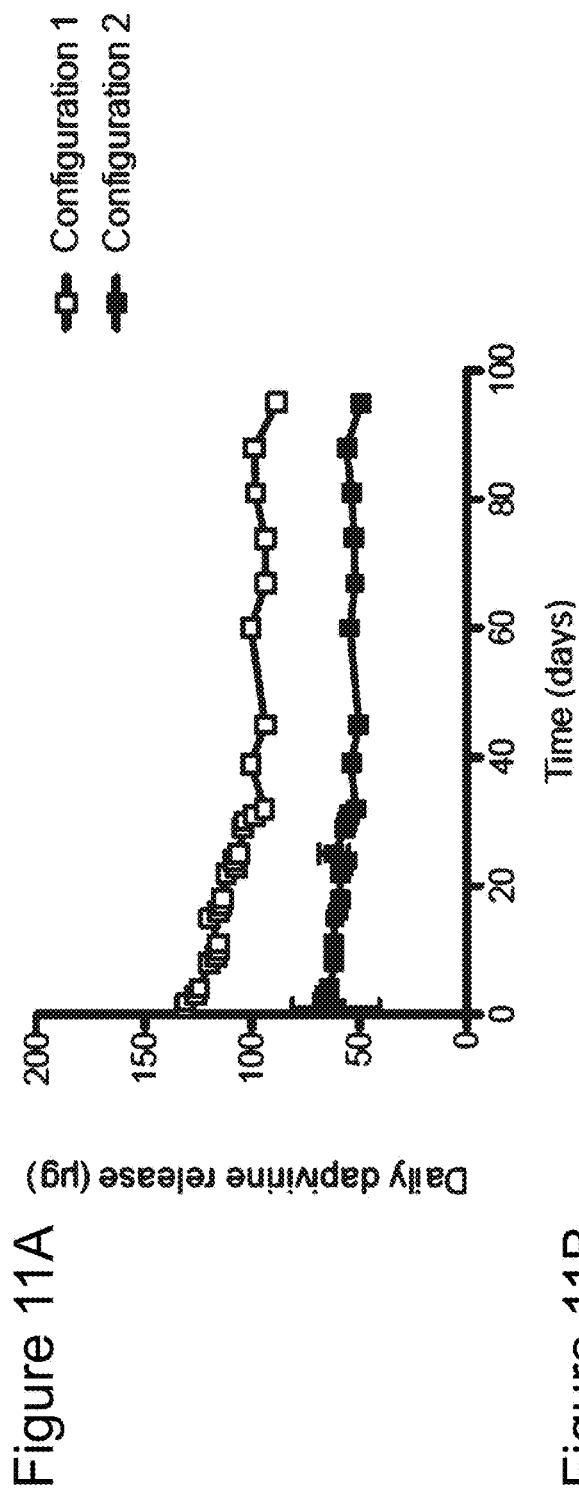
FIG. 11A and FIG. 11B depict the mean daily FIG. 11A, ±sd) and cumulative (FIG. 11B) release of dapivirine from each ring set (n=6).
Figure 11B:
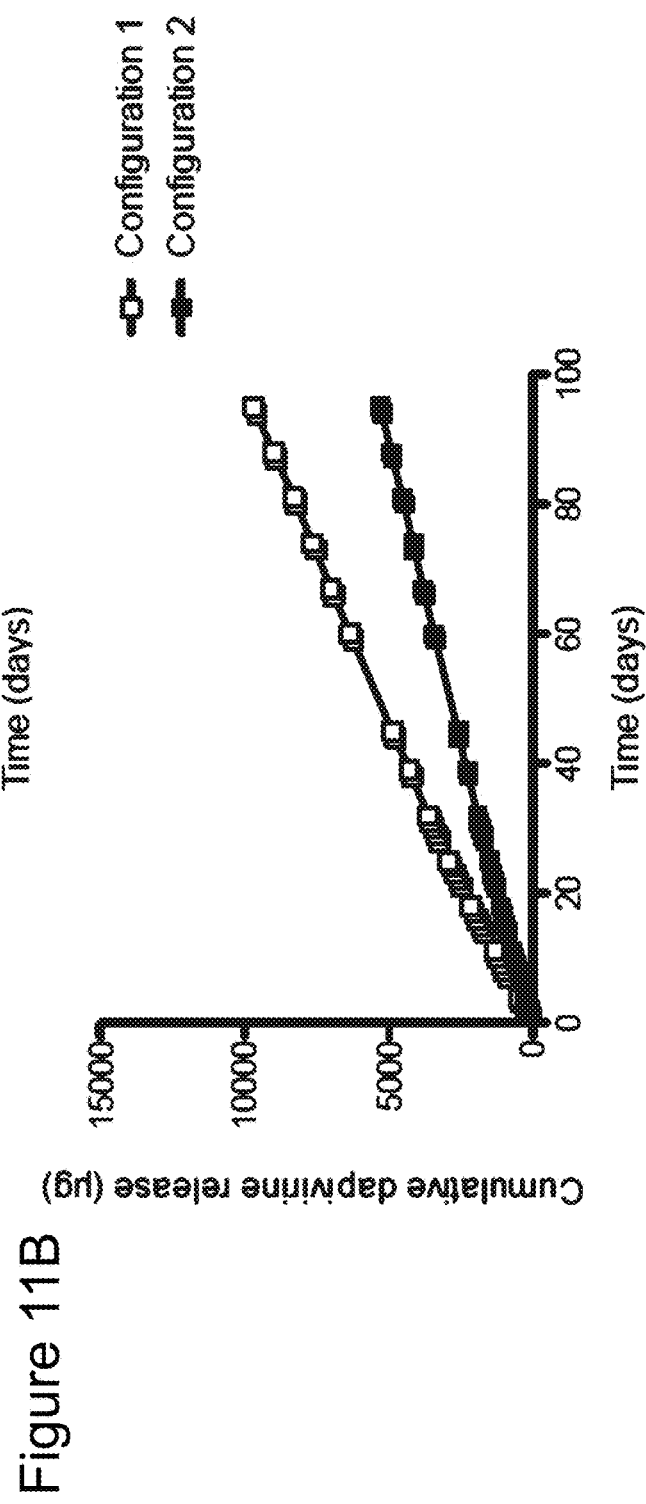

Details of the rings used in the study are provided in FIG. 10. Mean daily and cumulative release charts are presented in FIGS. 11 and 12. A summary of all in vitro release data is presented in Tables 9 and 10.

TABLE 9

Summary of dapivirine release data for each ring configuration (n = 6)

| DAPIVIRINE: | Configuration 1 | Configuration 2 |
|---|---|---|
| Daily release (μg) (±sd): | | |
| Day 1 | 131 (±3) | 61 (±20) |
| Day 30 | 103 (±1) | 56 (±1) |
| Day 60 | 100 (±2) | 54 (±1) |
| Day 95 | 88 (±1) | 49 (±1) |
| Cumulative release after 95 days (μg) (±sd) | 9670 (±61) | 5299 (±51) |
| % Release after 95 days | 19% | 21% |
| Daily release rate (μg/day) ($R^2$)* | 99 (0.9990) | 55 (0.9995) |
| Predicted duration of release** | ~8.5 months | ~7.7 months |

*linear regression analysis was performed when release data was plotted as cumulative release against time from day 7 onwards (charts not shown), $R^2$ value relates to this linear regression. **based on release rate determined from linear regression analysis of cumulative release against time, and assuming that zero order release occurs up to the point of 50% of the original drug lading released.

TABLE 10

Summary of levonorgestrel release data for each ring configuration (n = 6)

| LEVONORGESTREL | Configuration 1 | Configuration 2 |
|---|---|---|
| Daily release (μg) (±sd): | | |
| Day 1 | 8 (±1) | 0 (±0) |
| Day 30 | 138 (±2) | 57 (±1) |
| Day 60 | 134 (±2) | 55 (±1) |
| Day 95 | 110 (±3) | 47 (±1) |
| Cumulative release after 95 days (μg) (±sd) | 12194 (±72) | 4792 (± 85) |
| Daily release rate (μg/day) ($R^2$)* | 132 (0.9995) | 53 (1.000) |
| % Release after 95 days | 24% | 19% |
| Predicted duration of release** | ~6.5 months | ~8 months |

*linear regression analysis was performed when release data was plotted as cumulative release against time from day 7 onwards (charts not shown), $R^2$ value relates to this linear regression. **based on release rate determined from linear regression analysis of cumulative release against time, and assuming that zero order release occurs up to the point of 50% of the original drug loading released.

DAP and LNG release from both ring configurations occurred at a near constant daily rate (zero order release) over the 95-day period (FIGS. 11 and 12), as is typical of reservoir-type devices. These release rates are expected to continue out to 6 months, or perhaps longer (Tables 9 and 10).

Figure 12A:
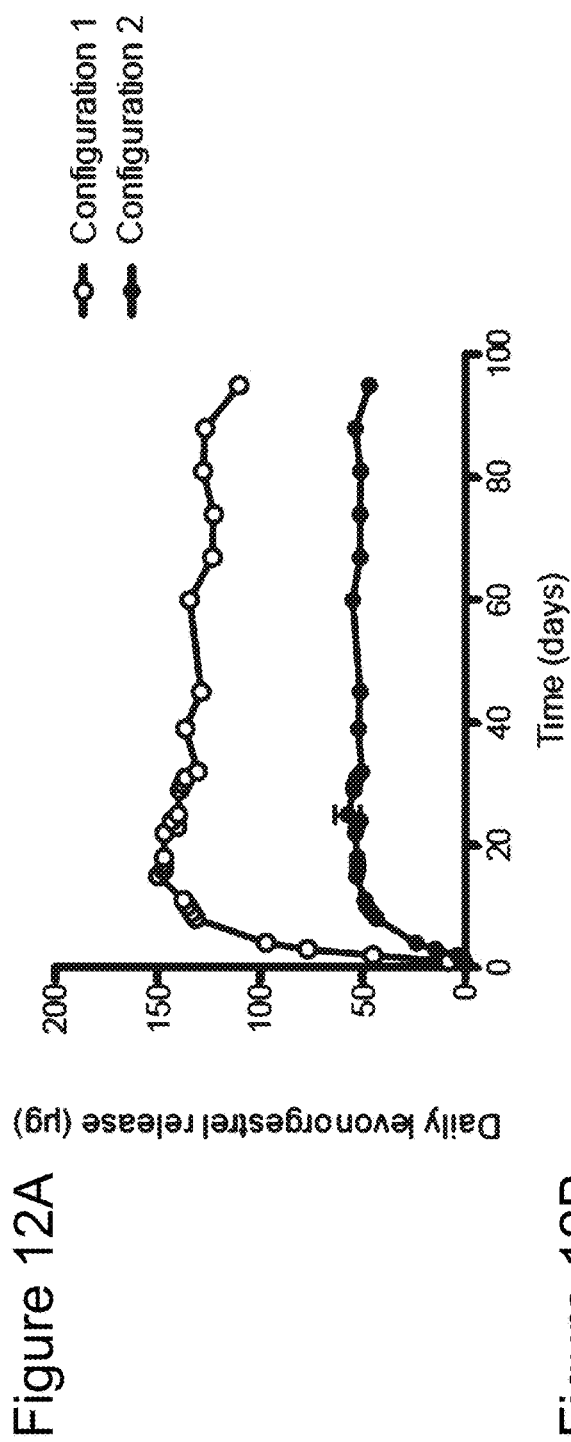
FIG. 12A and FIG. 12B depict the mean daily (FIG. 12A, ±sd) and cumulative (FIG. 12B) release of LNG from each ring set (n=6).
Figure 12B:
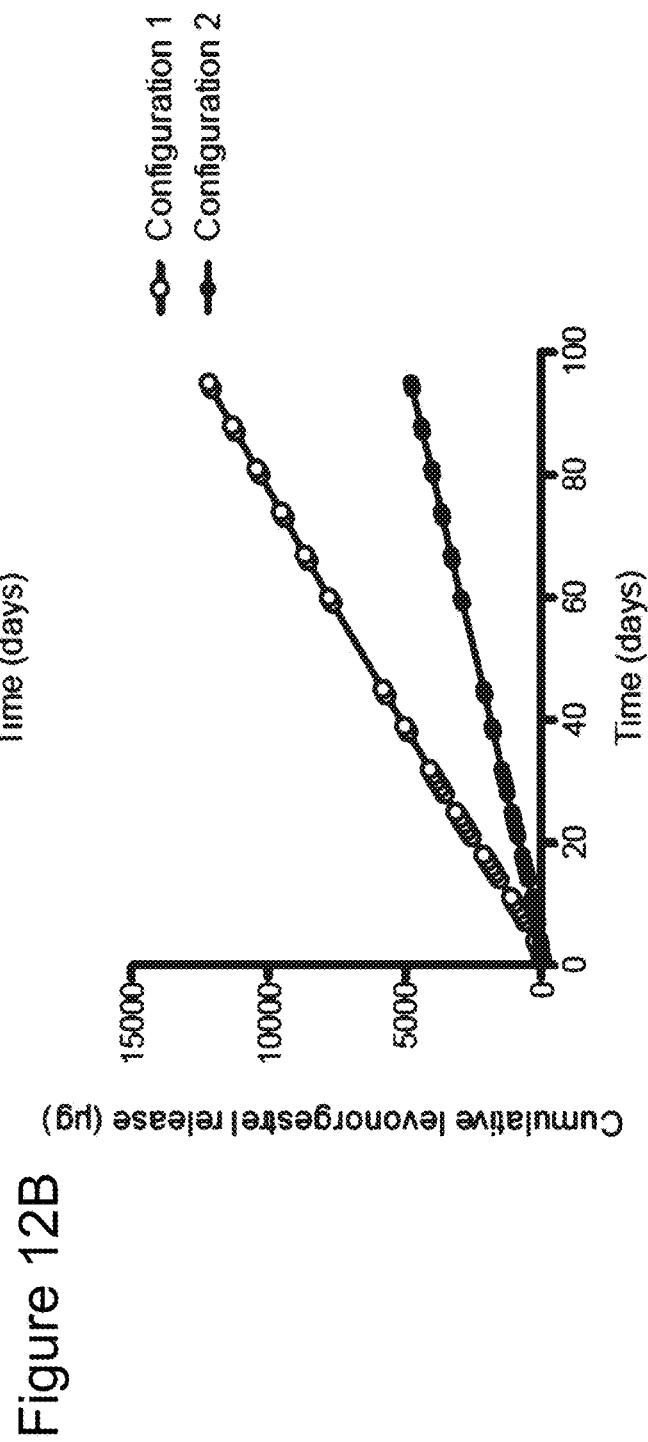

In order to confirm zero order release kinetics, linear regression analysis was applied to the cumulative release data from days 7 to 95 (release data from the initial timepoints was excluded owing to the lag effect with LNG, FIG. 12A). Linear relationships were observed between cumulative release and time for all four sets of release data (i.e., DAP and LNG from the two configurations) (Tables 9 and 10).

Release of DAP from Configuration 1 (99 μg/day, full-length core) was 1.8 fold higher that from Configuration 2 (55 μg/day, half-length core). Cranks equation predicts a doubling in the release rate, since release rate is directly proportional to core length.

The LNG release rate increased 2.5 fold when the core length was increased from half-length (Configuration 2, release rate 53 μg/day) to full-length (Configuration 1, release rate 132 μg/day).

In addition to the change in core length, the other difference between Configurations 1 and 2 relates to the formulation of drugs within the core. In Configuration 1, DAP and LNG are formulated in the same full-length core of the ring. In Configuration 2, each drug is formulated in separate half-length cores. The results indicate that DAP release is not substantially affected by the presence of LNG in the same compartment, since the release rate appears to be more closely proportional to core length.

This further indicates that formulation of DAP and LNG in the same core does not influence DAP release (note the similar release rate despite the lower drug loading; release rates are not influenced by loading in reservoir rings, but a higher loaded ring will provide a longer duration of release). However, in the case of LNG, the presence of DAP in the core may partly explain the greater than 2-fold increase in LNG release when the core length is doubled. Also, the increased surface area for drug release contributed by the core ends may also be a factor. Finally, it is possible that release of LNG is being influenced by the formation of a eutectic mixture between DAP and LNG in the combination core of Configuration 1.

LNG release from reservoir-type rings with a blank sheath was in the region of 89 µg/day; this increased to 118-124 µg/day when DAP was loaded in the sheath of the ring.

Summary of Example 3

Release is zero order for both drugs from both configurations
Configuration 1: DAP release rate=99 µg/day; LNG release rate=132 µg/day, LNG release rate was higher than DAP release rate, DAP release rate was lower than the target release rate of 200 µg/day, however, the release rate may be increased by decreasing the sheath thickness. LNG release rate was higher than the target release rate of 70 µg/day, however, the release rate may be reduced by increasing the sheath thickness and/or reducing the core length (as demonstrated by the results obtained for Configuration 2).
Configuration 2: DAP release rate=55 µg/day; LNG release rate=53 µg/day, DAP release rate is similar to LNG release rate. DAP release rate is approximately half the release rate of Configuration 1, i.e., release rate is halved by halving the core length. The presence of LNG in the core in Configuration 1 does not appear to affect DAP release. LNG release rate is less than half the release rate of Configuration 1, i.e., release is more than halved by halving the core length. The presence of DAP in the core affects LNG release.
A reservoir-type ring is suitable for providing constant daily release of both DAP and LNG.

Example 4: Vaginal Ring Configurations for Simultaneous Delivery of Dapivirine and Levonorgestrel Unintended pregnancy, HIV, and other sexually transmitted infections (STIs) all pose major reproductive health issues for women worldwide, particularly in developing countries where access to appropriate medication/contraceptives is limited. In recent years, there has been renewed interest in so-called multipurpose prevention technologies (MPTs) that can simultaneously address two or more clinical indications around reproductive health. MPTs may offer a number of advantages, including a reduced overall cost compared to individual products with a single indication, and potentially increased user adherence.

Intravaginal rings (VRs) are widely acknowledged as a useful technology platform for development of MPTs, since they can readily accommodate multiple drugs and provide long-term controlled release (FIG. 13). Single indication VRs are commercially available for use in hormonal contraception (e.g., NuvaRing®), and estrogen replacement therapy (e.g., Estring®). However, no combination therapy VRs are available to date.

In order to produce an intravaginal ring for the simultaneous controlled delivery of dapivirine (DAP) and a contraceptive, such as levonorgestrel (LNG) over 30 to 60 days to prevent both sexual transmission of HIV and unintended pregnancy, four types of intravaginal rings were developed C1-C4) (FIG. 13). The rings were manufactured by injection molding using medical-grade, addition-cured, silicone elastomer:
  i) Configuration 1 (C1)—Matrix ring; loaded with both DAP (0.3125% w/w) and LNG (0.1, 0.3 01' 1.0% w/w); FIG. 13A.
  ii) Configuration 2 (C2)—Reservoir ring; DAP and LNG formulated within a single full-length core (both 2% w/w), overmoulded with a blank sheath; FIG. 13B.
  iii) Configuration 3 (C3)—Reservoir ring; DAP and LNG formulated within two separate half-length cores (both 2% w/w), overmoulded with a blank sheath; FIG. 13C.
  iv) Configuration 4 (C4)—Reservoir ring; LNG formulated in a full-length core (1% w/w), overmoulded with a DAP-loaded sheath (0.3125% w/w); FIG. 13D.

In vitro release was assessed over 30 or 60 days. Each vaginal ring (n=6 per formulation) was placed in a stoppered bottle containing 200 mL (C1, day 0, decreased to 100 mL from day 1 onwards) or 100 mL (C2, C3 and C4, day 0, decreased to 50 mL from day 1 onwards) of release medium (1:1 mixture of isopropanol and water). Bottles were stored in an orbital shaking incubator (37° C., 60 rpm) and the release medium was sampled and completely replaced on a daily basis. Drug release was quantified using reverse-phase HPLC with UV detection (DAP: 210 nm; LNG: 240 nm). A 25 µL aliquot of each sample was injected onto a Thermo Scientific BDS Hypersil C18 column (150 mm×4.6 mm, 3 µm particle size) held at 25° C., and isocratic elution was performed: mobile phase 55% 7.7 mM phosphate buffer (pH 3.0)/45% HPLC-grade acetonitrile, flow rate 1.2 mL/min, run time 9 min, DAP and LNG were eluted after 6.2 and 7.7 min, respectively, The cumulative mass of DAP and LNG released from the various formulations was compared using a one-way ANOVA, followed by post-hoc analysis with the Tukey-Kramer multiple comparisons test when appropriate. A p value of less than 0.05 was considered significant.

Figure 16A:
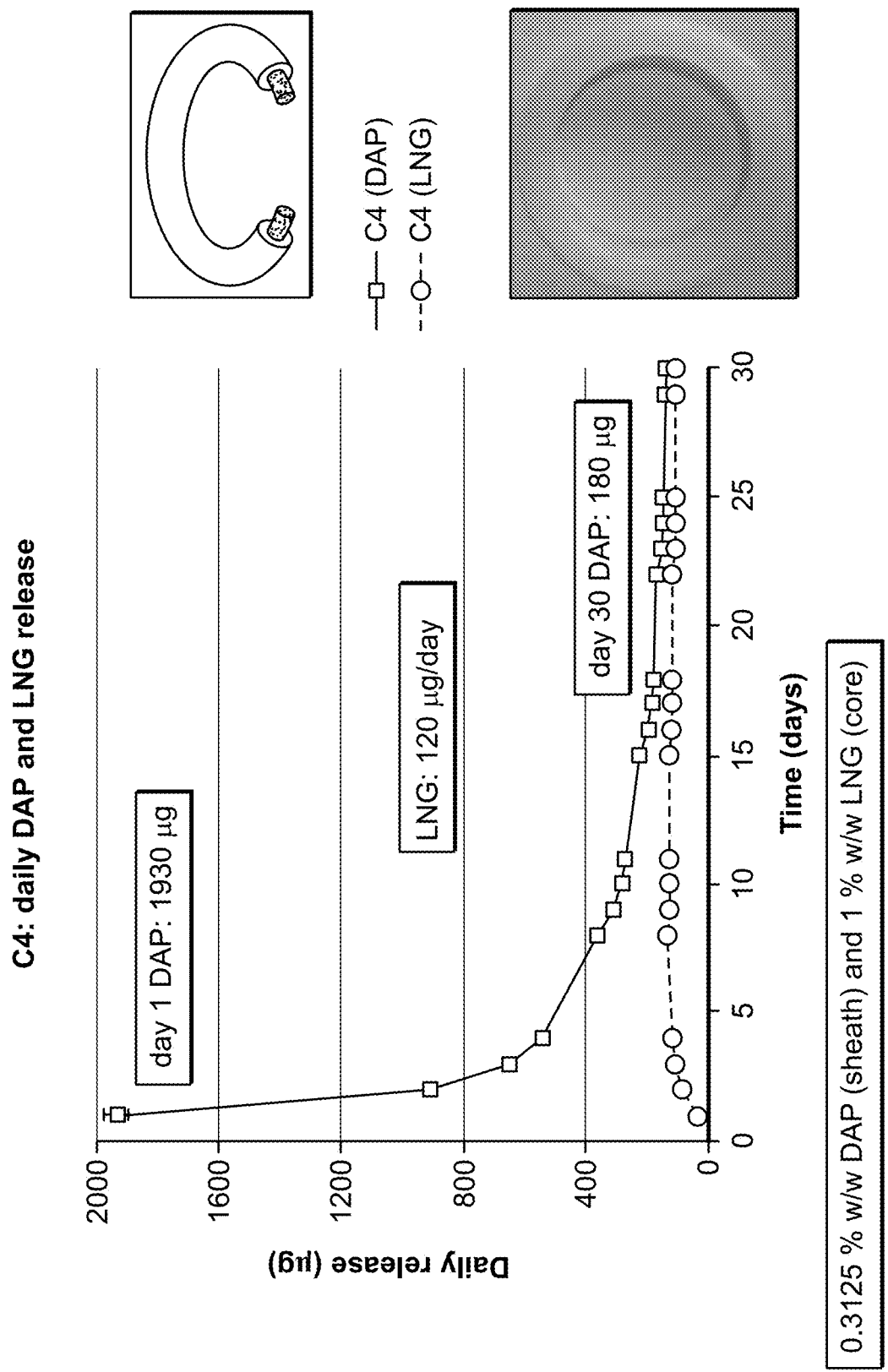
FIG. 16A and FIG. 16B depict (FIG. 16A) daily DAP and LNG release and (FIG. 16B) cumulative DAP and LNG release, respectively, from ring type C4 which is a reservoir-matrix-type ring with LNG loaded in the core and DAP loaded in the sheath.
Figure 16B:
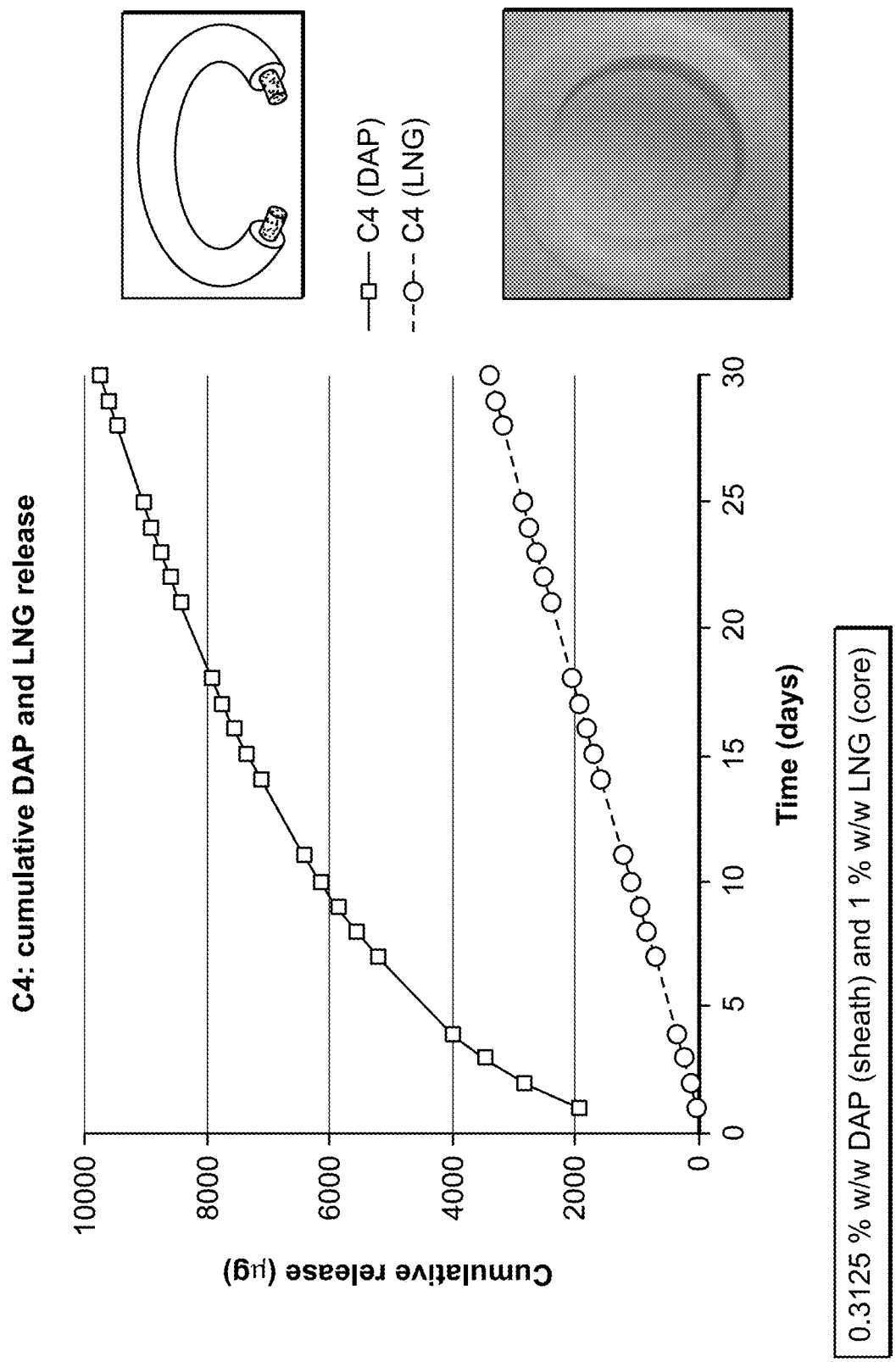

FIGS. 14A-D depict the daily dapivirine release, cumulative dapivirine release, daily LNG release, and cumulative LNG release from ring type C1, which is a matrix-type ring comprising both DAP and LNG. FIGS. 15A-D depict the daily dapivirine release, cumulative dapivirine release, daily LNG release, and cumulative LNG release from ring types C2 (reservoir-type ring with both DAP and LNG loaded in the core, surrounded by a blank sheath), and C3 (reservoir-type ring with DAP and LNG each loaded in separate half-cores, surrounded by a blank sheath). FIGS. 16A-B depict daily DAP and LNG release and cumulative DAP and LNG release, respectively, from ring type C4 which is a reservoir-matrix-type ring with LNG loaded in the core and DAP loaded in the sheath.

DAP and LNG were released from matrix rings (C1) according to root time kinetics, DAP and LNG release both increased significantly with LNG loading (p<0.05), DAP was released from C2 and C3 at a constant daily rate (i.e., zero order release), since it was formulated in the core of these reservoir rings (102 and 56 µg/day respectively, p<0.05). All reservoir rings (C2, C3 and C4) provided zero order release of LNG (135, 53 and 118 µg/day from C2, C3 and C4 respectively, p<0.05). The rate of release of DAP and LNG from reservoir rings increased significantly as the core length increased from half-length (C3) to full-length (C2). For C4 (where DAP was formulated in the sheath of the ring, i.e., similar to a matrix-type ring), DAP release followed root time kinetics, but the total cumulative release was significantly lower than C1 (p<0.05), indicating that the presence of LNG in the same compartment increases the release of DAP.

Figure 17:
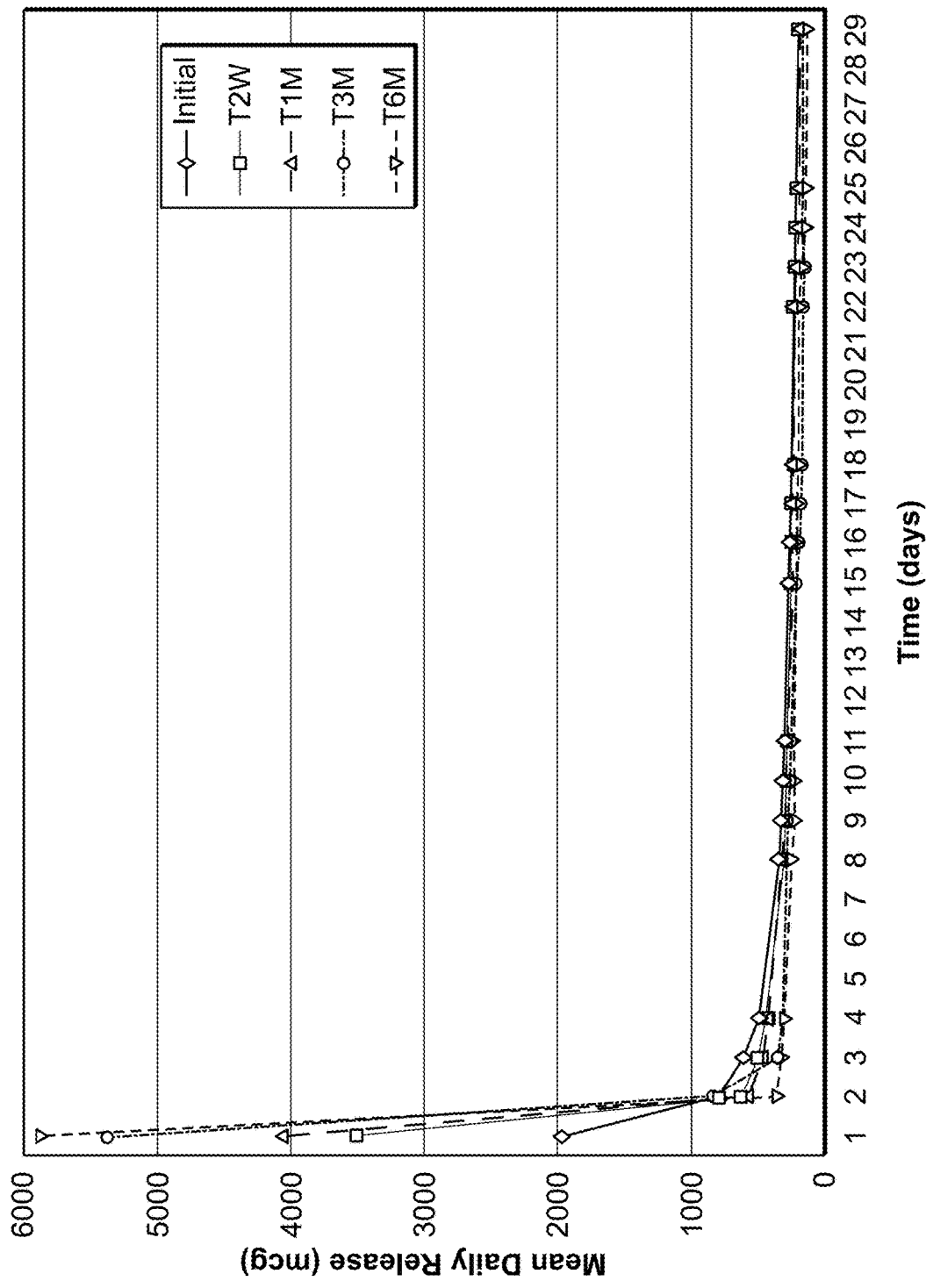
FIG. 17 depicts maraviroc release as a function of time in intravaginal matrix-type rings comprising 25 mg dapivirine and 100 mg of an antimicrobial compound, maraviroc.
Figure 18:
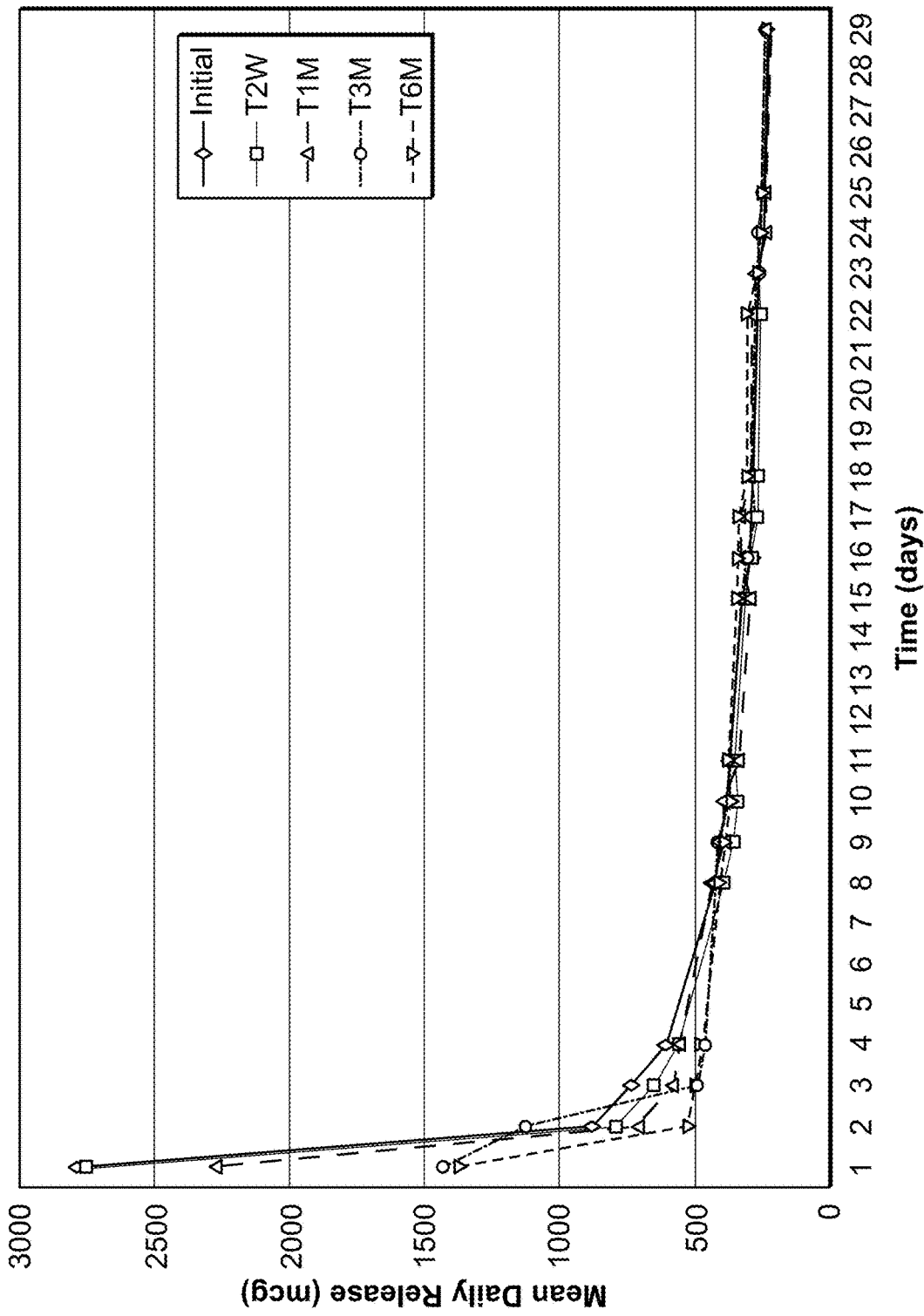
FIG. 18 depicts dapivirine release as a function of time in intravaginal matrix-type rings comprising 25 mg dapivirine and 100 mg of an antimicrobial compound, maraviroc.
Figure 19A:
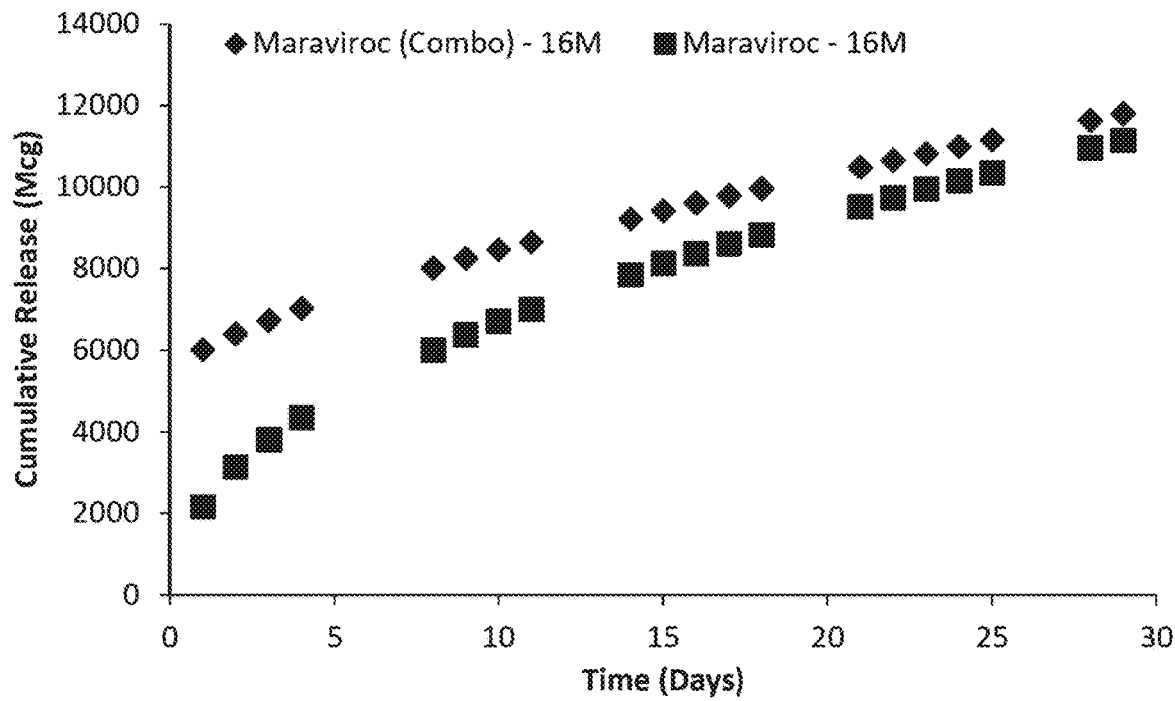
FIG. 19A and FIG. 19B depict the cumulative release of (FIG. 19A) maraviroc and (FIG. 19B) dapivirine from matrix-type intravaginal rings comprising either 16 mg maraviroc alone, 15 mg dapivirine alone, or 16 mg maraviroc and 16 mg dapivirine.
Figure 19B:
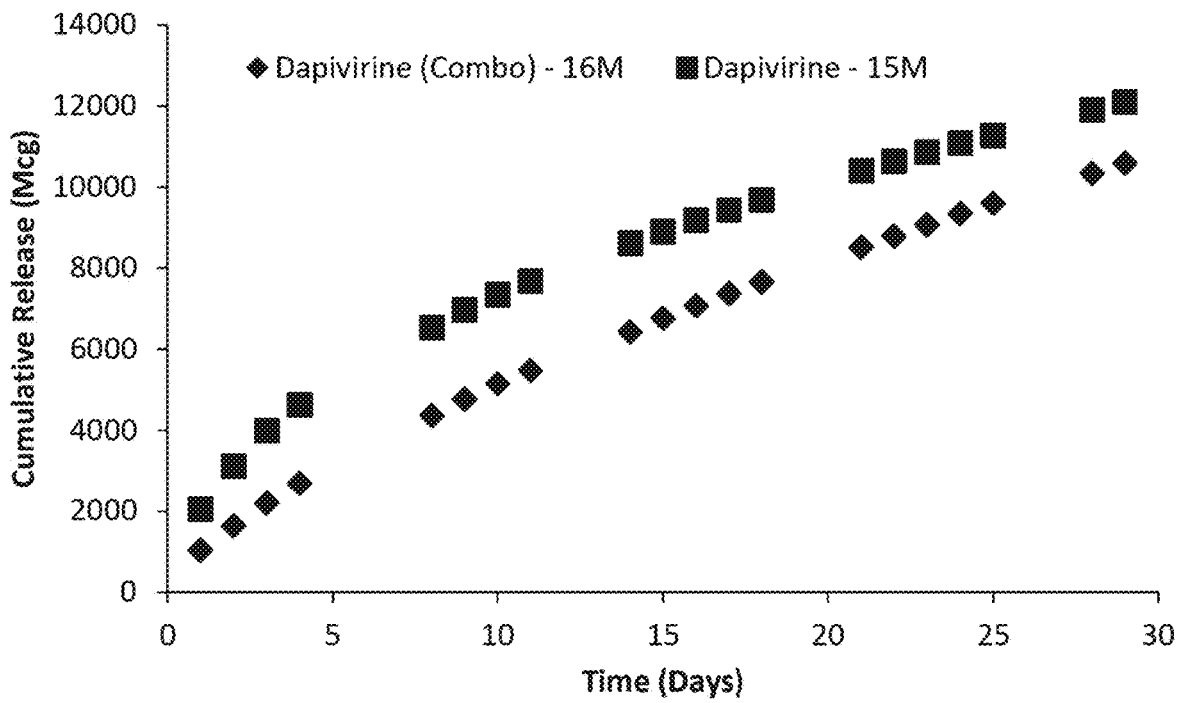
Figure 20A:
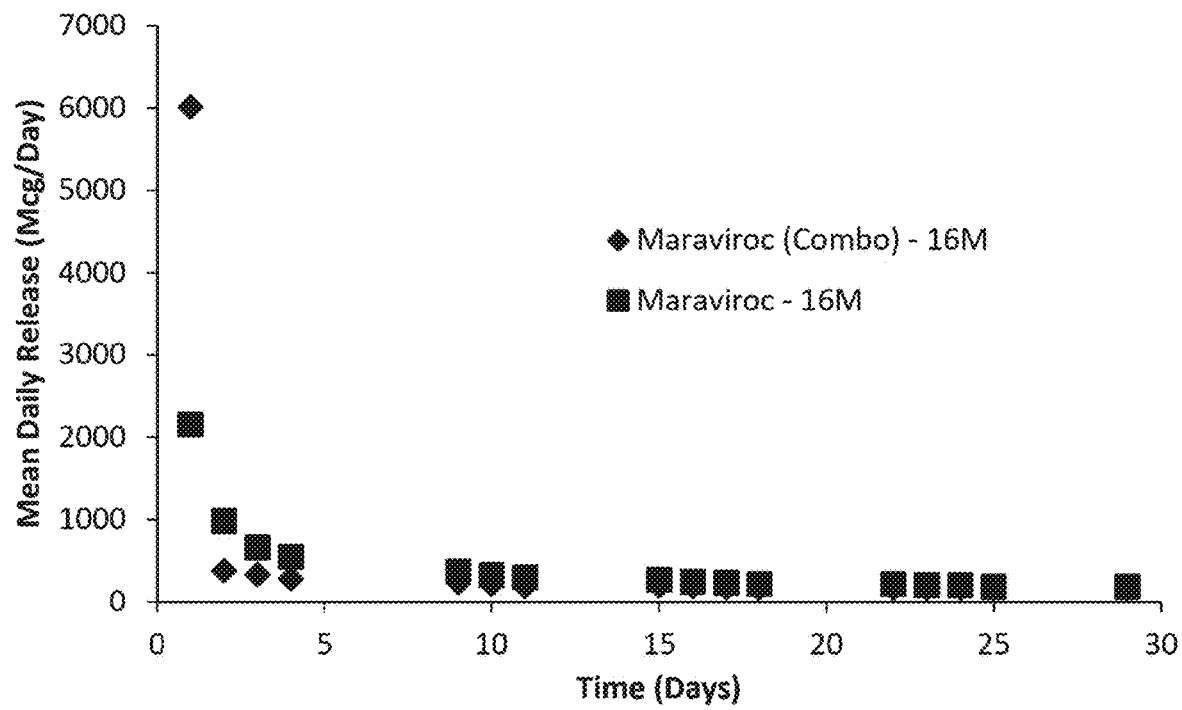
FIG. 20A and FIG. 20B depict the mean daily release of (FIG. 20A) maraviroc and (FIG. 20B) dapivirine from matrix-type intravaginal rings comprising either 16 mg maraviroc alone, 15 mg dapivirine alone, or 16 mg maraviroc and 16 mg dapivirine.
Figure 20B:
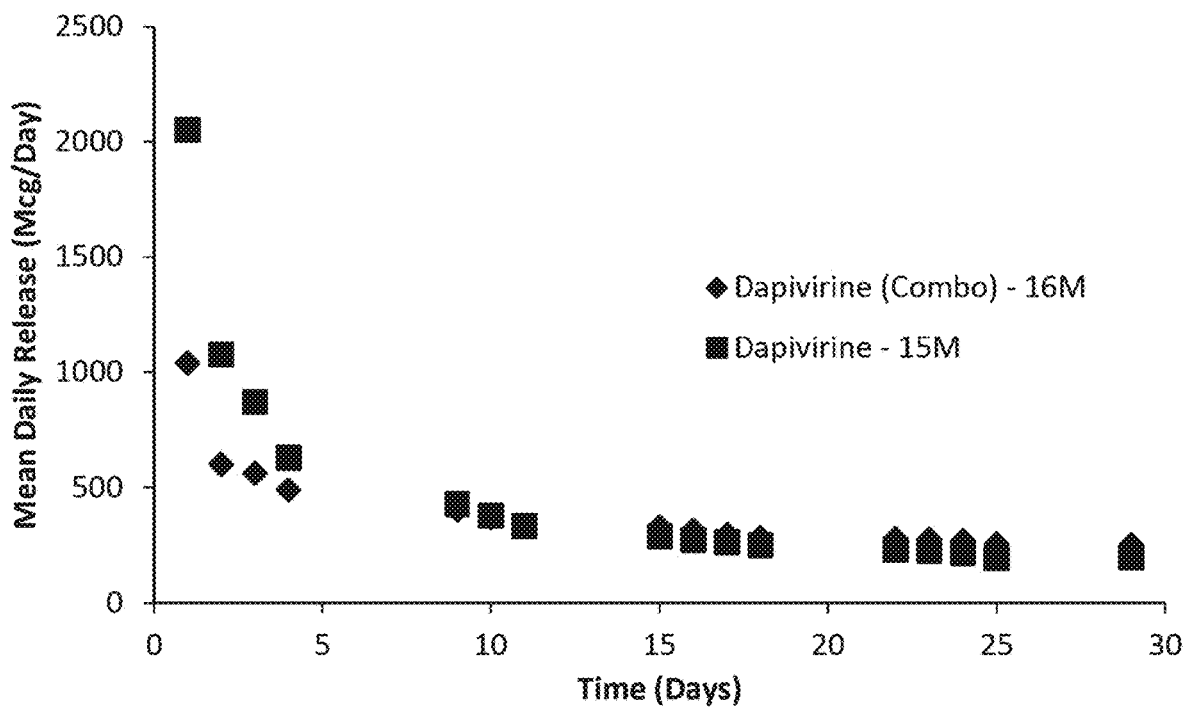

Example 5: Intravaginal Ring Comprising Dapivirine and an Antimicrobial Compound A platinum-catalyzed matrix-type silicone ring was created, comprising 25 mg dapivirine and 100 mg of an antimicrobial compound, maraviroc (both micronized and non-micronized). Both micronized maraviroc and non-micronized maraviroc rings were studied (see FIGS. 17 and 18). As can be seen in FIGS. 19 and 20, the release rate of maraviroc from the combination ring was higher than that of intravaginal rings comprising only maraviroc, likely due to the formation of a eutectic composition (see Example 6, below). Initial maraviroc release was lower and dapivirine release higher in micronized maraviroc rings compared to non-micronized maraviroc rings, but this had a limited effect on cumulative release.

Example 6: Eutectic Behavior of Dapivirine:Maraviroc Mixtures

Figure 21:
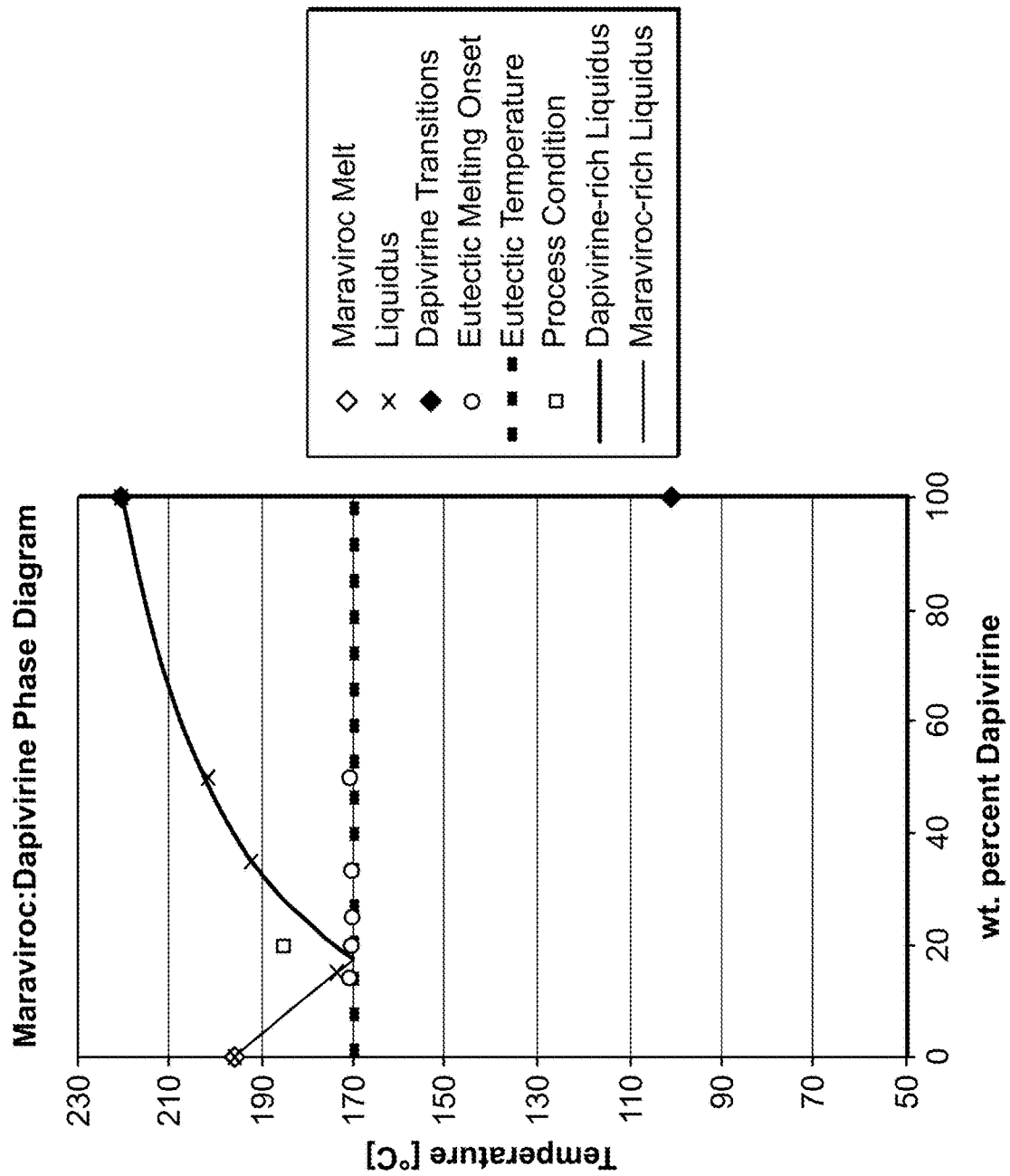
FIG. 21 depicts the phase behavior of maraviroc and dapivirine as a function of temperature and composition. The liquidus is the maximum temperature at which crystals can co-exist with the melt in thermodynamic equilibrium. Curves are based on freezing point depressing of each component due to the presence of the other component. The intersection is the estimated eutectic composition (17.5% dapivirine) and temperature (170° C.).

Maraviroc, dapivirine, and their mixtures were characterized and the results used to generate a phase diagram for the binary system (FIG. 21). The components are found to produce a simple eutectic system. Curves are based on freezing point depressing of each component due to the presence of the other component. The intersection is the estimated eutectic composition (17.4% dapivirine) and temperature (170° C.).

The pure components were analyzed using DSC, hot stage microscopy, TGA, transmission XRPD, and variable-temperature XRPD. Maraviroc in an orthorhombic crystal form was found to melt at 196° C. Micronized and non-micronized maraviroc had similar phase behavior, as expected. Dapivirine Form I underwent a solid-solid phase transition to Form II at 101° C. which subsequently melted at 220° C. Physical mixtures of the components were analyzed using DSC, hot stage microscopy, and variable-temperature XRPD. DSC was adequate to observe the solid-solid transformation in the dapivirine fraction and the onset of eutectic melting at 170° C. as confirmed using optical hot-stage microscopy.

The kinetics of phase transformations was found to be too slow to effectively use DSC to determine the full phase diagram. Therefore, variable-temperature X-ray powder diffraction (vT XRPD) was used to investigate the phase behavior of maraviroc and dapivirine as a function of temperature and composition. Slow cooling from the isotropic melt was employed until crystals nucleated. Substantial supercooling was required to initiate nucleation, particularly near the eutectic composition. Slow heating of the nucleated crystals was employed to bracket a point on the liquidus locus. The liquidus is the maximum temperature at which crystals can co-exist with the melt in thermodynamic equilibrium. Fitting functions to each of the branches of the liquidus locus permitted estimation of both the eutectic composition and temperature and completion of the phase diagram.

Example 7: Eutectic Behavior of Dapivirine:Levonorgestrel Mixtures

Similar to Example 6, above, levonorgestrel, dapivirine, and their mixtures were also characterized. The system appears to exhibit eutectic behavior with the eutectic temperature at about 193.5° C.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An intravaginal ring comprising 10 mg to 800 mg dapivirine and 10 mg to 1600 mg of an antimicrobial compound,
wherein less than about 7 mg of dapivirine is released in vitro from said ring during an initial 24 hour period of release, and
wherein the release rate of the antimicrobial compound from the intravaginal ring in vitro is increased as compared to the release rate of the antimicrobial compound from an intravaginal ring comprising the antimicrobial compound without dapivirine.

2. The intravaginal ring of claim 1, wherein the ring is a reservoir-type ring comprising a core and a sheath.

3. The intravaginal ring of claim 2, wherein the dapivirine and the antimicrobial compound are present in the core of the reservoir-type ring, and the sheath is blank.

4. The intravaginal ring of claim 2, wherein the dapivirine and the antimicrobial compound are present in two separate half-length cores, and the sheath is blank.

5. The intravaginal ring of claim 2, wherein the antimicrobial compound is present in the core, and the dapivirine is present in the sheath.

6. The intravaginal ring of claim 2, wherein the core is platinum-catalyzed; or wherein the core comprises a silicone polymer, an ethylene vinyl acetate EVA polymer, or a polyurethane polymer.

7. The intravaginal ring of claim 1, wherein the ring is a matrix-type ring.

8. The intravaginal ring of claim 7, wherein the ring is a platinum-catalyzed ring; or wherein the ring comprises a silicone polymer, an ethylene vinyl acetate EVA polymer, or a polyurethane polymer.

9. The intravaginal ring of claim 1, wherein between about 100 and about 700 µg of dapivirine is released in vitro each day for 23 days after an initial 7 day period of release.

10. The intravaginal ring of claim 1, wherein the antimicrobial compound is released in vitro at a rate of between about 200 µg per day and about 2000 µg per day, between about 400 µg per day and about 4000 µg per day, between about 550 µg per day and about 5500 µg per day, or between about 800 µg per day and about 8000 µg per day for 23 days or 53 days after an initial 7 day period of release.

11. The intravaginal ring of claim 1, wherein about 100 mg, about 150 mg, about 200 mg, about 10 to about 30 mg, about 25 mg, or about 15 mg of dapivirine is present in the ring.

12. The intravaginal ring of claim 1, wherein about 100 to about 800 mg, about 100 mg, about 400 mg, about 800 mg, or about 1600 mg, of the antimicrobial compound is present in the ring.

13. The intravaginal ring of claim 1, wherein the antimicrobial compound is maraviroc, DS003, darunavir, GSK1265744, or BMS-663068.

14. The intravaginal ring of claim 1, wherein release rates are stable following 3 months of storage; 6 months of storage; 12 months of storage; and/or 36 months of storage.

15. The intravaginal ring of claim 1, wherein the intravaginal ring has (a) an outer diameter of about 58 mm, an internal diameter of about 43 mm and a cross-sectional diameter of about 7.6 mm.; or (b) an outer diameter of about 57 mm and a cross-sectional diameter of about 7.8 mm.

16. A method of blocking DNA polymerization by an HIV reverse transcriptase enzyme in a female human, comprising the step of inserting the intravaginal ring of claim 1 into the vagina of the female human.

17. A method of preventing HIV infection in a female human, comprising the step of inserting the intravaginal ring of claim 1 into the vagina of the female human.

18. A method of treating HIV infection in a female human, comprising the step of inserting the intravaginal ring of claim 1 into the vagina of the female human.

19. An intravaginal ring comprising 10 mg to 800 mg dapivirine and 10 mg to 1600 mg of an antimicrobial compound,
  wherein less than about 7 mg of dapivirine is released in vitro from said ring during an initial 24 hour period of release, and
  wherein the dapivirine in the intravaginal ring increases the solubility of the antimicrobial compound as compared to the solubility of the antimicrobial compound in an intravaginal ring comprising the antimicrobial compound without dapivirine.

20. An intravaginal ring comprising a eutectic composition comprising 10 mg to 800 mg dapivirine and 10 mg to 1600 mg of an antimicrobial compound, wherein less than about 7 mg of dapivirine is released in vitro from said ring during an initial 24 hour period of release.

* * * * *